United States Patent
Brown, Jr. et al.

(10) Patent No.: US 11,629,347 B2
(45) Date of Patent: Apr. 18, 2023

(54) ANTI-C9ORF72 OLIGONUCLEOTIDES AND RELATED METHODS

(71) Applicant: UNIVERSITY OF MASSACHUSETTS, Boston, MA (US)

(72) Inventors: Robert H. Brown, Jr., Needham, MA (US); Jonathan K. Watts, Worcester, MA (US); Helene Tran, Shrewsbury, MA (US); Michael Moazami, Worcester, MA (US)

(73) Assignee: UNIVERSITY OF MASSACHUSETTS, Boston, ME (US)

( * ) Notice: Subject to any disclaimer, the term of this patent is extended or adjusted under 35 U.S.C. 154(b) by 106 days.

(21) Appl. No.: 16/868,237

(22) Filed: May 6, 2020

(65) Prior Publication Data
US 2020/0385723 A1 Dec. 10, 2020

Related U.S. Application Data

(60) Provisional application No. 62/843,740, filed on May 6, 2019.

(51) Int. Cl.
C12N 15/113 (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3231* (2013.01); *C12N 2310/3341* (2013.01)

(58) Field of Classification Search
CPC .................................................. C12N 15/113
See application file for complete search history.

(56) References Cited

U.S. PATENT DOCUMENTS

| | | |
|---|---|---|
| 4,522,811 A | 6/1985 | Eppstein et al. |
| 5,328,470 A | 7/1994 | Nabel et al. |
| 5,684,143 A | 11/1997 | Gryaznov et al. |
| 5,814,014 A | 9/1998 | Elsberry et al. |
| 5,858,988 A | 1/1999 | Wang |
| 6,093,180 A | 7/2000 | Elsberry |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,471,996 B1 | 10/2002 | Sokoll et al. |
| 6,472,375 B1 | 10/2002 | Hoon et al. |
| 7,399,845 B2 | 7/2008 | Seth et al. |
| 7,427,672 B2 | 9/2008 | Imanishi et al. |
| 7,459,547 B2 | 12/2008 | Zamore et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 9,605,263 B2 | 3/2017 | Rigo |
| 10,138,482 B2 * | 11/2018 | Rigo ........................ A61P 21/00 |
| 10,815,483 B2 | 10/2020 | Rigo |
| 2004/0171570 A1 | 9/2004 | Allerson et al. |
| 2005/0130923 A1 | 6/2005 | Bhat et al. |
| 2005/0220766 A1 | 10/2005 | Amalfitano et al. |
| 2006/0078542 A1 | 4/2006 | Mah et al. |
| 2007/0259827 A1 | 11/2007 | Aronin et al. |
| 2008/0269149 A1 | 10/2008 | Bowles et al. |
| 2009/0176725 A1 | 7/2009 | Morrissey et al. |
| 2010/0186103 A1 | 7/2010 | Gao et al. |
| 2014/0296486 A1 | 10/2014 | Gao et al. |
| 2015/0315587 A1 | 11/2015 | Uhlmann et al. |
| 2016/0251655 A1 | 9/2016 | Freier et al. |
| 2016/0304871 A1 | 10/2016 | Rigo |
| 2017/0037410 A1 * | 2/2017 | Swayze ................... A61P 25/28 |
| 2017/0312367 A1 | 11/2017 | Khvorova et al. |
| 2017/0349897 A1 | 12/2017 | Rigo |
| 2018/0023077 A1 | 1/2018 | Rigo |

(Continued)

FOREIGN PATENT DOCUMENTS

| | | | |
|---|---|---|---|
| WO | WO 1999/014226 A2 | 3/1999 | |
| WO | WO 2003/029459 A2 | 4/2003 | |

(Continued)

OTHER PUBLICATIONS

Agrawal, Sudhir, Importance of Nucleotide Sequence and Chemical Modifications of Antisense Oligonucleotides, Biochimica et Biophysica Acta (BBA)-Gene Structure and Expression, vol. 1489, No. 1, pp. 53-68., Dec. 10, 1999.

Aldern, et al., Increased Antiviral Activity of 1-O-Hexadecyloxypropyl-[2-14C]cidofovir in MRC-5 Human Lung Fibroblasts Is Explained by Unique Cellular Uptake and Metabolism, Molecular Pharmacology, vol. 63, Issue 3, pp. 678-681., Mar. 1, 2003.

Almeida, et al., Modeling Key Pathological Features of Frontotemporal Dementia with C9ORF72 Repeat Expansion in iPSC-Derived Human Neurons, Acta Neuropathologica, vol. 126, No. 3, pp. 385-399., 2013.

(Continued)

*Primary Examiner* — Ekaterina Poliakova-Georgantas
(74) *Attorney, Agent, or Firm* — Lathrop GPM LLP; James H. Velema, Esq.

(57) ABSTRACT

The present disclosure provides antisense compounds, methods, and compositions for silencing C9ORF72 transcripts. The present disclosure provides antisense compounds, methods, and compositions for the treatment, prevention, or amelioration of diseases, disorders, and conditions associated with C9ORF72 in a subject in need thereof. Also contemplated are antisense compounds and methods for the preparation of a medicament for the treatment, prevention, or amelioration of a disease, disorder, or condition associated with C9ORF72.

33 Claims, 22 Drawing Sheets
Specification includes a Sequence Listing.

(56) References Cited

U.S. PATENT DOCUMENTS

| | | | |
|---|---|---|---|
| 2018/0094267 | A1 | 4/2018 | Heslin et al. |
| 2018/0223284 | A1 | 8/2018 | Neuman et al. |
| 2018/0318330 | A1 | 11/2018 | Prakash et al. |
| 2019/0264204 | A1 | 8/2019 | Rigo |
| 2020/0157545 | A1 | 5/2020 | Vargeese et al. |
| 2020/0385723 | A1 | 12/2020 | Brown, Jr. et al. |
| 2021/0230589 | A1 | 7/2021 | Rigo |

FOREIGN PATENT DOCUMENTS

| | | |
|---|---|---|
| WO | WO 2003/004602 A3 | 11/2004 |
| WO | WO 2007/134181 A2 | 11/2007 |
| WO | WO 2008/101157 A1 | 8/2008 |
| WO | WO 2015/054676 A2 | 4/2015 |
| WO | WO 2015/057727 A1 | 4/2015 |
| WO | WO 2014/062691 A2 | 9/2016 |
| WO | WO 2016/168592 A2 | 10/2016 |
| WO | WO 2019/032607 A1 | 2/2019 |
| WO | WO 2020/227395 A2 | 11/2020 |
| WO | WO 2020/227395 A3 | 12/2020 |

OTHER PUBLICATIONS

Altschul, et al., Basic Local Alignment Search Tool, Journal of Molecular Biology, vol. 215, No. 3, pp. 403-410., Oct. 5, 1990.
Biscans, et al., Diverse Lipid Conjugates for Functional Extra-Hepatic siRNA Delivery in Vivo, Nucleic Acids Research, vol. 47, No. 3, pp. 1082-1096., Dec. 14, 2018.
Campbell, et al., Oligodeoxynucleoside Phosphorothioate Stability in Subcellular Extracts, Culture Media, Sera and Cerebrospinal Fluid, Journal of Biochemical and Biophysical Methods, vol. 20, Issue 3, pp. 259-267., Mar. 1990.
Crooke, et al., Pharmacokinetic Properties of Several Novel Oligonucleotide Analogs in Mice, Journal of Pharmacology and Experimental Therapeutics, vol. 277, Issue 2, pp. 923-937., May 1, 1996.
Dejesus-Hernandez, et al., Expanded GGGGCC Hexanucleotide Repeat in Noncoding Region of C9ORF72 Causes Chromosome 9p-Linked FTD and ALS, Neuron, vol. 72, pp. 245-256., 2011.
Devos, et al., Direct Intraventricular Delivery of Drugs to the Rodent Central Nervous System, JoVE (Journal of Visualized Experiments), vol. 75, e50326., pp. 1-10., May 12, 2013.
Donnelly, et al., RNA Toxicity from the ALS/FTD C9ORF72 Expansion is Mitigated by Antisense Intervention, Neuron, vol. 80, No. 2, pp. 415-428., Oct. 16, 2013.
Eckstein, Fritz, Phosphorothioate Oligodeoxynucleotides: What Is Their Origin and What Is Unique About Them?, Antisense and Nucleic Acid Drug Development, vol. 10, Issue 2, pp. 117-121., Jan. 30, 2009.
Eckstein, Fritz, Phosphorothioates, Essential Components of Therapeutic Oligonucleotides, Nucleic Acid Therapeutics, vol. 24, No. 6, pp. 374-387., Dec. 3, 2014.
Finkel, et al., Nusinersen versus Sham Control in Infantile-Onset Spinal Muscular Atrophy, The New England Journal of Medicine, vol. 377, pp. 1723-1732., Nov. 2, 2017.
Freibaum, et al., The Role of Dipeptide Repeats in C9ORF72-Related ALS-FTD, Frontiers in Molecular Neuroscience, vol. 10, Issue 35, 9 pages, 2017.
Geary, et al., Pharmacokinetics, Biodistribution and Cell Uptake of Antisense Oligonucleotides, Advanced Drug Delivery Reviews, vol. 87, pp. 46-51., Jun. 29, 2015.
Gendron, et al., Antisense Transcripts of the Expanded C9ORF72 Hexanucleotide Repeat form Nuclear RNA Foci and Undergo Repeat-Associated Non-ATG Translation in C9FTD/ALS, Acta Neuropathologica, vol. 126, No. 6, pp. 829-844., 2013.
Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210., Aug. 1998.
Herdewijn, Piet, Heterocyclic Modifications of Oligonucleotides and Antisense Technology, Antisense and Nucleic Acid Drug Development, vol. 10, Issue 4, pp. 297-310., Jul. 8, 2004.
Hostetler, et al., Alkoxyalkyl Prodrugs of Acyclic Nucleoside Phosphonates Enhance Oral Antiviral Activity and Reduce Toxicity: Current State of the Art, Antiviral Research, vol. 82, Issue 2, 39 Pages., May 2009.
Hostetler, et al., In Vitro and in Vivo Activity of 1-O-Hexadecylpropane-Diol-3-Phospho-Ganciclovir and 1-O-Hexadecylpropanediol-3-Phospho-Penciclovir in Cytomegalovirus and Herpes Simplex Virus Infections, Antiviral Chemistry and Chemotherapy, vol. 12, No. 1, pp. 61-70., Feb. 1, 2001.
International Search Report & Written Opinion Received for PCT Application No. PCT/US2020/031654, dated Oct. 28, 2020, 14 Pages.
Ittig, et al., Academy of Sciences of the Czech Republic, Prague, pp. 21-26., 2005.
Ittig, et al., Nuclear Antisense Effects in Cyclophilin a pre-mRNA Splicing by Oligonucleotides: A Comparison of Tricyclo-DNA With LNA, Nucleic Acids Research, vol. 32, Issue 1, pp. 346-353., Jan. 1, 2004.
Ivanova, et al., Tricyclo-DNA Containing Oligonucleotides as Steric Block Inhibitors of Human Immunodeficiency Virus Type 1 Tat-Dependent Trans-Activation and HIV-1 Infectivity, Oligonucleotides, vol. 17, No. 1, pp. 54-65., Apr. 26, 2007.
Jiang, et al., Gain of Toxicity from ALS/FTD-Linked Repeat Expansions in C90RF72 Is Alleviated by Antisense Oligonucleotides Targeting GGGGCC-Containing RNAs, Neuron, vol. 90, No. 3, pp. 535-550., May 6, 2016.
Kabanov, et al., A New Class of Antivirals: Antisense Oligonucleotides Combined With a Hydrophobic Substituent Effectively Inhibit Influenza Virus Reproduction and Synthesis of Virus-Specific Proteins in MDCK Cells, FEBS Letters, vol. 259, Issue 2, pp. 327-330., Jan. 1, 1990.
Koshkin, et al., LNA (Locked Nucleic Acid): An RNA mimic forming exceedingly stable LNA:LNA duplexes, Journal of the American Chemical Society, vol. 120, pp. 13252-13253., Dec. 8, 1998.
Krieg, Arthur M., CpG Motifs in Bacterial DNA and their Immune Effects, Annual Review of Immunology, vol. 20, No. 1, pp. 709-760., 2002.
Lagier-Tourenne, et al., Targeted Degradation of Sense and Antisense C9orf72 RNA Foci as Therapy for ALS and Frontotemporal Degeneration, Proceedings of the National Academy of Sciences, vol. 110, No. 47, pp. E4530-E4539., 2013.
Letsinger, et al., Cholesteryl-Conjugated Oligonucleotides: Synthesis, Properties, and Activity as Inhibitors of Replication of Human Immunodeficiency Virus in Cell Culture, Proceedings of the National Academy of Sciences of the United States of America, vol. 86, No. 17, pp. 6553-6556., Sep. 1989.
Leumann, Christian J.., DNA Analogues: From Supramolecular Principles to Biological Properties, Bioorganic & Medicinal Chemistry, vol. 10, Issue 4, pp. 841-854., Apr. 2002.
Manoharan, et al., Chemical Modifications to Improve Uptake and Bioavailability of Antisense Oligonucleotides, Annals of the New York Academy of Sciences, vol. 660, Issue 1, pp. 306-309., Oct. 1992.
Manoharan, et al., Cholic Acid-Oligonucleotide Conjugates for Antisense Applications, Bioorganic & Medicinal Chemistry Letters, vol. 4, Issue 8, pp. 1053-1060., Apr. 21, 1994.
Manoharan, et al., Introduction of a Lipophilic Thioether Tether in the Minor Groove of Nucleic Acids for Antisense Applications, Bioorganic & Medicinal Chemistry Letters, vol. 3, Issue 12, pp. 2765-2770., Dec. 1993.
Manoharan, et al., Lipidic Nucleic Acids, Tetrahedron Letters, vol. 36, Issue 21, pp. 3651-3654., May 22, 1995.
Manoharan, et al., Oligonucleotide Conjugates: Alteration of the Pharmacokinetic Properties of Antisense Agents, Nucleosides, Nucleotides & Nucleic Acids, vol. 14, Issue 3-5, pp. 969-973., 1995.
McCaffrey, et al., Gene Expression: RNA Interference in Adult Mice, Nature, vol. 418, No. 6893, pp. 38-39., Jul. 4, 2002.
Mishra, et al., Improved Leishmanicidal Effect of Phosphorotioate Antisense Oligonucleotides by LDL-Mediated Delivery, Biochimica

(56) References Cited

OTHER PUBLICATIONS et Biophysica Acta (BBA)—Gene Structure and Expression, vol. 1264, Issue 2, pp. 229-237., Nov. 7, 1995.
Mizielinska, et al., C9orf72 Frontotemporal Lobar Degeneration is Characterised by Frequent Neuronal Sense and Antisense RNA Foci, Acta Neuropathologica, vol. 126, No. 6, pp. 845-857., Oct. 30, 2013.
Nikan, et al., Docosahexaenoic Acid Conjugation Enhances Distribution and Safety of siRNA upon Local Administration in Mouse Brain, Molecular Therapy—Nucleic Acids, vol. 5, No. 8, pp. 1-11., Aug. 9, 2016.
Oberhauser, et al., Effective Incorporation of 2'-O-Methyl-Oligoribonuclectides Into Liposomes and Enhanced Cell Association Through Modification With Thiocholesterol, Nucleic Acids Research, vol. 20, Issue 3, pp. 533-538., Feb. 11, 1992.
O'Rourke, et al., C9orf72 BAC Transgenic Mice Display Typical Pathologic Features of ALS/FTD, Neuron, vol. 88, No. 5, pp. 892-901., Dec. 2, 2015.
Peters, et al., Human C9ORF72 Hexanucleotide Expansion Reproduces RNA Foci and Dipeptide Repeat Proteins but not Neurodegeneration in BAC Transgenic Mice, Neuron, vol. 88, No. 5, pp. 902-909., Dec. 2, 2015.
Prakash, et al., Targeted Delivery of Antisense Oligonucleotides to Hepatocytes Using Triantennary N-Acetyl Galactosamine Improves Potency 10-Fold in Mice, Nucleic Acids Research, vol. 42, Issue 13, pp. 8796-8807., Jul. 29, 2014.
Putnam, David A., Antisense Strategies and Therapeutic Applications, American Journal of Health System Pharmacy, vol. 53, No. 2, pp. 151-160., Jan. 15, 1996.
Putnam, et al., Antisense Strategies and Therapeutic Applications, American Journal of Health-System Pharmacy, vol. 53, No. 3, p. 325., 1996.
Raal, et al., Mipomersen, an Apolipoprotein B Synthesis Inhibitor, for Lowering of LDL Cholesterol Concentrations in Patients with Homozygous Familial Hypercholesterolaemia: a Randomised, Double-Blind, Placebo-Controlled Trial, The Lancet, vol. 375, No. 9719, pp. 998-1006., Mar. 14, 2010.
Renneberg, et al., Antisense Properties of Tricyclo-DNA, Nucleic Acids Research, vol. 30, Issue 13, pp. 2751-2757., Jul. 1, 2002.
Renneberg, et al., Exploring Hoogsteen and Reversed-Hoogsteen Duplex and Triplex Formation with Tricyclo-DNA Purine Sequences, Chembiochem, vol. 5, Issue 8, pp. 1114-1118., Aug. 2, 2004.
Renneberg, et al., Watson-Crick Base-Pairing Properties of Tricyclo-DNA, Journal of the American Chemical Society, vol. 124, No. 21, pp. 5993-6002., May 7, 2002.
Rigo, et al., Pharmacology of a Central Nervous System Delivered 2'-O-Methoxyethyl-Modified Survival of Motor Neuron Splicing Oligonucleotide in Mice and Nonhuman Primates, Journal of Pharmacology and Experimental Therapeutics, vol. 350, Issue 1, pp. 46-55., Jul. 1, 2014.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345., Jan. 30, 2009.
Sareen, et al., Targeting RNA Foci in iPSC-Derived Motor Neurons from ALS Patients with a C9ORF72 Repeat Expansion, Science Translational Medicine, vol. 5, No. 208, 208ra149, pp. 1-26., Oct. 23, 2013.
Shea, et al., Synthesis, Hybridization Properties and Antiviral Activity of Lipid-Oligodeoxynucleotide Conjugates, Nucleic Acids Research, vol. 18, Issue 13, pp. 3777-3783., Jul. 11, 1990.
Smith, et al., Comparison of Biosequences, Advances in Applied Mathematics, vol. 2, No. 4, pp. 482-489., Dec. 1981.
Sørensen, et al., α-L-ribo-Configured Locked Nucleic Acid (α-L-LNA): Synthesis and Properties, Journal of the American Chemical Society, vol. 124, No. 10, pp. 2164-2176., 2002.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325., Oct. 2001.

Svinarchuk, et al., Inhibition of HIV Proliferation in MT-4 Cells by Antisense Oligonucleotide Conjugated to Lipophilic Groups, Biochimie, vol. 75, Issues 1-2, pp. 49-54., 1993.
Swayze, et al., Antisense Oligonucleotides Containing Locked Nucleic Acid Improve Potency but Cause Significant Hepatotoxicity in Animals, Nucleic Acids Research, vol. 35, No. 2, pp. 687-700., Dec. 19, 2006.
Tran, et al., Differential Toxicity of Nuclear RNA Foci versus Dipeptide Repeat Proteins in a *Drosophila* Model of C90RF72 FTD/ALS, Neuron, vol. 87, No. 7,, pp. 1207-1214., Sep. 23, 2015.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85., Apr. 2011.
Whitesell, et al., Stability, Clearance, and Disposition of Intraventricularly Administered Oligodeoxynucleotides: Implications for Therapeutic Application within the Central Nervous System, Proceedings of the National Academy of Sciences, vol. 90, No. 10, pp. 4665-4669., May 1993.
Wolfrum, et al., Mechanisms and Optimization of in Vivodelivery of Lipophilic siRNAs, Nature Biotechnology, vol. 25, No. 10, pp. 1149-1157., Sep. 16, 2007.
Woolf, et al., Specificity of Antisense Oligonucleotides In Vivo, Proceedings of the National Academy of Sciences, vol. 89, No. 16, pp. 7305-7309., Aug. 15, 1992.
Xia, et al., siRNA-Mediated Gene Silencing in Vitroand In Vivo, Nature Biotechnology, vol. 20, No. 10, pp. 1006-1010., Sep. 16, 2002.
Zhang, et al., PowerBLAST: A New Network BLAST Application for Interactive or Automated Sequence Analysis and Annotation, Genome Research, vol. 7, No. 6, pp. 649-656., Jun. 1997.
Zu, et al., RAN Proteins and RNA Foci from Antisense Transcripts in C9ORF72 ALS and Frontotemporal Dementia, Proceedings of the National Academy of Sciences, vol. 110, No. 51, pp. E4968-E4977., Nov. 18, 2013.
International Preliminary Report on Patentability for PCT International Patent Application No. PCT/US2020/025432, dated May 17, 2021.
Vickers et al., Efficient reduction of target RNAs by small interfering RNA and RNase H-dependent antisense agents. A comparative analysis, The Journal of Biological Chemistry, 2003, 278: 7108-7118.
Webster et al., The C9orf72 protein interacts with Rab1a and the ULK1 complex to regulate initiation of autophagy, The EMBO Journal, 2016, 35: 1656-1676.
Zhang et al., Several rAAV vectors efficiently cross the blood-brain barrier and transduce neurons and astrocytes in the neonatal mouse central nervous system, Mol. Ther., 19(8):1440-1448, doi: 10.1038/mt.2011.98, (May 24, 2011).
Alisky et al., "Gene therapy for amyotrophic lateral sclerosis and other motor neuron diseases", Hum Gene Ther.,11(17):2315-2329, doi: 10.1089/104303400750038435, (Nov. 20, 2000).
Alvarez-Erviti et al., "Delivery of siRNA to the mouse brain by systemic injection of targeted exosomes", Nat Biotechnol., 29(4):341-345, doi: 10.1038/nbt.1807, (Apr. 2011).
Ambros et al., "MicroRNAs and other tiny endogenous RNAs in C. elegans", Curr Biol, 13, 807-18, doi: 10.1016/50960-9822(03)00287-2, (2003).
Atwell et al., "Stable heterodimers from remodeling the domain interface of a homodimer using a phage display library", J Mol Biol., 270(1):26-35, doi: 10.1006/jmbi.1997.1116, (Jul. 4, 1997).
Bagella., "Cloning of murine CDK9/PITALRE and its tissue-specific expression in development", J. Cell. Physiol., 177: 206-213, (Dec. 1998).
Bell et al., "Liposomal transfection efficiency and toxicity on glioma cell lines: in vitro and in vivo studies", Neuroreport., Mar. 30, 1998, 9(5):793-8, doi: 10.1097/00001756-199803300-00005.
Billy et al., "Specific interference with gene expression induced by long, double-stranded RNA in mouse embryonal teratocarcinoma cell lines", Proc Natl Acad Sci USA, 98(25): 14428-14233, doi: 10.1073/pnas.261562698. (Dec. 4, 2001).
Braasch et al., "RNA Interference in Mammalian Cells by Chemically-Modified RNA", Biochemistry, 42:7967-7975, (2003).

(56) References Cited

OTHER PUBLICATIONS

Brennecke et al., "bantam encodes a developmentally regulated microRNA that controls cell proliferation and regulates the proapoptotic gene hid in Drosophila", Cell, 113(1):25-36, doi: 10.1016/s0092-8674(03)00231-9, (Apr. 4, 2003).
Brummelkamp et al., "A System for Stable Expression of Short Interfering RNAs in Mammalian Cells", Science, 296, 550-553, (2002).
Byrne et al., "Novel Hydrophobically Modified Asymmetric RNAi Compounds (sd-rxRNA) Demonstrate Robust Efficacy in the Eye", J Ocul Pharmacol Ther., 29(10):855-864, doi: 10.1089/jop.2013.0148. (Nov. 1, 2013).
Calegari et al., "Tissue-specific RNA interference in postimplantation mouse embryos with endoribonuclease-prepared short interfering RNA", Proc Natl Acad Sci USA, 99(22):14236-14240, doi: 10.1073/pnas.192559699, (Oct. 29, 2002).
Chen et al., "Gene therapy for brain tumors: Regression of experimental gliomas by adenovirus-mediated gene transfer in vivo", Proc. Natl. Acad. Sci. USA, 91, 3054-3057, (1994).
Cheng et al., "Enhanced hepatic uptake and bioactivity of type alpha1(I) collagen gene promoter-specific triplex-forming oligonucleotides after conjugation with cholesterol", Journal of Pharmacology and Experimental Therapeutics, 317(2):797-805, DOI: doi.org/10.1124/jpet.105.100347, (May 2006).
Dass, "Cytotoxicity issues pertinent to lipoplex-mediated gene therapy in-vivo", J Pharm Pharmacol., 54(5):593-601, doi: 10.1211/0022357021778817, (May 2002).
Davidson et al., "A model system for in vivo gene transfer into the central nervous system using an adenoviral vector", Nat Genet., 3(3):219-23, doi: 10.1038/ng0393-219, (Mar. 1993).
Davidson et al., "Recombinant adeno-associated virus type 2, 4, and 5 vectors: Transduction of variant cell types and regions in the mammalian central nervous system", PNAS, 97(7):3428-3432, doi.org/10.1073/pnas.97.7.3428, (Mar. 28, 2000).
Doench et al., "siRNAs can function as miRNAs", Genes Dev., 17(4):438-42, doi: 10.1101/gad.1064703, (Feb. 15, 2003).
Egusquiaguirre et al., "Nanoparticle delivery systems for cancer therapy: advances in clinical and preclinical research", Clin Transl Oncol., 14(2):83-93, doi: 10.1007/s12094-012-0766-6, (Feb. 2012).
El Andaloussi et al., "Exosomes for targeted siRNA delivery across biological barriers", Adv Drug Deliv Rev., 65(3):391-397, doi: 10.1016/j.addr.2012.08.008, (Mar. 2013).
El Andaloussi et al., "Extracellular vesicles: biology and emerging therapeutic opportunities", Nat Rev Drug Discov., 12(5):347-357, doi: 10.1038/nrd3978, (May 2013).
El-Andaloussi et al., "Exosome-mediated delivery of siRNA in vitro and in vivo", Nat Protoc., 7(12):2112-2126, doi: 10.1038/nprot.2012.131, (2012).
Elmen et al., "Locked nucleic acid (LNA) mediated improvements in siRNA stability and functionality", Nucleic Acids Res., 33(1):439-447, doi: 10.1093/nar/gki193, (Jan. 14, 2005).
Fattal et al., "Biodegradable polyalkylcyanoacrylate nanoparticles for the delivery of oligonucleotides", J Control Release, 53(1-3):137-43, doi: 10.1016/s0168-3659(97)00246-0, (Apr. 30, 1998).
Fisher et al., "Transduction with Recombinant Adeno-Associated Virus for Gene Therapy Is Limited by Leading-Strand Synthesis", J Virol., 70:520 532, (Jan. 1996).
Giege et al., "Crystallization of Nucleic Acids and Proteins, a Practical Approach", $2^{nd}$ eds., pp. 20 1-16, Oxford University Press, New York, New York, (1999).
Godard et al., "Antisense effects of cholesterol-oligodeoxynucleotide conjugates associated with poly(alkylcyanoacrylate) nanoparticles", Eur J Biochem., 232(2):404-410, (Sep. 1, 1995).
Grad et al., "Computational and experimental identification of C. elegans microRNAs", Mol Cell., May 2003, 11 (5):1253-1263, doi: 10.1016/s1097-2765(03)00153-9.
Griffiths-Jones, "The microRNA Registry", Nucleic Acids Res., 32(Database issue): D109-D111, doi: 10.1093/nar/gkh023, (Jan. 1, 2004).

Haeusler et al., "The expanding biology of the C9orf72 nucleotide repeat expansion in neurodegenerative disease", Nature Reviews Neuroscience, vol. 17, pp. 383-395 (2016).
Hutvagner et al., "A microRNA in a multiple-turnover RNAi enzyme complex", Science, 297(5589):2056-2060, doi: 10.1126/science.1073827, (Aug. 1, 2002).
International Search Report and Written Opinion of PCT/US2020/025432, dated Sep. 18, 2020.
Jacque et al., "Modulation of HIV-1 replication by RNA interference", Nature, 418(6896):435-438, doi: 10.1038/nature00896, (Jun. 26, 2002).
Karlin et al., "Methods for assessing the statistical significance of molecular sequence features by using general scoring schemes", Proc. Natl. Acad. Sci. USA, 87:2264-2268, (Mar. 1990).
Lagos-Quintana et al., "Identification of novel genes coding for small expressed RNAs", Science, 294(5543):853-858, doi: 10.1126/science.1064921, (Oct. 26, 2001).
Lagos-Quintana et al., "Identification of tissue-specific microRNAs from mouse", Curr Biol., 12(9):735-739, doi: 10.1016/s0960-9822(02)00809-6, (Apr. 30, 2002).
Lagos-Quintana et al., "New microRNAs from mouse and human", RNA, 9(2):175-179, doi: 10.1261/rna.2146903, (Feb. 2003).
Lai et al., "Computational identification of DrosophilamicroRNA genes", Genome Biol., 2003, 4(7):R42. doi: 10.1186/GB-2003-4-7-r42. (Jun. 30, 2003).
Lambert et al., "Nanoparticulate systems for the delivery of antisense oligonucleotides", Adv Drug Deliv Rev., 47(1):99-112, doi: 10.1016/s0169-409x(00)00116-2, (Mar. 23, 2001).
Lau et al., "An abundant class of tiny RNAs with probable regulatory roles in Caenorhabditis elegans", Science, 294(5543):858-862, doi: 10.1126/science.1065062, (Oct. 26, 2001).
Lee et al., "An extensive class of small RNAs in Caenorhabditis elegans", Science, 294(5543):862-864, doi: 10.1126/science.1065329, (Oct. 26, 2001).
Lee et al., "Recent Developments in Nanoparticle-Based siRNA Delivery for Cancer Therapy", BioMed Research International, vol., Article ID 782041, 10 pages, doi:10.1155/2013/782041, (2013).
Lewis et al., "Efficient delivery of siRNA for inhibition of gene expression in postnatal mice", Nat Genet., 32(1):107-108, doi: 10.1038/ng944, (Jul. 29, 2002).
Lim et al., "The microRNAs of Caenorhabditis elegans", Genes Dev., Apr. 15, 2003, 17(8):991-1008, doi: 10.1101/gad.1074403.
Lim et al., "Vertebrate microRNA genes", Science, 299(5612):1540, doi: 10.1126/science. 1080372, (Mar. 7, 2003).
Liu et al., "Hydrodynamics-based transfection in animals by systemic administration of plasmid DNA", Gene, Ther. 6, 1258-1266, (1999).
Martier et al. "Targeting RNA-Mediated Toxicity in C9orf72 ALS and/or FTD by RNAi-Base Gene Therapy", Molecular Therapy: Nucleic Acids, vol. 16, pp. 26-37, (Feb. 11, 2019).
Masotti et al., "Comparison of different commercially available cationic liposome-DNA lipoplexes: Parameters influencing toxicity and transfection efficiency", Colloids Surf B Biointerfaces, 68(2):136-144, doi: 10.1016/j.colsurfb.2008.09.017, (Sep. 25, 2008).
Mathis et al., "RNA-Targeted Therapies and Amyotrophic Lateral Sclerosis", Biomedicines, vol. 6, No. 1, pp. 1-11, (Jan. 15, 2018).
McManus et al., "Gene silencing using micro-RNA designed hairpins", RNA, 8(6):842-850, doi: 10.1017/s1355838202024032. 2002, (Jun. 2002).
Miyagishi et al., "U6 promoter-driven siRNAs with four uridine 3' overhangs efficiently suppress targeted gene expression in mammalian cells", Nat Biotechnol., 20(5):497-500, doi: 10.1038/nbt0502-497, (May 2002).
Mourelatos et al., "miRNPs: a novel class of ribonucleoproteins containing numerous microRNAs", Genes Dev., 16(6): 720-728, (Mar. 15, 2002).
Nielsen, et al., "Sequence-selective recognition of DNA by strand displacement with a thymine-substituted polyamide", Science;254(5037):1497-1500, doi: 10.1126/science. 1962210, (December6, 1991).
Paddison et al., "Short hairpin RNAs (shRNAs) induce sequence-specific silencing in mammalian cells", Genes Dev., 16(8):948-958, doi: 10.1101/gad.981002, (Apr. 15, 2002).

(56) References Cited

OTHER PUBLICATIONS

Pasquinelli et al., "Conservation of the sequence and temporal expression of let-7 heterochronic regulatory RNA", Nature, 408(6808):86-89, doi: 10.1038/35040556, (Nov. 2, 2000).
Paul et al., "Effective expression of small interfering RNA in human cells", Nature Biotechnol., 20(5):505-508, doi: 10.1038/nbt0502-505, (May 2002).
Petersen et al., "LNA: a versatile tool for therapeutics and genomics", Trends Biotechnol., 21(2):74-81, doi: 10.1016/S0167-7799(02)00038-0, (Feb. 2003).
Reinhart et al., "Small RNAs correspond to centromere heterochromatic repeats", Science, 297(5588):1831, doi: 10.1126/science.1077183, (Aug. 22, 2002).
Rusckowski et al., "Biodistribution and metabolism of a mixed backbone oligonucleotide (GEM 231) following single and multiple dose administration in mice", Antisense Nucleic Acid Drug Dev.,10(5):333-345, doi: 10.1089/oli.1.2000.10.333, (Oct. 2000).
Sah, "Therapeutic potential of RNA interference for neurological disorders", Life Sciences, vol. 79, Issue 19, pp. 1773-1780, (Oct. 4, 2006).
Schwab et al., "An approach for new anticancer drugs: oncogene-targeted antisense DNA", Ann Oncol., 5 Suppl 4:55-58, doi: 10.1093/annonc/5.suppl_4.s55, (1994).
Soutschek et al., "Therapeutic silencing of an endogenous gene by systemic administration of modified siRNAs", Nature, 432(7014):173-178, doi: 10.1038/nature03121, (Nov. 11, 2004).
Stein et al., "Systemic and Central Nervous System Correction of Lysosomal Storage in Mucopolysaccharidosis Type VII Mice", J Virol, 73:3424-3429, (1999).
Sui et al., "A DNA vector-based RNAi technology to suppress gene expression in mammalian cells", Proc. Natl. Acad. Sci. USA, 99(8), 5515-5520, (Apr. 16, 2002).
The miRNA Registry at the Sanger Institute website, http://www.mirbase.org/.
Tuschl, "Expanding small RNA interference", Nat Biotechnol., 20(5):446-448, doi: 10.1038/nbt0502-446, (May 2002).
U.S. Appl. No. 60/762,225, entitled "Compositions and methods for enhancing discriminatory RNA interference", filed Jan. 25, 2006.
Wang et al., "Nanoparticle-based delivery system for application of siRNA in vivo", Curr Drug Metab., 11 (2):182-196, doi: 10.2174/138920010791110863, (Feb. 2010).
Wright et al., "Identification of Factors that Contribute to Recombinant AAV2 Particle Aggregation and Methods to Prevent Its Occurrence during Vector Purification and Formulation", Molecular Therapy, 12:171-178, (2005).
Yekta et al., "MicroRNA-directed cleavage of HOXB8 mRNA", Science, 304(5670):594-596, doi: 10.1126/science.1097434, (Apr. 23, 2004).
Yu et al., "RNA interference by expression of short-interfering RNAs and hairpin RNAs in mammalian cells", Proc. Natl. Acad. Sci. USA, 99(9), 6047-6052, (2002).
Yuan et al, "Recent advances of siRNA delivery by nanoparticles", Expert Opinion on Drug Delivery, vol. 8, No. 4, pp. 521-536, (2011).
Zeng et al., "Both natural and designed micro RNAs can inhibit the expression of cognate mRNAs when expressed in human cells", Mol. Cell, 9(6):1327-1333, doi: 10.1016/S1097-2765(02)00541-5, (Jun. 2002).
Zeng et al., "Sequence requirements for micro RNA processing and function in human cells", RNA, 9(1):112-123, doi: 10.1261/rna.2780503, (Jan. 2003).
Zou et al., "Liposome-mediated NGF gene transfection following neuronal injury: potential therapeutic applications", Gene Ther., 6(6):994-1005, doi: 10.1038/sj.gt.3300936, (Jun. 1999).
U.S. 16/833,107 2020/0385737, filed Mar. 27, 2020 Dec. 10, 2020, Anastasia Khvorova, Anti-C9ORF72 Oligonucleotides and Related Methods.
U.S. Appl. No. 16/868,237 2020/0385723, filed May 6, 2020 Dec. 10, 2020, Robert H. Brown, Oligonucleotide-Based Modulation of C9orf72.

* cited by examiner

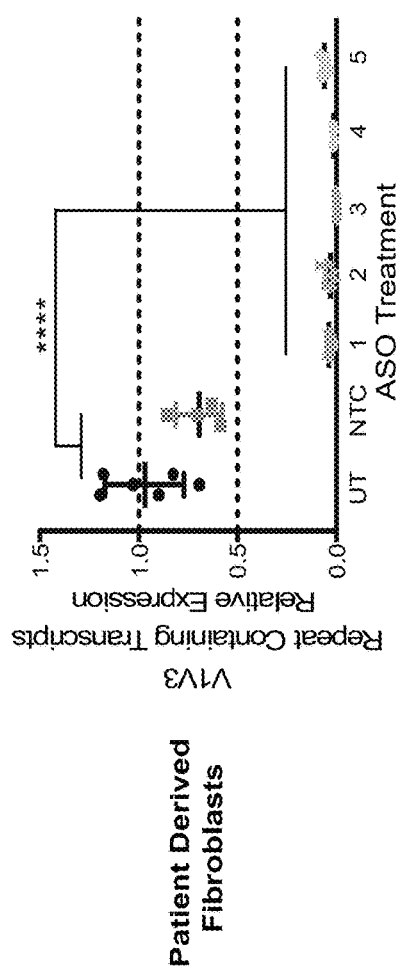
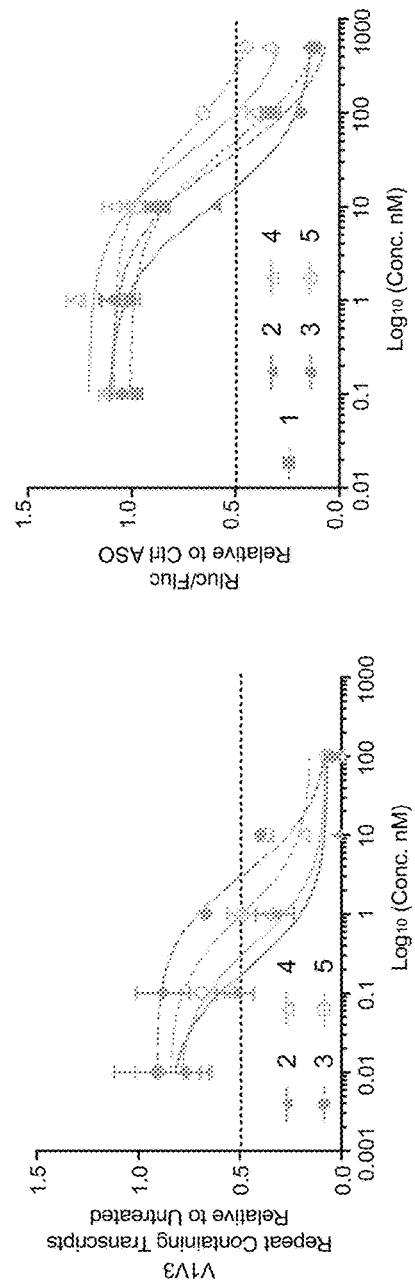
*Fig. 3A*
*Fig. 3B*

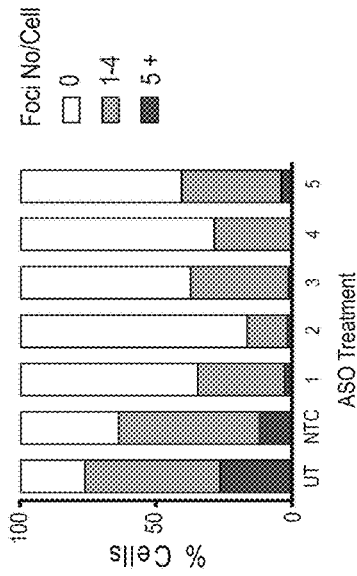
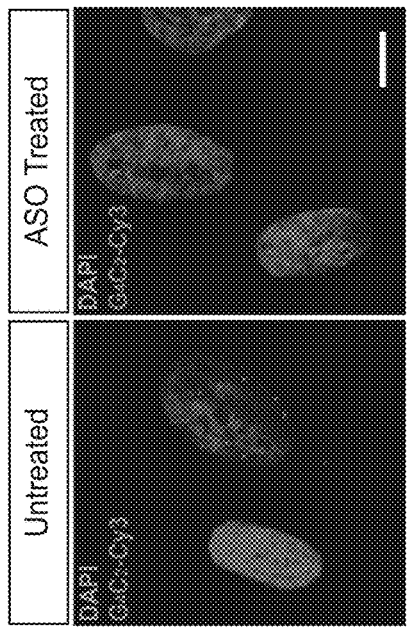
*Fig. 4A*
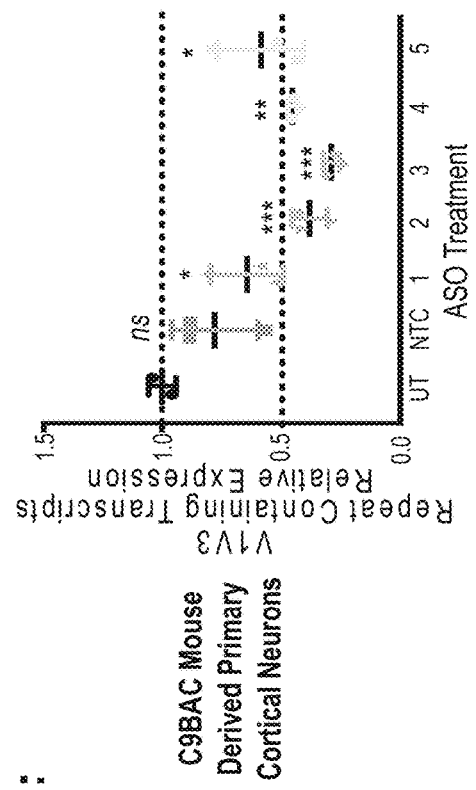
*Fig. 4B*

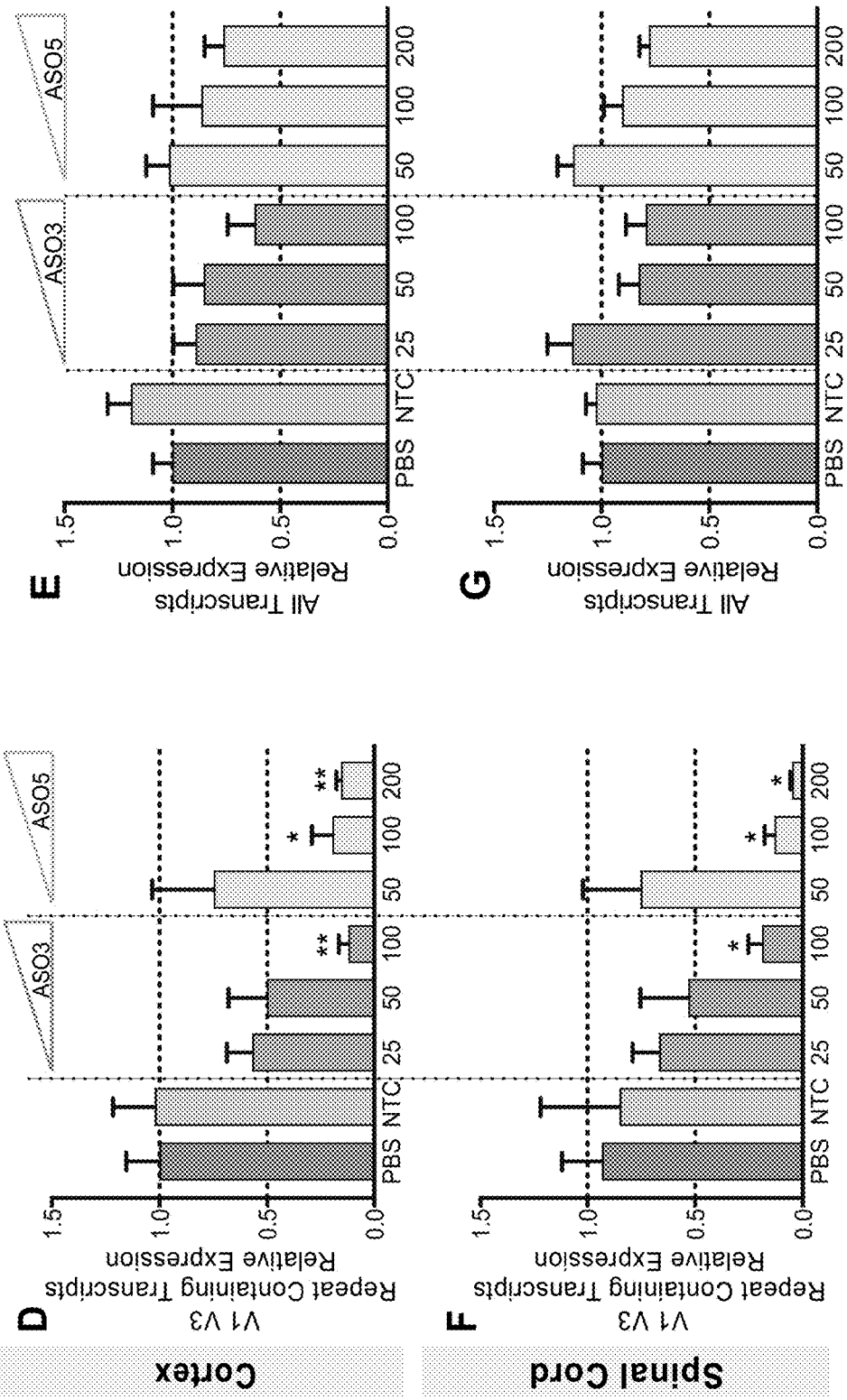

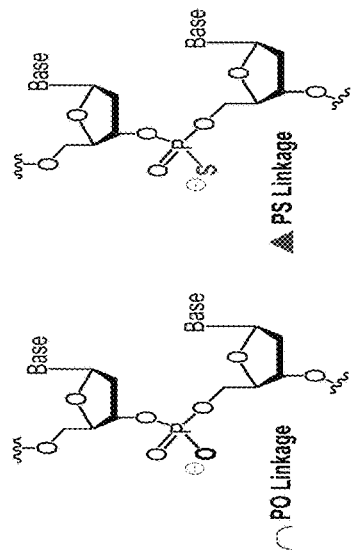
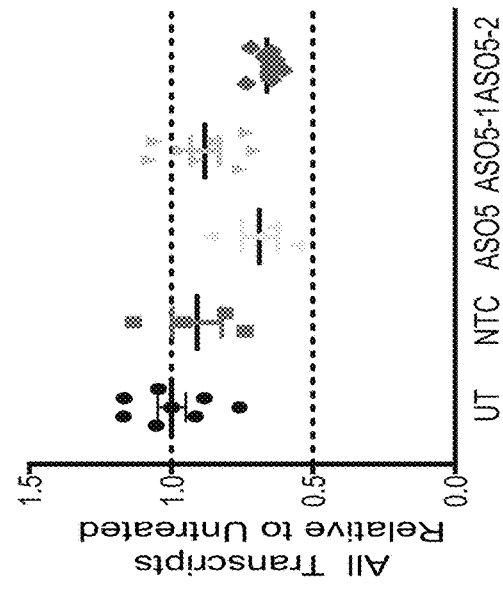
*Fig. 8A*
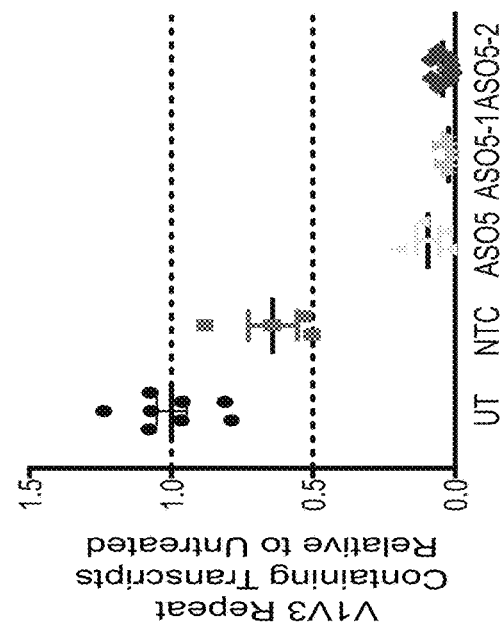
*Fig. 8B*

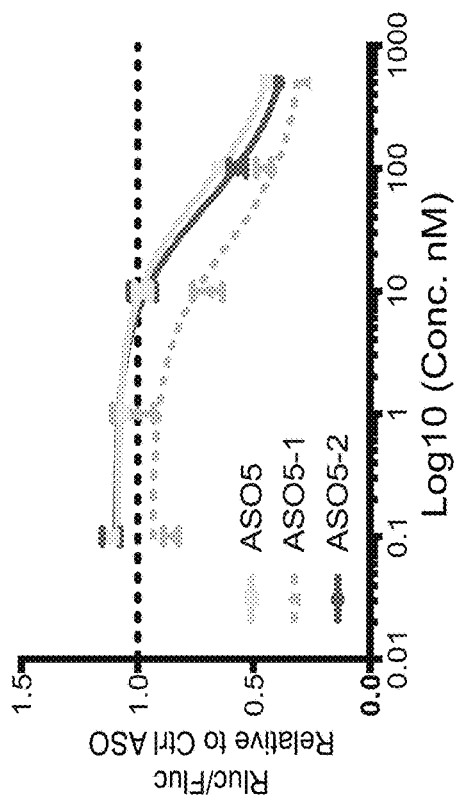
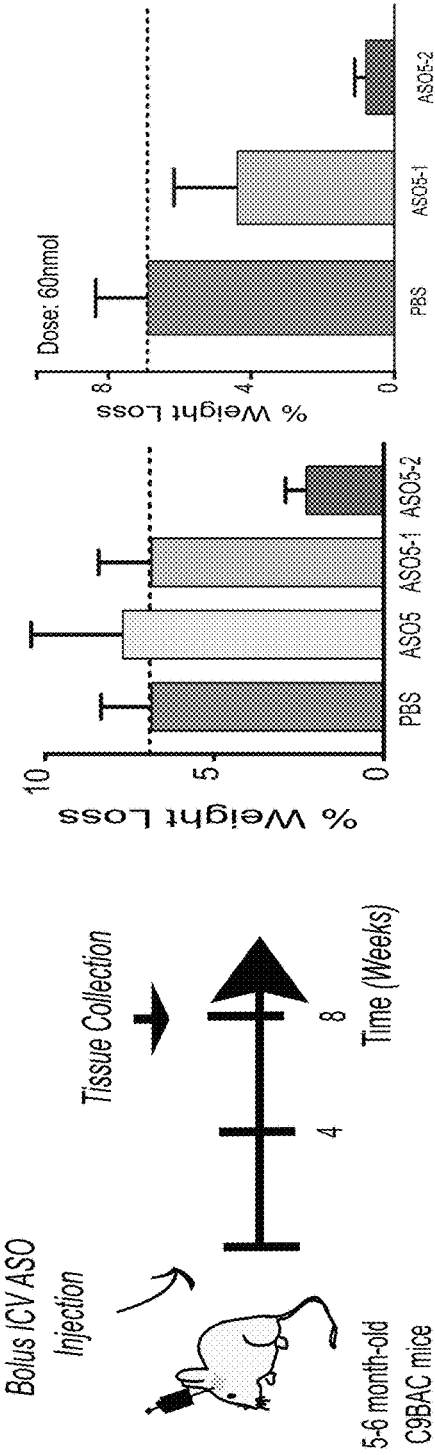
Fig. 9A
Fig. 9B

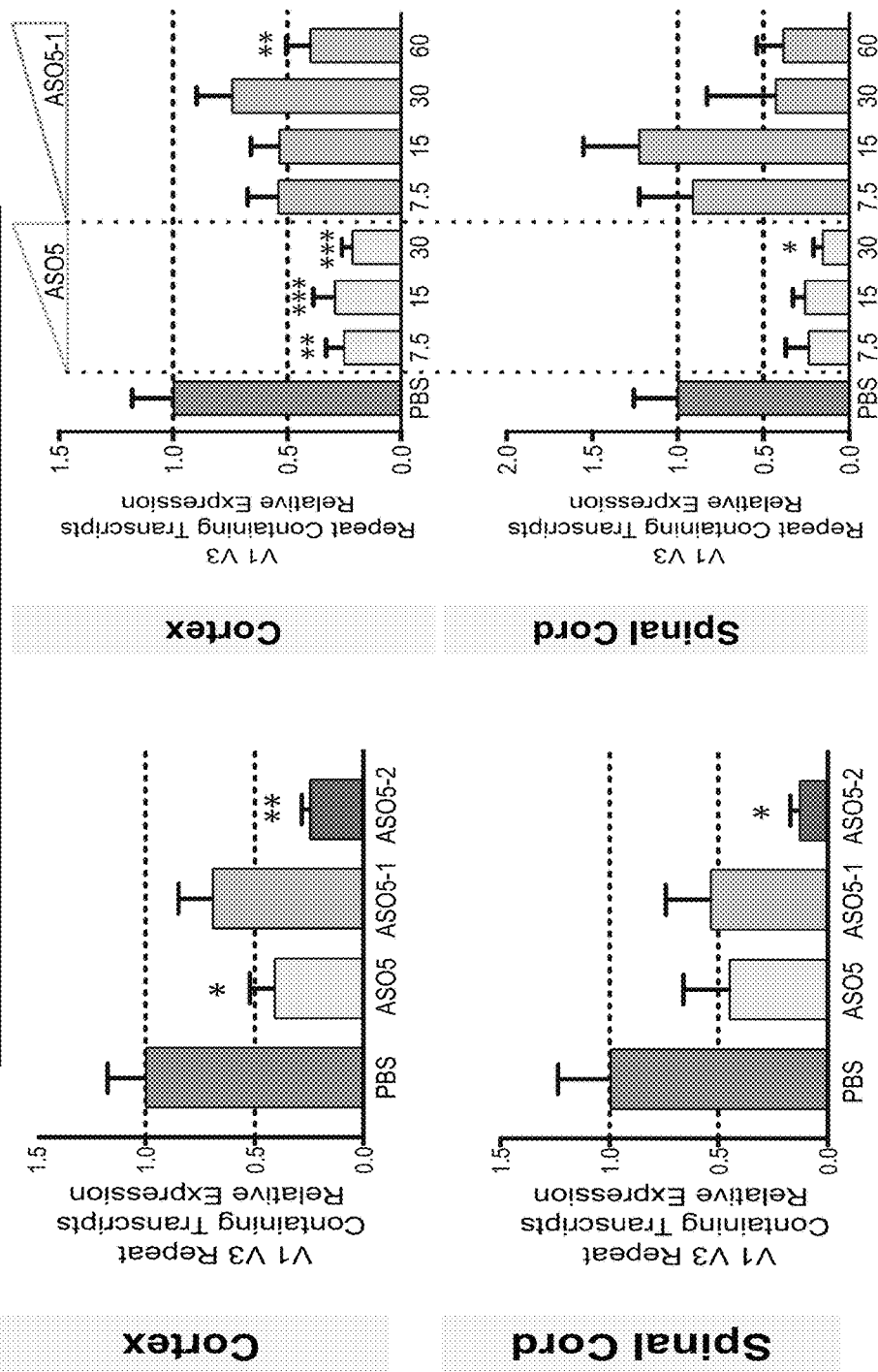

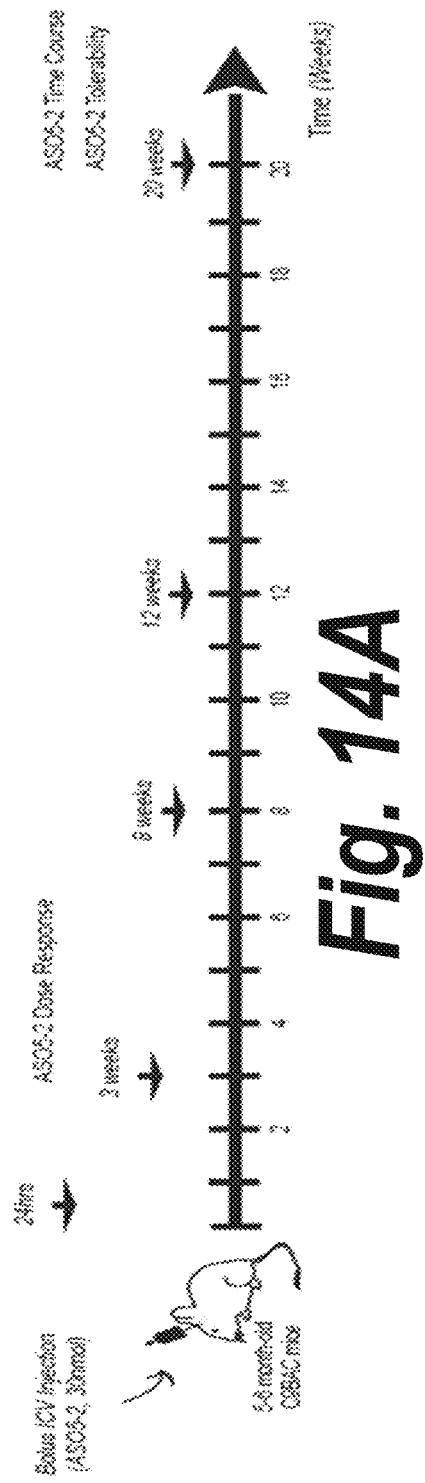
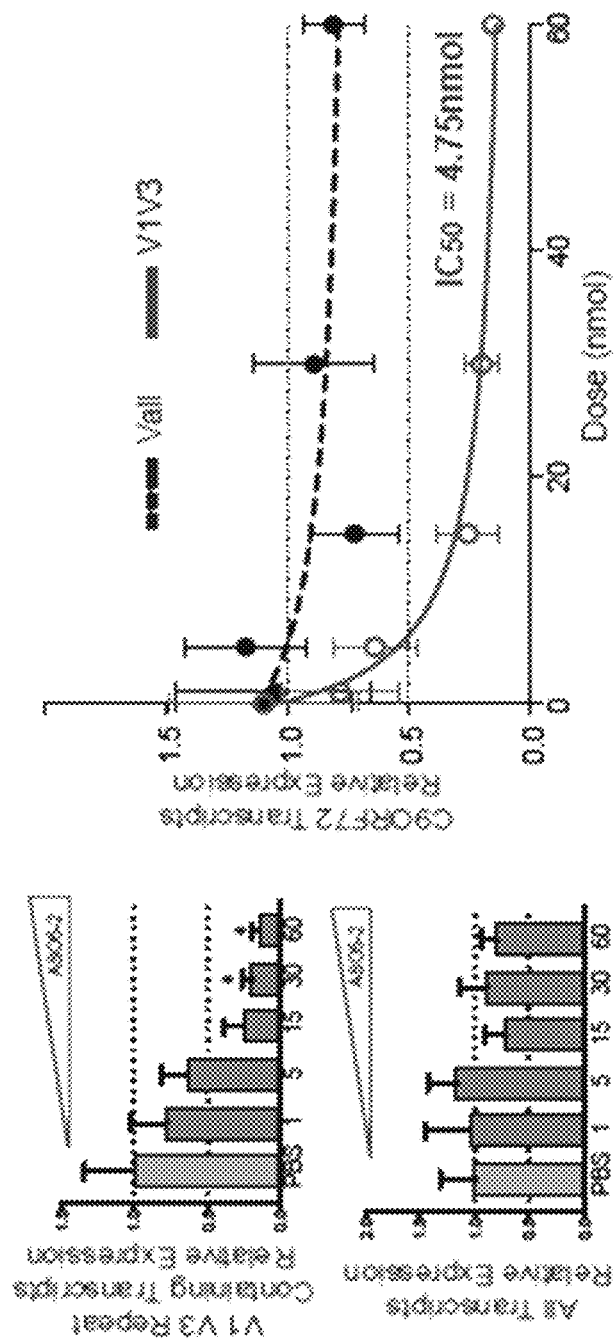
Fig. 14A
Fig. 14B

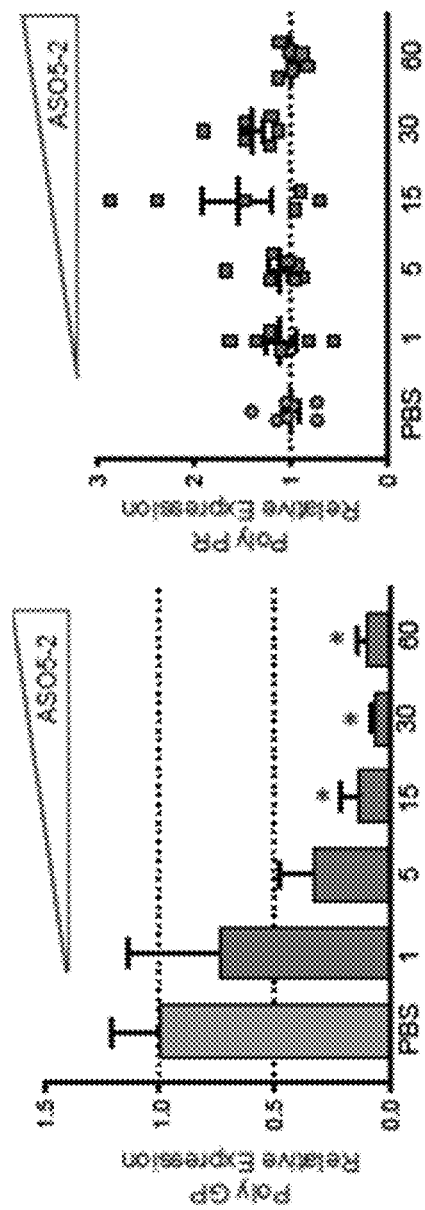
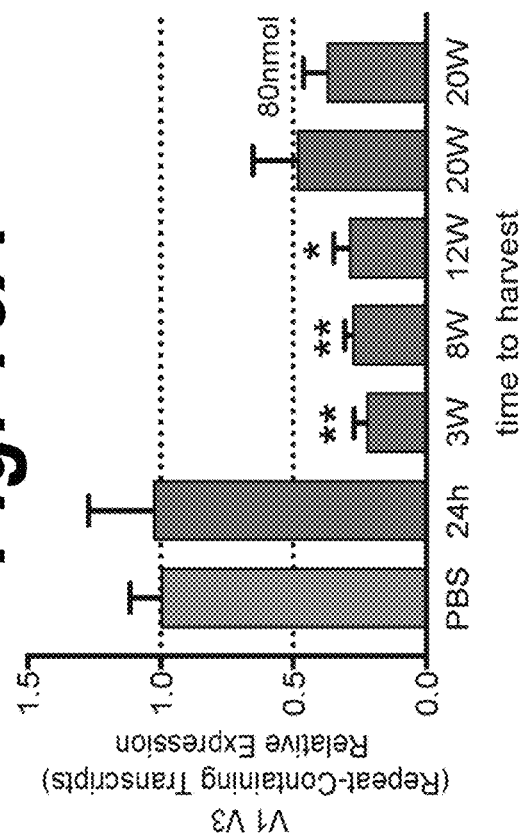
Fig. 15A
Fig. 15B

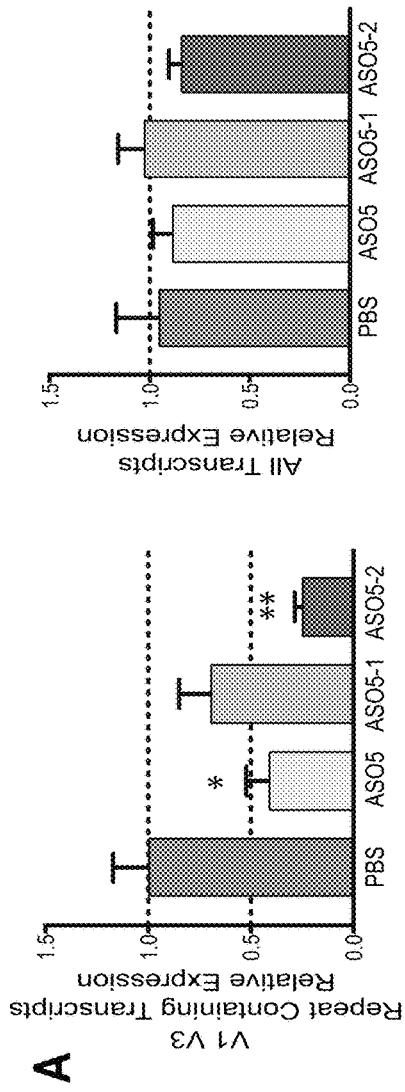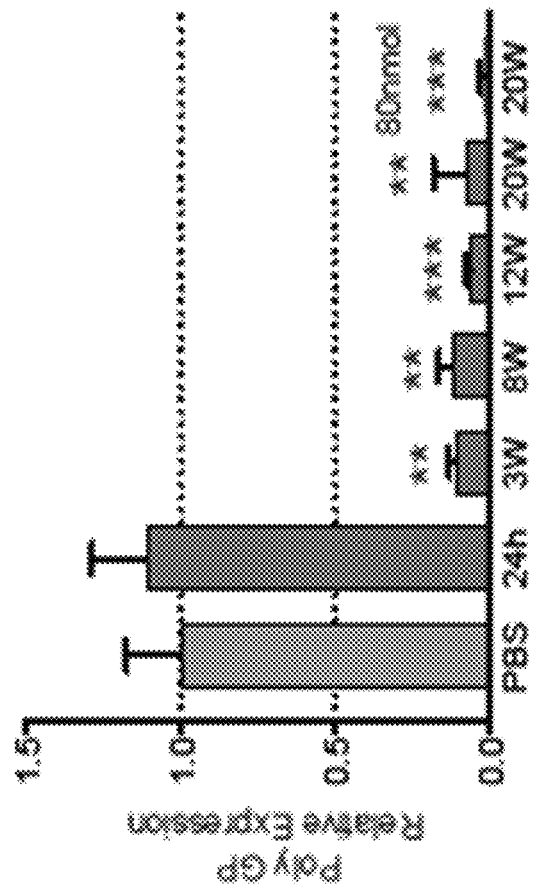
Fig. 16A
Fig. 16B

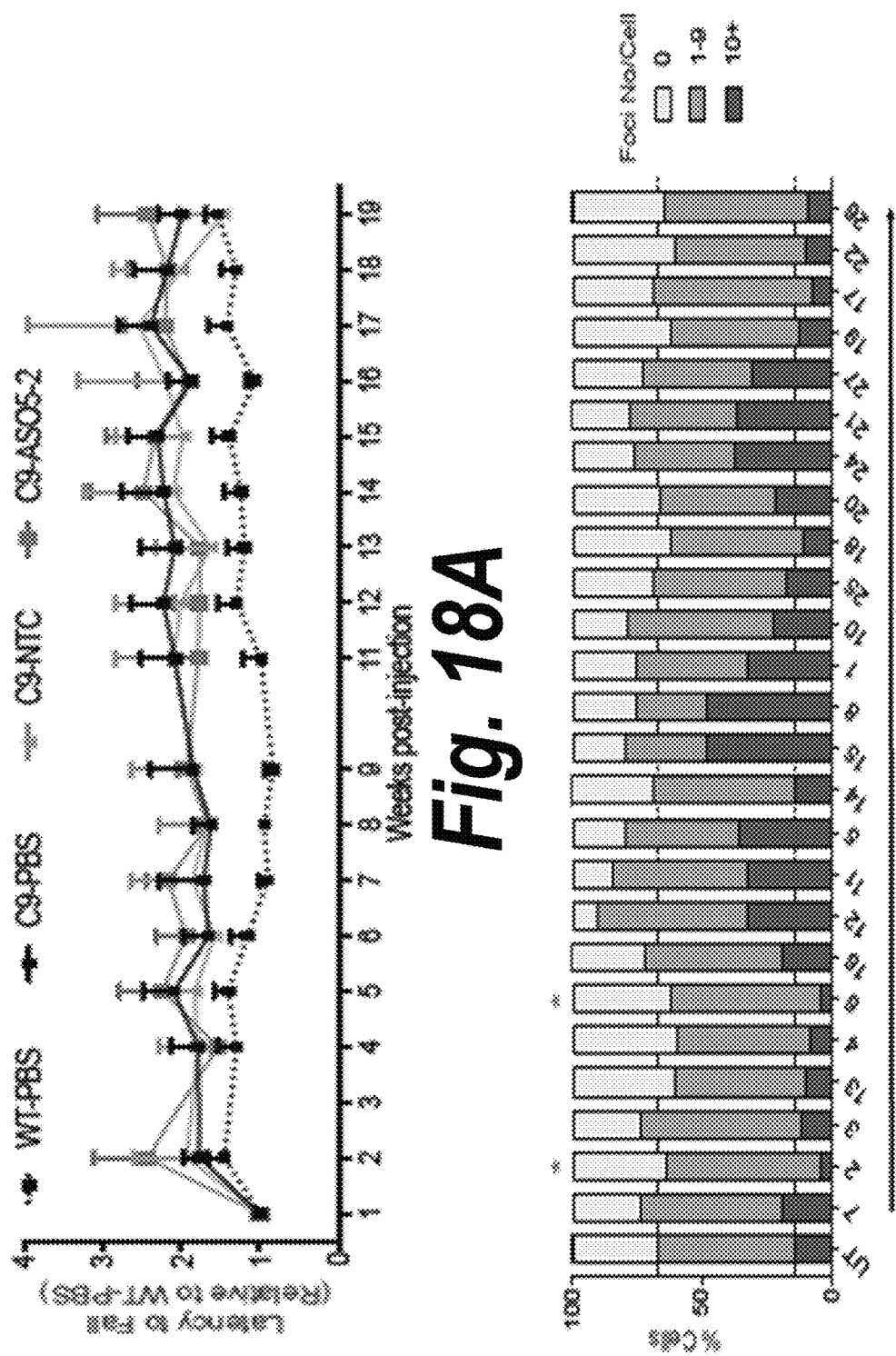

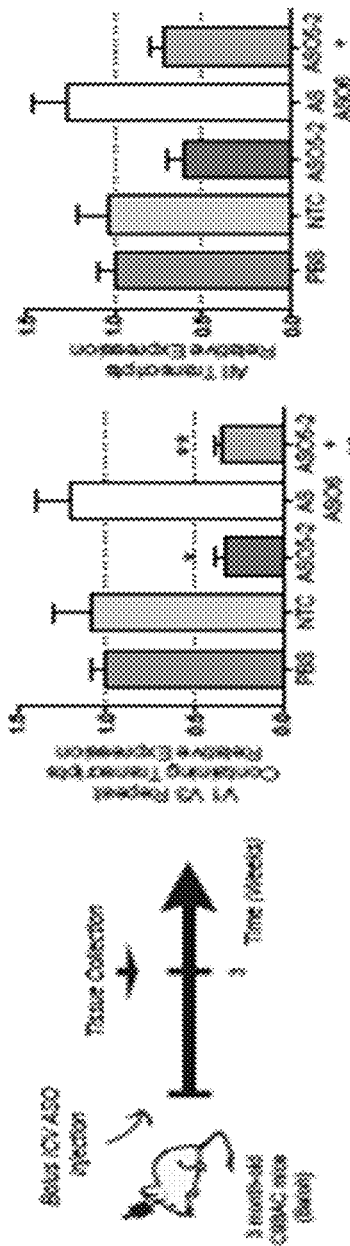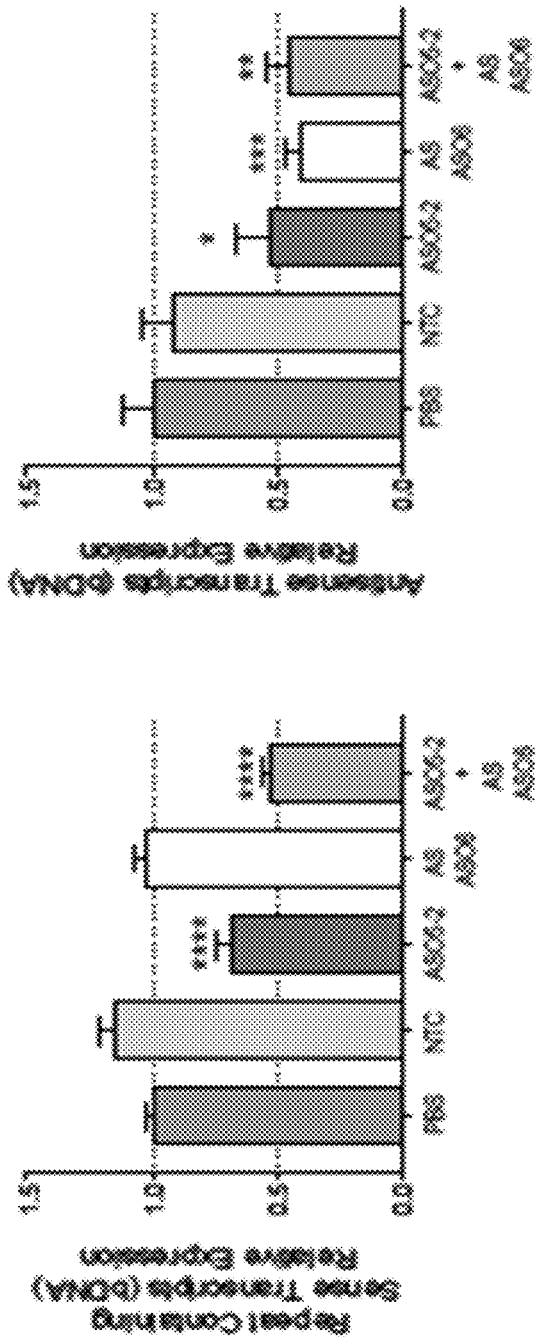
Fig. 19A
Fig. 19B

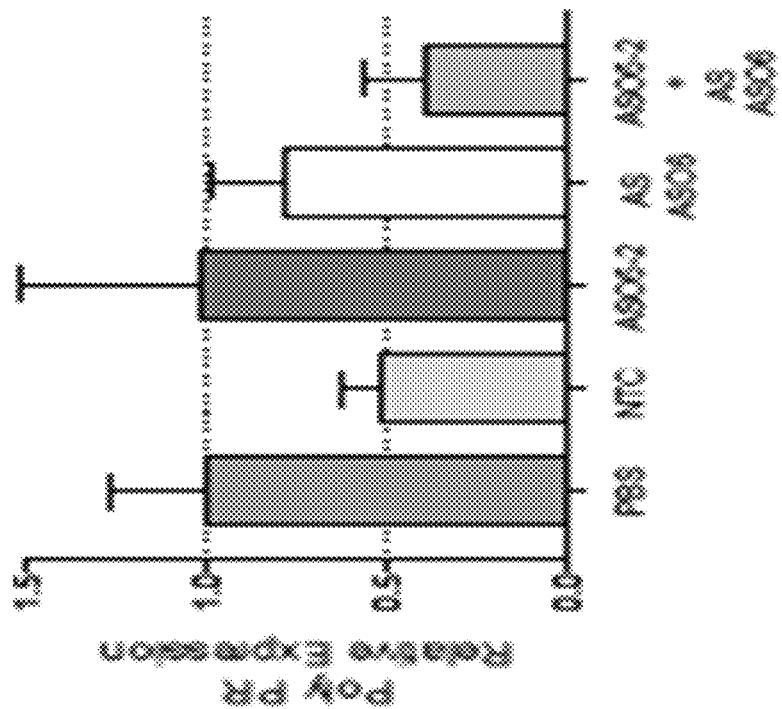
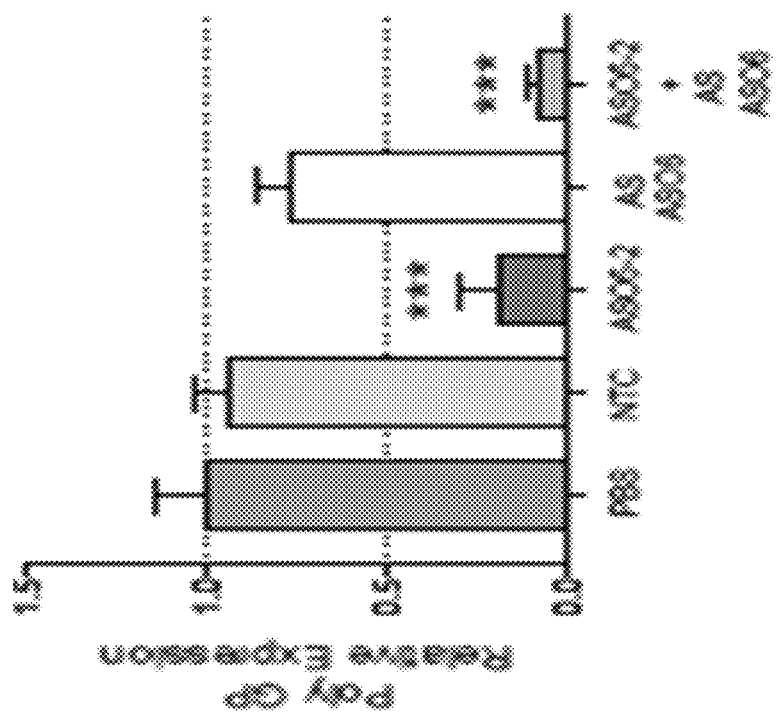
Fig. 20

ANTI-C9ORF72 OLIGONUCLEOTIDES AND RELATED METHODS

CROSS-REFERENCE TO RELATED APPLICATIONS

This application claims the benefit of U.S. Provisional Application Ser. No. 62/843,740, filed May 6, 2019, the entire disclosure of which is hereby incorporated herein by reference.

STATEMENT REGARDING FEDERALLY FUNDED RESEARCH

This invention was made with government support under Grant No. NS111990 awarded by the National Institutes of Health. The government has certain rights in this invention.

SEQUENCE LISTING

The instant application contains a Sequence Listing which has been submitted electronically in ASCII format and is hereby incorporated by reference in its entirety. Said ASCII copy, created on Aug. 20, 2020, is named 704934_UM9-239_ST25.txt and is 7 KB in size.

BACKGROUND

Amyotrophic lateral sclerosis (ALS) is a progressive, uniformly lethal motor neuron disease that starts with focal weakness and leads to nearly complete paralysis and death, typically in 3-4 years. About 10% of cases are familial (FALS). The most common cause of FALS is an expansion of a six-nucleotide repeat motif in the first intron of the gene C9ORF72. While normal individuals have less than 30 of these $C_4G_2$ repeats, some individuals with ALS harbor hundreds or even thousands of these repeats. Expression of the C9ORF72 gene involves three pre-mRNA sense transcripts (V1, V2, V3). Two of these, V1 and V3, encompass the expanded hexanucleotide repeat, while the V2 does not. There is also an antisense transcript expressed from the C9ORF72 gene that includes the antisense expanded repeat.

This intronic expansion may not only contribute to ALS but also fronto-temporal dementia (FTD); these disorders may occur independently or together. The C9ORF72 expansions may also contribute to other neurological phenotypes. In the United States, about 40% of cases of FALS are caused by the C9ORF72 expansions. Why the expansions are toxic is not clear. Possible mechanisms include: (1) reduced expression of the C9ORF72 gene; (2) formation of aggregates of the expanded repeat segments, usually within the nucleus (RNA foci); (3) disruption of normal gradients across the nuclear membrane of neurons and other cell types; and (4) translation of the expanded hexanucleotide motif in all possible reading frames, leading to detectable levels of potentially toxic species of five different poly-dipeptides, including glycine-proline dipeptide repeat protein (GP dipeptide repeat protein) and arginine-proline dipeptide repeat protein (PR dipeptide repeat protein). Crucially, these repeat dipeptides are expressed from both the sense and antisense transcripts. There exists a need in the art to effectively silence or inhibit the expression or activity of the toxic C9ORF72 sense and antisense transcripts, as well as the dipeptide repeat proteins derived from the C9ORF72 sense and antisense transcripts.

SUMMARY

In one aspect, the disclosure provides an antisense oligonucleotide comprising a region of complementarity to a C9ORF72 antisense transcript sequence of 5' GAA-AGUAAAAAU GCGUCGAG 3' (SEQ ID NO:1), 5' CUC-CUUGUUUUCUUCUGGUU 3' (SEQ ID NO: 2), 5' CAG-GUCUUUUCUUGUUCACC 3' (SEQ ID NO: 3), or 5' CCUCCUUGUUUUCUUCUGGU 3' (SEQ ID NO: 4). In an embodiment, the antisense oligonucleotide comprises 8 to 80 nucleotides in length. In another embodiment, the antisense oligonucleotide comprises 10 to 30 nucleotides in length.

The antisense oligonucleotide may comprise one or more modified nucleotides. In an embodiment, the one or more modified nucleotides each independently comprise a modification of a ribose group, a phosphate group, a nucleobase, or a combination thereof.

Each modification of the ribose group may be independently selected from the group consisting of 2'-O-methyl, 2'-fluoro, 2'-H, 2'-O-(2-methoxyethyl) (MOE), 2'-O-alkyl, 2'-O-alkoxy, 2'-O-alkylamino, 2'-NH$_2$, or a constrained nucleotide. The constrained oligonucleotide may be a locked nucleic acid (LNA), an ethyl-constrained nucleotide, a 2'-(S)-constrained ethyl (S-cEt) nucleotide, a constrained MOE, a 2'-O,4'-C-aminomethylene bridged nucleic acid (2',4'-BNA$^{NC}$), an alpha-L-locked nucleic acid, a tricyclo-DNA, or any combination thereof. In an embodiment, the modification of the ribose group is 2'-O-(2-methoxyethyl) (MOE).

Each modification of the phosphate group may be independently selected from the group consisting of a phosphorothioate, phosphonoacetate (PACE), thiophosphonoacetate (thioPACE), amide, triazole, phosphonate, or phosphotriester modification. In an embodiment, the modification of the phosphate group is phosphorothioate.

Each modification of the nucleobase group may be 2-thiouridine, 4-thiouridine, N$^6$-methyladenosine, pseudouridine, 2,6-diaminopurine, inosine, thymidine, 5-methylcytosine, 5-substituted pyrimidine, isoguanine, isocytosine, or halogenated aromatic groups. In an embodiment, the modification of the nucleobase group is 5-methylcytosine.

In representative embodiments, the antisense nucleotide comprises the formula A-B-C, wherein: A comprises from about 0 to about 8 modified nucleotides; B comprises from about 4 to about 18 deoxyribonucleic acid (DNA) nucleotides and/or DNA-like nucleotides; and C comprises from about 0 to about 8 modified nucleotides; and the overall length of the antisense oligonucleotide is about 10 to about 30 nucleotides. In an embodiment, A comprises from about 2 to about 6 modified nucleotides, B comprises from about 6 to about 12 DNA nucleotides and/or DNA-like nucleotides, and C comprises from about 2 to about 6 modified nucleotides. In another embodiment, A comprises about 5 modified nucleotides, B comprises about 8 DNA nucleotides and/or DNA-like nucleotides, and C comprises about 5 modified nucleotides. In a further embodiment, A comprises from about 2 to about 6 2'-O-(2-methoxyethyl) (MOE) modified nucleotides, B comprises from about 6 to about 12 DNA-like nucleotides, and C comprises from about 2 to about 6 locked 2'-O-(2-methoxyethyl) (MOE) modified nucleotides. In another further embodiment, A comprises about 5 2'-O-(2-methoxyethyl) (MOE) modified nucleotides, B comprises about 8 DNA-like nucleotides, and C comprises about 5 locked 2'-O-(2-methoxyethyl) (MOE) modified nucleotides. In an additional embodiment, A comprises about 5 2'-O-(2-methoxyethyl) (MOE) modified nucleotides, B comprises about 10 DNA-like nucleotides, and C comprises about 5 locked 2'-O-(2-methoxyethyl) (MOE) modified nucleotides.

In an exemplary embodiment, the antisense oligonucleotide is conjugated to a ligand. In another embodiment, the antisense oligonucleotide comprises a nucleic acid sequence with at least 90% sequence identity to the nucleic acid sequence set forth in any one of SEQ ID NOs: 5-8 (SEQ ID NO: 5—CTCGACGCATT~ITrACTTTC), (SEQ ID NO: 6—AACCAGAAG AAAACAAGGAG), (SEQ ID NO: 7—GGTGAACAAGAAAAGACCTG), (SEQ ID NO: 8—ACCAGAAGAAAACAAGGAGG). In a further embodiment, the antisense oligonucleotide comprises a sequence modification pattern of $\underline{X}_sX_oX_oX_oX_sX_sX_sX_sX_sX_sX_sX_sX_sX_sX_s\underline{X}_oX_oX_oX_sX$, wherein s represents a phosphorothioate internucleotide linkage; o represents a phosphodiester internucleotide linkage; and X is an adenosine, a guanosine, a cytidine, or a thymine comprising a 2'-O-(2-methoxyethyl) modification, and each cytosine may be a 5-methylcytosine.

In a second aspect, the disclosure provides an antisense nucleotide comprising the sequence $\underline{C}_s\underline{T}_s\underline{C}_o\underline{G}_o\underline{A}_s\underline{C}_s\underline{G}_s\underline{C}_s\underline{A}_sT_sT_sT_sT_sT_s\underline{A}_s\underline{C}_o\underline{T}_o\underline{T}_o\underline{T}_s\underline{C}$ (SEQ ID NO: 12), wherein s represents a phosphorothioate internucleotide linkage; o represents a phosphodiester internucleotide linkage; $\underline{A}$ is an adenosine comprising a 2'-O-(2-methoxyethyl) modification; $\underline{G}$ is a guanosine comprising a 2'-O-(2-methoxyethyl) modification; $\underline{C}$ is a cytidine comprising a 2'-O-(2-methoxyethyl) modification; $\underline{T}$ is a thymine comprising a 2'-O-(2-methoxyethyl) modification; and each cytosine is a 5-methylcytosine.

In a third aspect, the disclosure provides an antisense oligonucleotide comprising a region of complementarity to a C9ORF72 sense transcript sequence of 5' GAGUCGCGCGCUA GGGGC 3' (SEQ ID NO: 9), wherein the antisense oligonucleotide comprises internucleotide linkages from 5' to 3' of sooossssssssssooos, wherein each s is a phosphorothioate linkage and each o is a phosphodiester linkage. In an embodiment, the antisense oligonucleotide comprises 18 to 80 nucleotides in length. In a further embodiment, the antisense oligonucleotide comprises 18 to 30 nucleotides in length.

The antisense oligonucleotide may comprise one or more modified nucleotides. The one or more modified nucleotides may each independently comprise a modification of a ribose group, a modification of a phosphate group, a modification of a nucleobase, or a combination thereof.

In an embodiment, each modification of the ribose group is independently selected from the group consisting of 2'-O-methyl, 2'-fluoro, 2'-, 2'-O-(2-methoxyethyl)(MOE), 2'-O-alkyl, 2'-O-alkoxy, 2'-O-alkylamino, 2'-NH$_2$, or a bicyclic nucleotide. The bicyclic nucleotide may be selected from the group consisting of a locked nucleic acid (LNA), an ethyl-constrained nucleotide, AN 2'-(S)-constrained ethyl (S-cEt) nucleotide, a constrained MOE, a 2'-0,4'-C-aminomethylene bridged nucleic acid (2',4'-BNA$^{NC}$), an alpha-L-locked nucleic acid, and a tricyclo-DNA, or any combination thereof. In an embodiment, the modification of the ribose group is 2'-O-(2-methoxyethyl) (MOE).

In a further embodiment, each modification of the phosphate group may be a phosphorothioate, phosphonoacetate (PACE), thiophosphonoacetate (thioPACE), amide, triazole, phosphonate, or phosphotriester modification.

In an additional embodiment, each modification of the nucleobase group may be 2-thiouridine, 4-thiouridine, N$^6$-methyladenosine, pseudouridine, 2,6-diaminopurine, inosine, thymidine, 5-methylcytosine, 5-substituted pyrimidine, isoguanine, isocytosine, or halogenated aromatic groups.

In representative embodiments, the antisense nucleotide comprises the formula A-B-C, wherein: A comprises from about 0 to about 8 modified nucleotides; B comprises from about 4 to about 18 deoxyribonucleic acid (DNA) nucleotides and/or DNA-like nucleotides; and C comprises from about 0 to about 8 modified nucleotides; and the overall length of the antisense oligonucleotide is about 10 to about 30 nucleotides. In an embodiment, A comprises from about 2 to about 6 modified nucleotides, B comprises from about 6 to about 12 DNA nucleotides and/or DNA-like nucleotides, and C comprises from about 2 to about 6 modified nucleotides. In another embodiment, A comprises about 5 modified nucleotides, B comprises about 8 DNA nucleotides and/or DNA-like nucleotides, and C comprises about 5 modified nucleotides. In a further embodiment, A comprises from about 2 to about 6 2'-O-(2-methoxyethyl) (MOE) modified nucleotides, B comprises from about 6 to about 12 DNA-like nucleotides, and C comprises from about 2 to about 6 locked 2'-O-(2-methoxyethyl) (MOE) modified nucleotides. In another further embodiment, A comprises about 5 2'-O-(2-methoxyethyl) (MOE) modified nucleotides, B comprises about 8 DNA-like nucleotides, and C comprises about 5 locked 2'-O-(2-methoxyethyl) (MOE) modified nucleotides. In an additional embodiment, A comprises about 5 2'-O-(2-methoxyethyl) (MOE) modified nucleotides, B comprises about 10 DNA-like nucleotides, and C comprises about 5 locked 2'-O-(2-methoxyethyl) (MOE) modified nucleotides.

In an exemplary embodiment, the antisense oligonucleotide is conjugated to a ligand. In another embodiment, the antisense oligonucleotide comprises a nucleic acid sequence with at least 90% sequence identity to the nucleic acid sequence set forth in SEQ ID NO: 10 (SEQ ID NO: 10—GCCCCTAGCGCGCGACTC). In a further embodiment, the antisense oligonucleotide comprises a sequence modification pattern of $\underline{X}_sX_oX_oX_oX_sX_sX_sX_sX_sX_sX_sX_sX_sX_s\underline{X}_o\underline{X}_o\underline{X}_sX$ wherein s represents a phosphorothioate internucleotide linkage; o represents a phosphodiester internucleotide linkage; and $\underline{X}$ is an adenosine, a guanosine, a cytidine, or a thymine comprising a 2'-O-(2-methoxyethyl) modification, and each cytosine may be a 5-methylcytosine.

In a fourth aspect, the disclosure provides an antisense oligonucleotide comprising the sequence $\underline{G}_s\underline{C}_o\underline{C}_o\underline{C}_o\underline{C}_sT_s\underline{A}_s\underline{G}_s\underline{C}_s\underline{G}_s\underline{C}_s\underline{G}_s\underline{C}_s\underline{G}_o\underline{A}_o\underline{C}_o\underline{T}_s\underline{C}$ (SEQ ID NO: 16), wherein s represents a phosphorothioate internucleotide linkage; o represents a phosphodiester internucleotide linkage; $\underline{A}$ is an adenosine comprising a 2'-O-(2-methoxyethyl) modification; $\underline{G}$ is a guanosine comprising a 2'-O-(2-methoxyethyl) modification; $\underline{C}$ is a cytidine comprising a 2'-O-(2-methoxyethyl) modification; $\underline{T}$ is a thymine comprising a 2'-O-(2-methoxyethyl) modification; and each cytosine is a 5-methylcytosine.

In a fifth aspect, there is provided a combination comprising one or more antisense oligonucleotides comprising a region of complementarity to a C9ORF72 antisense transcript sequence and one or more antisense oligonucleotides comprising a region of complementarity to a C9ORF72 sense transcript sequence.

In an embodiment, the antisense oligonucleotide comprises a region of complementarity to a C9ORF72 antisense transcript sequence of 5' GAAAGUAAAAAUGCGUCGAG 3' (SEQ ID NO:1), 5' CUCCUUGUUUUCUUCUGGUU 3' (SEQ ID NO: 2), 5' CAGGUCUUUUCUUGUU CACC 3' (SEQ ID NO: 3), or 5' CCUCCUUGUUUUC-UUCUGGU 3' (SEQ ID NO: 4). In a further embodiment, the antisense oligonucleotide comprises a region of complementarity to a C9ORF72 sense transcript sequence of 5'

GAGTCGCGCGCTAGGGGC 3' (SEQ ID NO: 9). In an embodiment, the one or more antisense oligonucleotides comprise 8 to 80 nucleotides in length. In a further embodiment, the one or more antisense oligonucleotides comprise 10 to 30 nucleotides in length.

The one or more antisense oligonucleotides of the combination may comprise one or more modified nucleotides. In an embodiment, the one or more modified nucleotides each independently comprise a modification of a ribose group, a phosphate group, a nucleobase, or a combination thereof.

Each modification of the ribose group may be 2'-O-methyl, 2'-fluoro, 2'-H, 2'-O-(2-methoxyethyl) (MOE), 2'-O-alkyl, 2'-O-alkoxy, 2'-O-alkylamino, 2'-NH$_2$, or a constrained nucleotide. The constrained oligonucleotide may be a locked nucleic acid (LNA), an ethyl-constrained nucleotide, a 2'-(S)-constrained ethyl (S-cEt) nucleotide, a constrained MOE, a 2'-O,4'-C-aminomethylene bridged nucleic acid (2',4'-BNA$^{NC}$), an alpha-L-locked nucleic acid, a tricyclo-DNA, or any combination thereof. In an embodiment, the modification of the ribose group is 2'-O-(2-methoxyethyl) (MOE).

Each modification of the phosphate group may be a phosphorothioate, phosphonoacetate (PACE), thiophosphonoacetate (thioPACE), amide, triazole, phosphonate, or phosphotriester modification. In an embodiment, the modification of the phosphate group is phosphorothioate.

Each modification of the nucleobase group 2-thiouridine, 4-thiouridine, N$^6$-methyladenosine, pseudouridine, 2,6-diaminopurine, inosine, thymidine, 5-methylcytosine, 5-substituted pyrimidine, isoguanine, isocytosine, or halogenated aromatic groups. In an embodiment, the modification of the nucleobase group is 5-methylcytosine.

In representative embodiments, the combination comprises the formula A-B-C, wherein: A comprises from about 0 to about 8 modified nucleotides; B comprises from about 4 to about 18 deoxyribonucleic acid (DNA) nucleotides and/or DNA-like nucleotides; and C comprises from about 0 to about 8 modified nucleotides; and the overall length of the antisense oligonucleotide is about 10 to about 30 nucleotides. In an embodiment, A comprises from about 2 to about 6 modified nucleotides, B comprises from about 6 to about 12 DNA nucleotides and/or DNA-like nucleotides, and C comprises from about 2 to about 6 modified nucleotides. In another embodiment, A comprises about 5 modified nucleotides, B comprises about 8 DNA nucleotides and/or DNA-like nucleotides, and C comprises about 5 modified nucleotides. In a further embodiment, A comprises from about 2 to about 6 2'-O-(2-methoxyethyl) (MOE) modified nucleotides, B comprises from about 6 to about 12 DNA-like nucleotides, and C comprises from about 2 to about 6 locked 2'-O-(2-methoxyethyl) (MOE) modified nucleotides. In another further embodiment, A comprises about 5 2'-O-(2-methoxyethyl) (MOE) modified nucleotides, B comprises about 8 DNA-like nucleotides, and C comprises about 5 locked 2'-O-(2-methoxyethyl)(MOE) modified nucleotides. In an additional embodiment, A comprises about 5 2'-O-(2-methoxyethyl) (MOE) modified nucleotides, B comprises about 10 DNA-like nucleotides, and C comprises about 5 locked 2'-O-(2-methoxyethyl) (MOE) modified nucleotides.

In an exemplary embodiment, the antisense oligonucleotide is conjugated to a ligand. In another embodiment, the combination comprises a nucleic acid sequence with at least 90% sequence identity to the nucleic acid sequence set forth in SEQ ID NO: 10 (SEQ ID NO: 10—GCCCCTAGCGCGCGACTC). In a further embodiment, the combination comprises a sequence modification pattern of $\underline{X_sX_oX_oX_oX_sX_sX_sX_sX_sX_sX_sX_sX_sX_sX_oX_oX_oX_oX}$ wherein s represents a phosphorothioate internucleotide linkage; o represents a phosphodiester internucleotide linkage; and $\underline{X}$ is an adenosine, a guanosine, a cytidine, or a thymine comprising a 2'-O-(2-methoxyethyl) modification, and each cytosine may be a 5-methylcytosine.

In an embodiment, two or more antisense oligonucleotides of the combination are linked together through a linker. The linker may be a cleavable linker, for example a cleavable linker that degrades when cleaved. In an embodiment, the cleavable linker is a nuclease-cleavable linker comprising a phosphodiester linkage. The cleavable linker may comprise from about 2 to about 8 nucleotides, for example about 6 nucleotides. In exemplary embodiments, the cleavable linker is cleaved under reducing conditions or changing pH conditions. In a further embodiment, the cleavable linker is cleaved by an intracellular or endosomal nuclease. In an additional embodiment, the cleavable linker is cleaved by an intracellular or endosomal protease.

In a sixth aspect, there is provided a method for inhibiting expression of C9ORF72 gene in a cell, the method comprising: (a) introducing into the cell a suitable antisense oligonucleotide of any of the above embodiments; and (b) maintaining the cell produced in step (a) for a time sufficient to obtain degradation of the transcript of the C9ORF72 gene, thereby inhibiting expression of the C9ORF72 gene in the cell.

In a seventh aspect, there is provided a method of treating or managing Amyotrophic Lateral Sclerosis (ALS) comprising administering to a patient in need of such treatment or management a therapeutically effective amount of a suitable antisense oligonucleotide of any of the above embodiments. The antisense oligonucleotide may be administered to the brain of the patient. Example methods of administration include intrathecal, intraventricular or intrastriatal injection or infusion, for example by using an Ommaya reservoir or intrathecal catheter. In certain embodiments, the antisense oligonucleotide is administered at a dose of between about 0.5 mg/mL to about 5.0 mg/mL.

In an eight aspect, there is provided a method for inhibiting expression of C9ORF72 gene in a cell, the method comprising: (a) introducing into the cell a suitable combination of antisense oligonucleotides of any of the above embodiments; and (b) maintaining the cell produced in step (a) for a time sufficient to obtain degradation of the sense and antisense transcripts of the C9ORF72 gene, thereby inhibiting expression of the C9ORF72 gene in the cell.

In a ninth aspect, there is provided a method of treating or managing Amyotrophic Lateral Sclerosis (ALS) comprising administering to a patient in need of such treatment or management a therapeutically effective amount of a suitable combination of antisense oligonucleotides of any of the above embodiments. The antisense oligonucleotide may be administered to the brain of the patient. Example methods of administration include intrathecal, intraventricular or intrastriatal injection or infusion, for example by using an Ommaya reservoir or intrathecal catheter. The antisense oligonucleotides of the combination may be administered sequentially or simultaneously.

In a tenth aspect, there is provided a method of reducing the level of a dipeptide repeat protein in a patient, comprising administering to a patient in need of such reduction a therapeutically effective amount of the antisense oligonucleotide of any of the above embodiments. In certain embodiments, the antisense oligonucleotide is administered to the brain of the patient. In certain embodiments, the antisense oligonucleotide is administered by intrathecal, intraventricular or intrastriatal injection or infusion. In certain embodiments, the injection or infusion comprises administration using an Ommaya reservoir or intrathecal catheter. In certain embodiments, the dipeptide repeat protein comprises one or more of poly(GP), poly(GR), poly(GA), poly(PA), and poly (PR). In certain embodiments, the dipeptide repeat protein is poly(GP).

BRIEF DESCRIPTION OF THE DRAWINGS

The foregoing and other features and advantages of the present invention will be more fully understood from the following detailed description of illustrative embodiments taken in conjunction with the accompanying drawings.

FIG. 3A depicts that both LNA and 2'-O-MOE ASOs significantly reduce the level of repeat containing transcripts at a dose of 100 nM 72 h after lipid-mediated delivery in patient derived fibroblasts as measured by qRT-PCR.

FIG. 3B depicts dose response of ASOs in patient-derived fibroblasts (left panel) and HEK293 cells transfected with the C9Luc reporter assay (right panel). Data are plotted from a 5-point non-linear fit dose response curve.

FIG. 4A depicts representative images of RNA foci visualized by FISH in patient derived fibroblasts untreated or treated with ASO for 72 h (left panel); and % of nuclei per 50 cells without foci (light grey), with 1-4 foci (dark grey) or with more than 5 foci (black) when cells were treated with no ASO, a non-targeting control ASO (NTC), LNA-modified ASOs (ASOs 1-3) or 2'-O-MOE modified ASOs (ASOs 4-5) (right panel).

FIG. 4B depicts that both LNA and 2'-O-MOE ASOs significantly reduce the level of repeat containing transcripts at a dose of 100 nM two weeks after delivery without lipid assistance (gymnotic delivery) in primary cortical neurons derived from C9BAC mice, as measured by qRT-PCR.

FIG. 6A-FIG. 6B depicts the expression of V1-V3 repeat containing transcripts (FIG. 6A) and all transcripts (FIG. 6B) in cortex and spinal cord quantified by qRT-PCR in mice infused with PBS (dark grey), NTC ASO (light grey), ASO3 (green) or ASO5 (blue) at the indicated dose. For each dose level, n=5-7, except NTC group (n=3).

FIG. 8A depicts ASO5 and its derivatives (ASO5-1 and ASO5-2) and the chemical structure of them. Left panel: ASO5 and its derivatives (ASO5-1 and ASO5-2)—chemistry and maximum tolerated dose (MTD) in nmol evaluated in vivo in 5-6-month-old wild-type C57Bl/6 mice after ICV bolus injections. Right panel: green triangle, phosphorothioate linkage (PS);

FIG. 8B depicts the effect of 100 nM of a mixed PS/PO on ASO5 efficacy in patient-derived fibroblasts on V1-V3 (left) or all expression level (right panel).

FIG. 9A depicts the dose response to ASO5, ASO5-1 and ASO5-2 at 72 hours, as measured by luciferase assay.

FIG. 9B depicts the schematic of experimental design in heterozygous C9BAC mice the result. Left panel, vehicle control (PBS), ASO5, ASO5-1 or ASO5-2 were injected into the right lateral ventricle of 5-6-month-old C9BAC mice. Brain and spinal cord were harvested and dissected eight weeks after treatment for RNA and DPR analysis. Right panel, no significant change in body weight was observed eight weeks after treatment when mice were treated with ASO.

FIG. 10A depicts the expression of V1-V3 repeat containing transcripts in cortex and spinal cord quantified by qRT-PCR in mice treated with PBS (dark grey), ASO5 (light blue), ASO5-1 (medium blue) and ASO5-2 (dark blue) eight weeks after administration of 30 nmol of each ASO. For each ASO group, n=5-7.

FIG. 10B depicts the dose response of V1-V3 transcripts to ASO5 and ASO5-1 in brain and spinal cord, as measured by qRT-PCR.

FIG. 14A depicts the schematic of experimental design for a timecourse experiment in heterozygous C9BAC mice. Vehicle control (PBS) and a single injection of 1, 5, 15, 30, 60 or 80 nmol of ASO5-2 was administered in of 5-6-month-old heterozygous C9BAC mice. Brain and spinal cord were collected and analyzed 24 hours, 3, 8, 12 or 20 weeks after treatment.

FIG. 14B depicts the expression of V1-V3 repeats containing transcripts (left top) and all transcripts (left bottom) measured by qRT-PCR in mice 3 weeks after injection with PBS, 1, 5, 15, 30 or 60 nmol of ASO5-2 into the right lateral ventricle. Right panel: a dose response curve after using the Hill equations nonlinear regression model.

FIG. 15A depicts the expression of poly-GP (left) and poly-PR (right) measured by qRT-PCR in mice 3 weeks after injection with PBS, 1, 5, 15, 30 or 60 nmol of ASO5-2 into the right lateral ventricle. Right panel: a dose response curve after using the Hill equations nonlinear regression model.

FIG. 15B depicts a time course experiment performed in mice treated with ASO5-2. Tissues were collected and analyzed at 24 hours, 3 weeks, 8 weeks, 12 and 20 weeks after treatment. Expression of V1-V3 (repeat-containing) transcripts was analyzed in cortex 24 hours, 3, 8, 12 or 20 weeks after a single bolus injection of ASO5-2 (30 nmol dose, except where indicated otherwise).

FIG. 16A depicts the expression of V1-V3 (repeat-containing) transcripts and all transcripts in cortex. The analysis was performed 8 weeks after a single dose injection of 30 nmol of ASO5, ASO5-1 and ASO5-2. For each group, n=5-7.

FIG. 16B depicts a time course experiment performed in mice treated with 30 nmol of ASO5-2. Tissues were collected and analyzed at 24 hours, 3 weeks, 8 weeks, 12 and 20 weeks after treatment. Expression of poly-GP was analyzed in cortex 24 hours, 3, 8, 12 or 20 weeks after a single dose injection of ASO5-2.

FIG. 18A depicts that ASO treatment did not alter motor performance on a 5-minute accelerating rotarod task during the treatment course.

FIG. 18B depicts the % of nuclei per 100 fibroblasts without antisense foci (light grey), with 1-9 antisense foci (dark grey) or with more than 10 antisense foci (black) after a 72 h treatment with vehicle control or ASOs targeting the C9 antisense transcript. Red star indicates ASOs tested in vivo.

FIG. 19A-FIG. 19B depicts the effect of combined suppression of expression of sense and anti-sense transcripts of C9ORF72. Schematic of experimental design in hetereozygous C9 mice derived from the Baloh lab was shown (FIG. 19A left). Expression of V1-V3 (repeat-containing) transcripts (FIG. 19A, middle) and all transcripts (FIG. 19A, right) as assayed by qRT-PCR, sense repeat-containing transcripts (FIG. 19B, left) and antisense repeat-containing transcripts (FIG. 19B, right) as assayed by the QuantiGene branched DNA assay, was analyzed 3 weeks after injection of vehicle control (PBS), 60 nmol of non-targeting control (NTC), 30 nmol of ASO5-2 or AS ASO6 and a combination of 30 nmol ASO5-2 and 30 nmol of ASO6.

FIG. 20 depicts that combined treatment with ASOs targeting the sense and antisense repeat-containing transcripts can simultaneously reduce the expression of poly-GP (left) and poly-PR (right). Mice were analyzed 3 weeks after injection of vehicle control (PBS), 60 nmol of non-targeting control (NTC), 30 nmol of ASO5-2 or AS ASO6 and a combination of 30 nmol ASO5-2 and 30 nmol of ASO6.

DETAILED DESCRIPTION

Figure 1A:
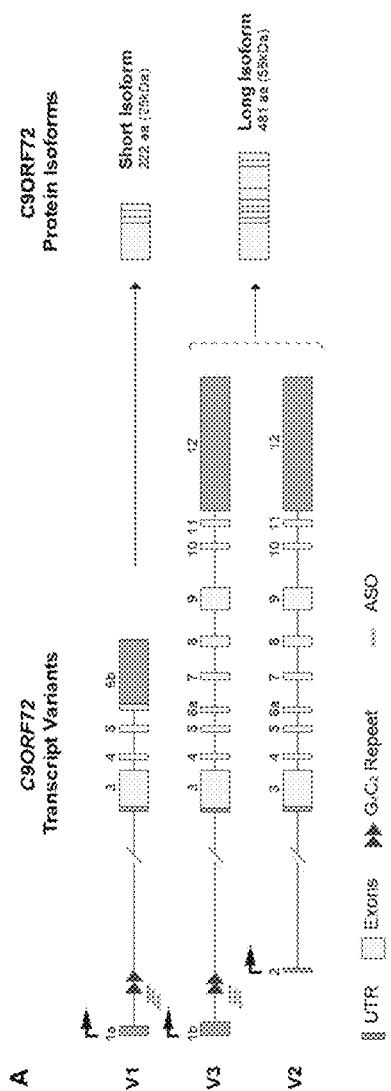
FIG. 1A depicts the schematic of C9ORF72 transcript variants and of the two protein isoforms as named in PubMed, along with a schematic of ASO binding sites. The repeat expansion (triangles) located in the first intron is expressed in variants 1 and 3 (V1-V3). Variant 2 (V2), the most abundant, starts from a different transcription start site (black arrow) and does not include the repeat expansion. V2 and V3 encode the main C9ORF72 protein isoform. Dark grey boxes represent untranslated regions (UTR); light grey boxes represent coding exons; black lines represent introns. ASOs used in this study (grey bars) target the intronic region flanking the repeat expansion.

The present disclosure provides antisense compounds, methods, and compositions for silencing C9ORF72 transcripts. The subject matter described herein is largely based on the finding that certain RNase H-dependent antisense compounds provide unexpected improvement in safety and in the silencing of C9ORF72 transcripts. The present disclosure provides antisense compounds, methods, and compositions for the treatment, prevention, or amelioration of diseases, disorders, and conditions associated with C9ORF72 in a subject in need thereof. Also contemplated are antisense compounds and methods for the preparation of a medicament for the treatment, prevention, or amelioration of a disease, disorder, or condition associated with C9ORF72. C9ORF72-related diseases, disorders, and conditions include, without limitation, neurological diseases and disorders, such as familial frontotemporal dementia (FTD) and amyotrophic lateral sclerosis (ALS).

It is to be understood that the methods described in this disclosure are not limited to particular methods and experimental conditions disclosed herein as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, $2^{nd}$ edition).

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). An RNA nucleotide refers to a single ribonucleotide. The term "DNA" or "DNA molecule" or "deoxyribonucleic acid molecule" refers to a polymer of deoxyribonucleotides. A DNA nucleotide refers to a single deoxyribonucleotide. As used herein, the term "DNA-like" refers to a conformation of, e.g. a modified nucleoside or nucleotide which is similar to the conformation of a corresponding unmodified DNA unit. For example, a DNA-like nucleotide may refer to a conformation of a modified deoxyribonucleotide similar to a corresponding unmodified deoxyribonucleotide. Examples of DNA-like nucleotides include, without limitation, e.g., 2'-deoxyribonucleotides, 2'-deoxy-2'-substituted arabinonucleotides (e.g., 2'-deoxy-2'-fluoroarabinonucleotides, also known in the art as 2'F-ANA or FANA), and corresponding phosphorothioate analogs. As used herein, the term "RNA-like" refers to a conformation of, e.g. a modified nucleoside or nucleotide which is similar to the conformation of a corresponding unmodified RNA unit. RNA-like conformations may adopt an A-form helix while DNA-like conformations adopt a B-form helix. Examples RNA-like nucleotides include, without limitation, e.g., 2'-substituted-RNA nucleotides (e.g., 2'-fluoro-RNA nucleotides also known in the art as 2'F-RNA), locked nucleic acid (LNA) nucleotides (also known in the art as bridged nucleic acids or bicyclic nucleotides), 2'-fluoro-4'-thioarabinonucleotide (also known in the art as 4'S-FANA nucleotides), 2'-O-alkyl-RNA, and corresponding phosphorothioate analogs.

DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary modified nucleotides are modified at any position so as to alter certain chemical properties of the nucleotide yet retain the ability of the modified nucleotide to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Modified nucleotides also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotides such as those described in Herdewijn, Antisense Nucleic Acid Drug Dev., 2000 Aug. 10(4):297-310.

Modified nucleotides may also comprise modifications to the sugar portion of the nucleotides. For example, the 2' OH-group may be replaced by a group selected from H, OR, R, F, Cl, Br, I, SH, SR, $NH_2$, NHR, $NR_2$, COOR, or OR, wherein R is substituted or unsubstituted C1-C6 alkyl, alkenyl, alkynyl, aryl, etc. For another example, the ribose sugar may be replaced with a bicyclic or tricylic moiety, such as in Locked Nucleic Acid, constrained ethyl, tricycloDNA, or other bridged or bicyclic modifications. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

As used herein, the terms "unmodified nucleotide" or "non-modified nucleotide" refers to a nucleotide composed of naturally occurring nucleobases, sugar moieties, and internucleotide linkages. In some embodiments, a non-modified nucleotide is an RNA nucleotide (i.e. β-D-ribonucleoside) or a DNA nucleotide (i.e. β-D-deoxyribonucleoside).

The term "oligonucleotide" refers to a short polymer of nucleotides and/or modified nucleotides. As discussed above, the oligonucleotides may be linked with linkages which result in a lower rate of hydrolysis as compared to an oligonucleotide linked with phosphodiester linkages. For example, the nucleotides of the oligonucleotide may comprise triazole, amide, carbamate, methylenediol, ethylene diol, oxymethylthio, oxyethylthio, oxycarbonyloxy, phosphorodiamidate, phosphoroamidate, phosphonate, and/or phosphorothioate linkages. Alterations or modifications of the oligonucleotide can further include addition of non-nucleotide material, such as to the end(s) of the oligonucleotide or internally (at one or more nucleotides of the oligonucleotide).

As used herein, the term "antisense compound" refers to a compound, which is capable of inhibiting or "silencing" the expression of a target gene. In certain embodiments, the antisense compound is capable of preventing complete processing (e.g., the full translation and/or expression) of a transcript molecule through a post-transcriptional silencing mechanism. Antisense compounds include, without any limitation, antisense oligonucleotides, gapmer molecules, and dual-function oligonucleotides as well as precursors thereof. In some embodiments, the antisense compound directs a target nucleic acid for cleavage by ribonuclease H (RNase H). For example, an antisense compound of the present disclosure can be an antisense oligonucleotide that directs cleavage of a C9ORF72 transcript by RNase H. RNase H is a family of non-sequence-specific endonuclease enzymes that catalyze the cleavage of RNA in an RNA/DNA substrate via a hydrolytic mechanism.

The term "gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments." "Chimeric antisense compound" means an antisense compound that has at least two chemically distinct regions.

As used herein, the term "target gene" is a gene whose expression is to be substantially inhibited or "silenced." This silencing can be achieved by RNA silencing, e.g., by cleaving a transcript corresponding to a target gene or translational repression of the target gene. The term "non-target gene" is a gene whose expression is not to be substantially silenced. For example, a target gene of the present invention is C9ORF72, and a non-target gene of the present invention is a gene that is not C9ORF72. In one embodiment, the polynucleotide sequences of the target and non-target gene (e.g., mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g., an orthologue or paralogue) of the target gene.

The term "antisense activity" means any detectable or measurable activity attributable to the hybridization of an antisense compound to its target nucleic acid. In some embodiments, antisense activity is a decrease in the amount or expression of a target nucleic acid or protein encoded by such target nucleic acid. "Antisense compound" means an oligomeric compound that is capable of undergoing hybridization to a target nucleic acid through hydrogen bonding. As used herein, "antisense oligonucleotide" means a single-stranded oligonucleotide having a nucleobase sequence that permits hybridization to a corresponding region or segment of a target nucleic acid.

The term "antisense inhibition" means reduction of target nucleic acid levels or target protein levels in the presence of an antisense oligonucleotide having a sequence that is sufficiently complementary to a target nucleic acid compared to target nucleic acid levels or target protein levels in the absence of the antisense compound. A target nucleic acid can be any nucleic acid. For example, a target nucleic acid of the present invention can be a C9ORF72 transcript.

The term "target-recognition sequence" refers to the portion of an antisense compound that recognizes a target nucleic acid. The target-recognition sequence has a nucleobase sequence that permits hybridization to a corresponding region or segment of a target nucleic acid.

The term "conserved region" refers to a portion, or portions, of a nucleic acid sequence that is conserved, i.e. a portion, or portions of the nucleic acid sequence having a similar or identical sequence across species. A conserved region may be computationally identified, e.g., using any sequence alignment software available in the art.

As used herein, the term "sufficiently complementary" means that the RNA silencing agent has a sequence (e.g., an antisense oligonucleotide having a target-recognition sequence), which is sufficient to bind the desired target transcript (e.g., a C9ORF72 transcript), and to trigger the RNA silencing of the target transcript (e.g., direct cleavage of the target mRNA by RNase H). For example, a target-recognition sequence with at least 90% complementarity to a target nucleic acid sequence (e.g., a portion of a C9ORF72 transcript) may be sufficiently complementary to trigger silencing of the C9ORF72 transcript. The term "perfectly complementary" refers to, e.g., a target-recognition sequence with 100% complementarity to a target nucleic acid sequence. Complementary nucleic acid molecules hybridize to each other. The term "hybridization" means the annealing of complementary nucleic acid molecules. In certain embodiments, complementary nucleic acid molecules include an antisense compound and a target nucleic acid.

The term "about" or "approximately" means within 20%, such as within 10%, within 5%, or within 1% or less of a given value or range.

As used herein, "administer" or "administration" refers to the act of injecting or otherwise physically delivering a substance as it exists outside the body (e.g., an antisense compound provided herein) into a patient. The antisense oligonucleotides described herein may be administered to the central nervous system of a patient. The central nervous system includes the brain and spinal cord. Administration methods to the central nervous system include, but not limited to, intrathecal, intraventricular or intrastriatal infusion or delivery and/or any other method of physical delivery described herein or known in the art. Intraventricular infusion may comprise administration using an Ommaya reservoir.

When a disease, or a symptom thereof, is being managed or treated, administration of the substance typically occurs after the onset of the disease or symptoms thereof. When a disease, or symptom thereof, is being prevented, administration of the substance typically occurs before the onset of the disease or symptoms thereof and may be continued chronically to defer or reduce the appearance or magnitude of disease-associated symptoms, e.g., damage to the involved tissues and airways.

As used herein, the term "composition" is intended to encompass a product containing the specified ingredients (e.g., an antisense compound provided herein) in, optionally, the specified amounts, as well as any product which results, directly or indirectly, from combination of the specified ingredients in, optionally, the specified amounts.

"Effective amount" means the amount of active pharmaceutical agent (e.g., an antisense compound of the present disclosure) sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

As used herein, the terms "subject" and "patient" are used interchangeably. As used herein, a subject is can be a mammal, such as a non-primate (e.g., cows, pigs, horses, cats, dogs, rats, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sports animals, and pets. In one embodiment, the subject is a mammal, such as a human, having a C9ORF72-related disorder (e.g., ALS). In another embodiment, the subject is a mammal, such as a human, that is at risk for developing a C9ORF72-related disorder.

As used herein, the term "therapy" refers to any protocol, method and/or agent that can be used in the prevention, management, treatment and/or amelioration of a disease or a symptom related thereto, such as a C9ORF72-related disorder (e.g., ALS). In some embodiments, the term "therapy" refers to any protocol, method and/or agent that can be used in the modulation of an immune response to an infection in a subject or a symptom related thereto. In some embodiments, the terms "therapies" and "therapy" refer to a biological therapy, supportive therapy, and/or other therapies useful in the prevention, management, treatment and/or amelioration of a disease or a symptom related thereto, such as a C9ORF72-related disorder known to one of skill in the art such as medical personnel. In other embodiments, the terms "therapies" and "therapy" refer to a biological therapy, supportive therapy, and/or other therapies useful in the modulation of an immune response to an infection in a subject or a symptom related thereto known to one of skill in the art such as medical personnel.

As used herein, the terms "treat," "treatment" and "treating" refer to the reduction or amelioration of the progression, severity, and/or duration of a disease or a symptom related thereto, such as a C9ORF72-related disorder, resulting from the administration of one or more therapies (including, but not limited to, the administration of one or more prophylactic or therapeutic agents, such as an antisense oligonucleotide provided herein). The term "treating," as used herein, can also refer to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis.

Antisense Compounds

The present disclosure provides an antisense compound that is capable of mediating cleavage of at least 50%, at least 55%, at least 60%, at least 65%, at least 70%, at least 75%, at least 80%, at least 85%, at least 90%, at least 95% or more of C9ORF72 transcripts. In one embodiment, the antisense compound is capable of mediating cleavage of at least 80% of C9ORF72 transcripts. In one embodiment, the antisense compound is capable of mediating cleavage of at least 90% of C9ORF72 transcripts.

In certain embodiments, antisense compounds that is capable of mediating cleavage of an C9ORF72 transcript or portion thereof, have chemically modified subunits arranged in patterns, or motifs, to confer to the antisense compounds properties, such as enhanced the inhibitory activity, increased binding affinity for a target nucleic acid, or resistance to degradation by in vivo nucleases.

In some embodiments, an antisense compound of the present disclosure is an antisense oligonucleotide. Chimeric antisense oligonucleotides typically contain at least one region modified so as to confer increased resistance to nuclease degradation, increased cellular uptake, increased binding affinity for the target nucleic acid, and/or increased inhibitory activity. A second region of a chimeric antisense compound may serve as a substrate for the cellular endonuclease RNase H, which cleaves the RNA strand of an RNA:DNA duplex. In some embodiments, an antisense compound of the present disclosure is a chimeric antisense oligonucleotide having a gapmer motif. In a gapmer, an internal region having a plurality of nucleotides that supports RNase H cleavage is positioned between external regions having a plurality of nucleotides that are chemically distinct from the nucleosides of the internal region.

In some embodiments, the present disclosure provides a synthetic antisense oligonucleotide having a target-recognition sequence that is sufficiently complementary to an C9ORF72 transcript or portion thereof, to direct cleavage of the C9ORF72 transcript by RNase H. The target-recognition sequence of the antisense oligonucleotide can be the full length of the antisense oligonucleotide, or a portion thereof. In some embodiments, the antisense oligonucleotide comprises a gapmer motif.

In the case of an antisense compound having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$ (i.e., OMe), among others), and bicyclic sugar modified nucleosides (such bicyclic sugar modified nucleosides may include those having a 4'-(CH$_2$)$_n$—O-2' bridge, where n=1 or n=2). In some embodiments, each distinct region comprises uniform sugar moieties.

The gapmer motif can be described using the formula "A-B-C", where "A" represents the length of the 5' wing region, "B" represents the length of the gap region, and "C" represents the length of the 3' wing region. As such, in some embodiments, an antisense oligonucleotide of the present disclosure has the formula:

A-B-C.

As used herein, a gapmer described as "A-B-C" has a configuration such that the gap segment is positioned immediately adjacent each of the 5' wing segment and the 3' wing segment. Thus, no intervening nucleotides exist between the 5' wing segment and gap segment, or the gap segment and the 3' wing segment.

In some embodiments, the 5' wing region represented by "A" comprises from about 0 to about 8 modified nucleotides, e.g., from about 1 to about 6 modified nucleotides. For example, the 5' wing region represented by "A" can be 0, 1, 2, 3, 4, 5, 6, 7, or 8 nucleotides in length. In some embodiments, the 3' wing region represented by "C" comprises about 0 to about 8 modified nucleotides, e.g., from about 1 to about 6 modified nucleotides. For example, the 3' wing region represented by "C" can be 0, 1, 2, 3, 4, 5, 6, 7, or 8 nucleotides in length. In some embodiments, "A" and "C" are the same, in some embodiments, "A" and "C" are different.

In some embodiments, the gap region represented by "B" comprises from about 4 to about 18 DNA nucleotides and/or DNA-like nucleotides, e.g., from about 4 to about 12 DNA nucleotides and/or DNA-like nucleotides. For example, the gap region represented by "B" can be 4, 5, 6, 7, 8, 9, 10, 11, 12, 13, 14, 15, 16, 17, or 18 DNA nucleotides and/or DNA-like nucleotides in length. Thus, an antisense oligonucleotide of the present disclosure having a target-recognition sequence with the formula "A-B-C" include, but are not limited to the following gapmer formats, for example 1-4-1 (i.e., one nucleotide-four nucleotides-one nucleotide), 1-5-1, 1-6-1, 1-7-1, 1-8-1, 1-9-1, 1-10-1, 1-11-1, 1-12-1, 2-4-2, 2-5-2, 2-6-2, 2-7-2, 2-8-2, 2-9-2, 2-10-2, 2-11-2, 2-12-2, 3-4-3, 3-5-3, 3-6-3, 3-7-3, 3-8-3, 3-9-3, 3-10-3, 3-11-3, 3-12-3, 4-4-4, 4-5-4, 4-6-4, 4-7-4, 4-8-4, 4-9-4, 4-10-4, 4-11-4, 4-12-4, 5-4-5, 5-5-5, 5-6-5, 5-7-5, 5-8-5, 5-9-5, 5-10-5, 5-11-5, 5-12-5, 6-4-6, 6-5-6, 6-6-6, 6-7-6, 6-8-6, 6-9-6, 6-10-6, 6-11-6, or 6-12-6. The wings may also be of different lengths, such as 1-10-6, 3-9-5, 7-9-2, 4-10-5, or other asymmetric combinations of wing lengths flanking a central DNA gap. A person of skill in the art will be able to identify additional asymmetric combinations of wing lengths.

In certain embodiments, antisense compounds targeted to a C9ORF72 nucleic acid possess a 5-8-5 or 5-10-5 gapmer format. In some embodiments, the antisense compound is an antisense oligonucleotide having a target-recognition sequence with the 5-8-5 or 5-10-5 format that is sufficiently complementary to a C9ORF72 transcript, or a portion thereof, to direct cleavage of the C9ORF72 transcript by RNase H. In some embodiments, the target-recognition sequence has the formula "A-B-C", wherein "A" comprises about 5 modified nucleotides, "B" comprises about 8-10 DNA nucleotides and/or DNA-like nucleotides, and "C" comprises about 5 modified nucleotides. In some embodiments, the target-recognition sequence has the formula "A-B-C", wherein "A" comprises 5 locked nucleotides, "B" comprises 8-10 DNA nucleotides and/or DNA-like nucleotides, and "C" comprises 5 locked nucleotides. In some embodiments, the target-recognition sequence has the formula "A-B-C", wherein "A" comprises 5 locked nucleotides, "B" comprises 8-10 DNA-like nucleotides, and "C" comprises 5 locked nucleotides.

In some embodiments, antisense compounds that target a C9ORF72 nucleic acid possess a "wingmer" motif. The wingmer motif can be described using the formula "X—Y" or "Y—X", where "X" represents the length of the wing region, and "Y" represents the length of the gap region. As such, in some embodiments, an antisense oligonucleotide of the present disclosure has the formula:

X—Y, or

Y—X.

As used herein, a wingmer described as "X—Y" or "Y—X" has a configuration such that the gap segment is positioned immediately adjacent to the wing segment. Thus, no intervening nucleotides exist between the wing segment and the gap segment. Non-limiting examples of wingmer configurations of an antisense compound of the present disclosure include, e.g., 1-15, 1-17, 1-19, 2-15, 2-17, 2-19, 2-22, 3-13, 3-17, 3-20, 3-21, 3-22, 4-12, 4-14, 4-16, 4-18, 4-19, 4-21, 5-11, 5-13, 5-14, 5-15, 5-16, 5-18, or 5-20.

In some embodiments, antisense compounds targeted to a C9ORF72 nucleic acid possess a gap-widened motif. As used herein, "gap-widened" refers to an antisense compound having a gap segment of 12 or more contiguous DNA nucleotides and/or DNA-like nucleotides adjacent to a wing region. In the case of a gap-widened gapmer, the gapmer comprises a gap region having 12 or more contiguous DNA nucleotides and/or DNA-like nucleotides positioned between and immediately adjacent to the 5' and 3' wing segments. In the case of a gap-widened wingmer, the wingmer comprises a gap region having 12 or more contiguous DNA nucleotides and/or DNA-like nucleotides positioned immediately adjacent to the wing segment.

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleotide linkages of the oligonucleotide.

Modifications to antisense compounds encompass substitutions or changes to internucleotide linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

The naturally occurring internucleotide linkage of RNA and DNA is a 3' to 5' phosphodiester linkage. Antisense compounds having one or more modified, i.e. non-naturally occurring, internucleotide linkages are often selected over antisense compounds having naturally occurring internucleotide linkages because of desirable properties such as, for example, enhanced cellular uptake, enhanced affinity for target nucleic acids, and increased stability in the presence of nucleases.

Oligonucleotides having modified internucleotide linkages include internucleotide linkages that retain a phosphorus atom, as well as internucleotide linkages that do not have a phosphorus atom. Representative phosphorus containing internucleotide linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleotide linkages. In certain embodiments, the modified internucleotide linkages are phosphorothioate linkages. In certain embodiments, each internucleotide linkage of an antisense compound is a phosphorothioate internucleotide linkage.

Antisense compounds of the invention can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substituent groups (including 5' and 2' substituent groups, bridging of ring atoms to form bicyclic nucleic acids (BNA), replacement of the ribosyl ring oxygen atom with S, N(R), or $C(R^1)(R^2)$ (R=H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of ribonucleosides having modified sugar moieties include without limitation nucleosides comprising 5'-vinyl, 5'-methyl (R or S), 4'-S, 2'H, 2'-F (i.e., 2'-fluoro), 2'-$OCH_3$ (i.e., 2'-O-methyl) and 2'-$O(CH_2)_2OCH_3$ (i.e., 2'-O-methoxyethyl) substituent groups. The substituent at the 2' position can also be selected from allyl, amino, azido, thio, O-allyl, O—C1-C10 alkyl, $OCF_3$, $O(CH_2)_2SCH_3$, $O(CH_2)_2$—O—$N(R_m)(R_n)$, and O—$CH_2$—C(=O)—$N(R_m)$ $(R_n)$, where each $R_m$ and $R_n$ is, independently, H or substituted or unsubstituted C1-C10 alkyl. 2'-modified nucleotides are useful in the present invention, for example, 2'-O-methyl RNA, 2'-O-methoxyethyl RNA, 2'-fluoro RNA, and others envisioned by one of ordinary skill in the art.

Examples of bicyclic nucleic acids (BNAs) include without limitation nucleosides comprising a bridge between the 4' and the 2' ribosyl ring atoms. A BNA comprising a bridge between the 4' and 2' ribosyl ring atoms can be referred to as a locked nucleic acid (LNA), and is often referred to as inaccessible RNA. As used herein, the term "locked nucleotide" or "locked nucleic acid (LNA)" comprises nucleotides in which the 2' deoxy ribose sugar moiety is modified by introduction of a structure containing a heteroatom bridging from the 2' to the 4' carbon atoms. The term "non-locked nucleotide" comprises nucleotides that do not contain a bridging structure in the ribose sugar moiety. Thus, the term comprises DNA and RNA nucleotide monomers (phosphorylated adenosine, guanosine, uridine, cytidine, deoxyadenosine, deoxyguanosine, deoxythymidine, deoxycytidine) and derivatives thereof as well as other nucleotides having a 2'-deoxy-erythro-pentofuranosyl sugar moiety or a ribopentofuranosyl moiety. In certain embodiments, antisense compounds provided herein include one or more BNA nucleosides wherein the bridge comprises one of the formulas: 4'-($CH_2$)—O-2' (LNA); 4'-($CH_2$)—S-2'; 4'-($CH_2$)—O-2' (LNA); 4'-($CH_2$)2-O-2' (ENA); 4'-C($CH_3$)2-O-2' (see PCT/US2008/068922); 4'-CH($CH_3$)—O-2' and 4'-CH ($CH_2OCH_3$)—O-2' (see U.S. Pat. No. 7,399,845, issued on Jul. 15, 2008); 4'-$CH_2$—N($OCH_3$)-2' (see PCT/US2008/064591); 4'-$CH_2$—O—N($CH_3$)-2' (see published U.S. Patent Application US2004-0171570, published Sep. 2, 2004); 4'-$CH_2$—N(R)—O-2' (see U.S. Pat. No. 7,427,672, issued on Sep. 23, 2008); 4'-$CH_2$—C($CH_3$)-2' and 4'-$CH_2$—C(=$CH_2$)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/DK98/00393, published on Mar. 25, 1999 as WO 99/14226).

In some embodiments, antisense compounds provided herein include one or more 2', 4'-constrained nucleotides. For example, antisense compounds provided by the present disclosure include those having one or more constrained ethyl (cEt) or constrained methoxyethyl (cMOE) nucleotides. In some embodiments, antisense compounds provided herein are antisense oligonucleotides comprising one or more constrained ethyl (cEt) nucleotides. The terms "constrained ethyl" and "ethyl-constrained" are used interchangeably.

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

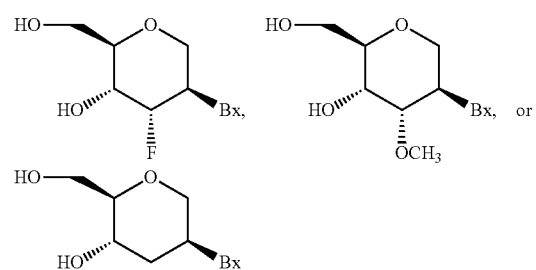

Many other bicyclo and tricyclo sugar surrogate ring systems are also known in the art that can be used to modify nucleosides for incorporation into antisense compounds (see for example review article: Leumann, J. C, *Bioorganic & Medicinal Chemistry*, 2002, 10, 841-854; Ito, K. R.; Obika, S., Recent Advances in Medicinal Chemistry of Antisense Oligonucleotides. In *Comprehensive Medicinal Chemistry*, 3rd edition, Elsevier: 2017). Such ring systems can undergo various additional substitutions to enhance activity.

Methods for the preparations of modified sugars are well known to those skilled in the art. In nucleotides having modified sugar moieties, the nucleobase moieties (natural, modified or a combination thereof) are maintained for hybridization with an appropriate nucleic acid target.

In certain embodiments, antisense compounds targeted to a C9ORF72 nucleic acid comprise one or more kinds of modified nucleotides. In one embodiment, antisense compounds targeted to a C9ORF72 nucleic acid comprise 2'-modified nucleotides. In one embodiment, antisense compounds targeted to a C9ORF72 nucleic acid comprise a 2'-O-methyl RNA, a 2'-O-methoxyethyl RNA, or a 2'-fluoro RNA. In one embodiment, antisense compounds targeted to a C9ORF72 nucleic acid comprise tricyclo-DNA. Tricyclo-DNA belongs to a class of constrained DNA analogs that display improved hybridizing capacities to complementary RNA, see, e.g., Ittig et al., *Nucleic Acids Res.* 32:346-353 (2004); Ittig et al., Prague, Academy of Sciences of the Czech Republic. 7:21-26 (Coll. Symp. Series, Hocec, M., 2005); Ivanova et al., *Oligonucleotides* 17:54-65 (2007); Renneberg et al., *Nucleic Acids Res.* 30:2751-2757 (2002); Renneberg et al., *Chembiochem.* 5:1114-1118 (2004); and Renneberg et al., *JACS.* 124:5993-6002 (2002). In one embodiment, antisense compounds targeted to a C9ORF72 nucleic acid comprise a locked nucleotide, an ethyl-constrained nucleotide, or an alpha-L-locked nucleic acid. Various alpha-L-locked nucleic acids are known by those of ordinary skill in the art, and are described in, e.g., Sorensen et al., *J. Am. Chem. Soc.* (2002) 124(10):2164-2176.

In certain embodiments, antisense compounds targeted to a C9ORF72 nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format wherein 9 non-locked nucleotides are flanked by 3 locked nucleotides on each side.

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo, such as 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to a C9ORF72 nucleic acid comprise one or more modified nucleotides having modified sugar moieties. In some embodiments, the modified nucleotide is a locked nucleotide. In certain embodiments, the locked nucleotides are arranged in a gapmer motif, e.g. a 3-9-3 gapmer format wherein 9 non-locked nucleotides are flanked by 3 locked nucleotides on each side. In certain embodiments, antisense compounds targeted to a C9ORF72 nucleic acid comprise one or more modified nucleotides. In some embodiments, the modified nucleotide is 5-methylcytosine. In certain embodiments, each cytosine is a 5-methylcytosine.

In some embodiments, an antisense compound of the present disclosure directs cleavage of a C9ORF72 transcript by RNase H. In such embodiments, the antisense compound may be referred to as an RNase H-dependent antisense compound. In some embodiments the antisense compound is an RNase H-dependent antisense oligonucleotide. In some embodiments, an antisense oligonucleotide of the present disclosure is an RNase H-dependent antisense oligonucleotide, and may be a single-stranded, chemically modified oligonucleotide that binds to a complementary sequence in the target transcript (e.g., a C9ORF72 transcript). An RNase H-dependent antisense oligonucleotide of the present disclosure reduces expression of a target gene by RNase H-mediated cleavage of the target transcript, and by inhibition of translation by steric blockade of ribosomes. In some embodiments, an antisense compound of the present disclosure is capable of mediating cleavage of at least 50%, at least 55%, at least 60%, at least 65%, at least 70%, at least 75%, at least 80%, at least 85%, at least 90%, at least 95% or more of C9ORF72 transcripts by RNase-H. In one embodiment, the antisense compound is capable of mediating cleavage of at least 80% of C9ORF72 transcripts by RNase-H. In one embodiment, the antisense compound is capable of mediating cleavage of at least 90% of C9ORF72 transcripts by RNase-H.

In certain embodiments, an antisense compound that targets a C9ORF72 transcript is from about 6 to about 24 subunits in length. In other embodiments, the antisense compound that targets a C9ORF72 transcript is from about 8 to about 80 subunits in length. For example, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments, the antisense compounds are less than 40 linked subunits in length. In some embodiments, the antisense compounds are from about 12 to about 25 linked subunits in length. In some embodiments, the antisense compounds are from about 15 to about 20 linked subunits in length. In some embodiments, the antisense compound is an antisense oligonucleotide that targets a C9ORF72 transcript, and the linked subunits are linked nucleotides.

In certain embodiments antisense compounds targeted to a C9ORF72 transcript may be shortened or truncated. For example, a single subunit may be deleted from the 5' end (5' truncation), or alternatively from the 3' end (3' truncation). A shortened or truncated antisense compound targeted to a C9ORF72 transcript may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Branched Antisense Compounds

The present disclosure also provides branched antisense compounds comprising two or more target-recognition sequences that targets a portion of a C9ORF72 nucleic acid. A branched antisense compound of the present disclosure may be, e.g., a branched antisense oligonucleotide compound.

As used herein, the term "branched antisense compound" or "branched antisense oligonucleotide" refers to two or more antisense compounds or antisense oligonucleotides that are connected together.

In one embodiment, a branched oligonucleotide compound comprises two or more target-recognition sequences, wherein the target-recognition sequences are connected to one another by one or more moieties selected from a linker, a spacer, and a branching point. Target-recognition sequences are described herein. In some embodiments, the branched oligonucleotide compound comprises 2, 3, 4, 5, 6, 7, 8, or more target-recognition sequences, wherein each target-recognition sequence comprises a 5' end and a 3' end, and each target-recognition sequence is independently connected to a linker, a spacer, or a branching point at the 5' end or the 3' end. In some embodiments, each target-recognition sequence is connected to a linker, a spacer, or a branching point at the 5' end. In some embodiments, each target-recognition sequence is connected to a linker, a spacer, or a branching point at the 3' end. In another embodiment, each target-recognition sequence is connected to a linker, a spacer, or a branching point. In some embodiments, each of the target-recognition sequences are antisense compounds and/or oligonucleotides that target a portion of a C9ORF72 nucleic acid.

In some embodiments, a branched oligonucleotide compound of the present disclosure has the formula $$L\text{-}(N)_n$$

wherein N represents a target-recognition sequence of the present disclosure; n represents an integer, e.g., 2, 3, 4, 5, 6, 7, or 8; and L represents a linker selected from an ethylene glycol chain, an alkyl chain, a peptide, RNA, DNA, a phosphate, a phosphonate, a phosphoramidate, an ester, an amide, a triazole, and any combination thereof.

In some embodiments, a branched oligonucleotide compound of the present disclosure has the formula $$L\text{-}(N)_n$$

wherein the compound optionally further comprises one or more branching points B, and wherein the compound optionally further comprises one or more spacers S. In such embodiments, each of the one or more branching points B independently represents a polyvalent organic species or derivative thereof, and each of the one or more spacers S is independently selected from an ethylene glycol chain, an alkyl chain, a peptide, RNA, DNA, a phosphate, a phosphonate, a phosphoramidate, an ester, an amide, a triazole, and any combination thereof. For example, a branched oligonucleotide compound of the present disclosure having the formula L-(N)n has a structure, not to be limited in any fashion, e.g.,

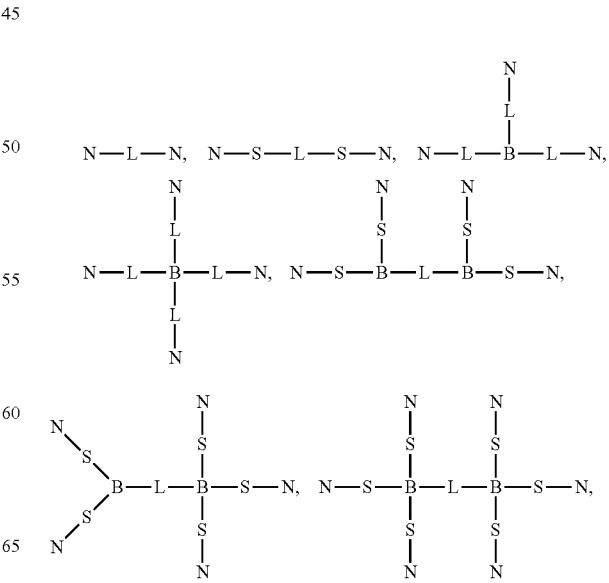

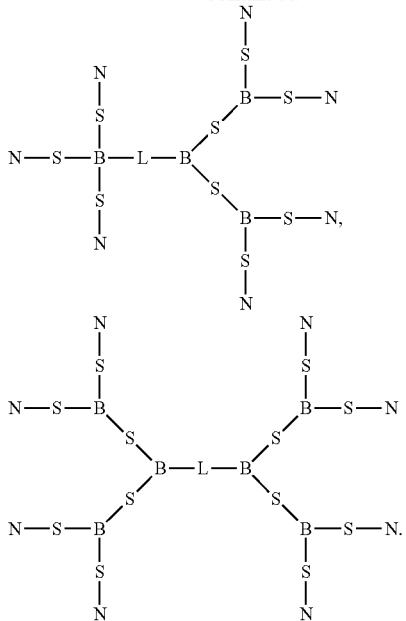

Target-Recognition Sequences

The present disclosure provides an antisense oligonucleotide comprising a target-recognition sequence that targets a portion of a chromosome 9 open reading frame 72 (C9ORF72) nucleic acid (e.g., a C9ORF72 transcript). In certain embodiments, an antisense oligonucleotide has a nucleobase sequence that, when written in the 5' to 3' direction, comprises the reverse complement of a portion of a C9ORF72 nucleic acid. In some embodiments, an antisense oligonucleotide is an antisense oligonucleotide. In certain such embodiments, an antisense oligonucleotide has a nucleobase sequence that, when written in the 5' to 3' direction, comprises the reverse complement of a portion of a C9ORF72 nucleic acid.

In certain embodiments, a target region is a structurally defined region of a C9ORF72 nucleic acid. For example, a target region may encompass a 3' untranslated region (UTR), a 5' untranslated region (UTR), an exon, an intron, an exon/intron junction, a coding region, a translation initiation region, translation termination region, or other defined nucleic acid region, for example, an open reading frame, or the junction between an open reading frame and an untranslated region and any combinations thereof. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense oligonucleotide hybridizes, such that a desired effect occurs. In certain embodiments, the desired effect is a reduction in transcript target nucleic acid levels, i.e., a reduction in C9ORF72 transcript levels. In certain embodiments, the desired effect is reduction of levels of protein encoded by the target nucleic acid or a phenotypic change associated with the target nucleic acid, e.g., a reduction in the level of C9ORF72 protein or dipeptide repeat proteins.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous.

Suitable target segments may be found within a 5' UTR, a coding region, a 3' UTR, an intron, an exon, and/or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid (e.g., C9ORF72) to other sequences throughout the genome. For example, the BLAST algorithm may be used to identify regions of similarity amongst different nucleic acids. This comparison can prevent the selection of antisense oligonucleotide sequences that may hybridize in a non-specific manner to sequences other than a selected target nucleic acid (i.e., non-target or off-target sequences). The determination of suitable target segments may include comparison of the sequences of a target nucleic acid (e.g., a C9ORF72 transcript) across several species. For example, various sequence alignment software are known in the art and can be used to identify regions of similar or identical sequence across species.

There may be variation in activity (e.g., as defined by percent reduction of target nucleic acid levels) of the antisense oligonucleotides within an active target region. In certain embodiments, reduction in C9ORF72 transcript levels is indicative of inhibition of C9ORF72 expression. Reductions in levels of a C9ORF72 protein are also indicative of inhibition of target transcript expression. Reductions in levels of a C9ORF72-associate dipeptide repeat protein are also indicative of inhibition of target transcript expression. Further, phenotypic changes are indicative of inhibition of C9ORF72 expression. In some embodiments, reduction in the transcript levels of a gene that operates within a C9ORF72 genetic pathway can indicate inhibition of C9ORF72 expression. For example, reduction in the transcript levels of a downstream component of a C9ORF72 genetic pathway is indicative of inhibition of C9ORF72.

An antisense oligonucleotide and a target nucleic acid (e.g., a C9ORF72 transcript or portion thereof) are complementary to each other when a sufficient number of nucleobases of the antisense oligonucleotide can hydrogen bond with the corresponding nucleobases of the target nucleic acid, such that a desired effect will occur (e.g., antisense inhibition of a target nucleic acid, such as a C9ORF72 transcript or portion thereof).

Non-complementary nucleobases between an antisense oligonucleotide and a C9ORF72 nucleic acid may be tolerated provided that the antisense oligonucleotide remains able to specifically hybridize to a target nucleic acid. Moreover, an antisense oligonucleotide may hybridize over one or more segments of a C9ORF72 nucleic acid such that intervening or adjacent segments are not involved in the hybridization event (e.g., a loop structure, mismatch or hairpin structure).

In certain embodiments, the antisense oligonucleotides provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense oligonucleotide with a target nucleic acid can be determined using routine methods.

For example, an antisense oligonucleotide in which 18 of 20 nucleobases of the antisense oligonucleotide are complementary to a target region (e.g., an equal length portion of a C9ORF72 transcript), and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligonucleotide which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense oligonucleotide with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense oligonucleotides provided herein, or specified portions thereof, are fully complementary (i.e. 100% complementary) to a target nucleic acid, or specified portion thereof. For example, antisense oligonucleotide may be fully complementary to a C9ORF72 nucleic acid, or a target region, or a target segment or target sequence thereof. As used herein, "fully complementary" or "perfectly complementary" means each nucleobase of an antisense oligonucleotide is capable of precise base pairing with the corresponding nucleobases of a target nucleic acid. For example, a 20 nucleobase antisense oligonucleotide is perfectly complementary to a target sequence that is 400 nucleobases long, so long as there is a corresponding 20 nucleobase portion of the target nucleic acid that is fully complementary to the antisense oligonucleotide. Perfectly complementary can also be used in reference to a specified portion of the first and/or the second nucleic acid. For example, a 20 nucleobase portion of a 30 nucleobase antisense oligonucleotide can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense oligonucleotide. At the same time, the entire 30 nucleobase antisense oligonucleotide may or may not be fully complementary to the target sequence, depending on whether the remaining 10 nucleobases of the antisense oligonucleotide are also complementary to the target sequence.

In some embodiments, the present disclosure provides an antisense oligonucleotide having a region of complementarity to a C9ORF72 antisense transcript sequence of 5' GAA-AGUAAAAAUGCGUCGAG 3' (SEQ ID NO:1). In some embodiments, the antisense oligonucleotide comprises a region of complementarity to a C9ORF72 antisense transcript sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to a C9ORF72 antisense transcript. In some embodiments, the antisense oligonucleotide comprises a region of complementarity to a C9ORF72 antisense transcript sequence that is perfectly complementary to a C9ORF72 antisense transcript.

In some embodiments, the present disclosure provides an antisense oligonucleotide having a region of complementarity to a C9ORF72 antisense transcript sequence of 5' CUC-CUUGUUUUCUUCUGGUU 3' (SEQ ID NO: 2). In some embodiments, the antisense oligonucleotide comprises a region of complementarity to a C9ORF72 antisense transcript sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to a C9ORF72 antisense transcript. In some embodiments, the antisense oligonucleotide comprises a region of complementarity to a C9ORF72 antisense transcript sequence that is perfectly complementary to a C9ORF72 antisense transcript.

In some embodiments, the present disclosure provides an antisense oligonucleotide having a region of complementarity to a C9ORF72 antisense transcript sequence of 5' CAG-GUCUUUUCUUGUUCACC 3' (SEQ ID NO: 3). In some embodiments, the antisense oligonucleotide comprises a region of complementarity to a C9ORF72 antisense transcript sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to a C9ORF72 antisense transcript. In some embodiments, the antisense oligonucleotide comprises a region of complementarity to a C9ORF72 antisense transcript sequence that is perfectly complementary to a C9ORF72 antisense transcript.

In some embodiments, the present disclosure provides an antisense oligonucleotide having a region of complementarity to a C9ORF72 antisense transcript sequence of 5' CCUC-CUUGUUUUCUUCUGGU 3' (SEQ ID NO: 4). In some embodiments, the antisense oligonucleotide comprises a region of complementarity to a C9ORF72 antisense transcript sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to a C9ORF72 antisense transcript. In some embodiments, the antisense oligonucleotide comprises a region of complementarity to a C9ORF72 antisense transcript sequence that is perfectly complementary to a C9ORF72 antisense transcript.

In some embodiments, the present disclosure provides an antisense oligonucleotide having a region of complementarity to a C9ORF72 sense transcript sequence of 5' GAGU-CGCGCGCUAGGGGC 3' (SEQ ID NO: 9). In some embodiments, the antisense oligonucleotide comprises a region of complementarity to a C9ORF72 sense transcript sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to a C9ORF72 sense transcript. In some embodiments, the antisense oligonucleotide comprises a region of complementarity to a C9ORF72 sense transcript sequence that is perfectly complementary to a C9ORF72 sense transcript.

In some embodiments, the present disclosure provides an antisense oligonucleotide having a region of complementarity to a C9ORF72 sense transcript sequence of 5' GAGUCGCGCGCUAGGGGC 3' (SEQ ID NO: 9), wherein the antisense oligonucleotide comprises internucleotide linkages from 5' to 3' of sooossssssssoos, wherein each s is a phosphorothioate linkage and each o is a phosphodiester linkage. In some embodiments, the antisense oligonucleotide comprises a region of complementarity to a C9ORF72 sense transcript sequence that is at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% complementary to a C9ORF72 sense transcript. In some embodiments, the antisense oligonucleotide comprises a region of complementarity to a C9ORF72 sense transcript sequence that is perfectly complementary to a C9ORF72 sense transcript.

In certain embodiments, the present disclosure provides an antisense oligonucleotide targeting a C9ORF72 antisense transcript, having a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence of any of the following:

```
                              (SEQ ID NO: 5)
5' CTCGACGCATTTTTACTTTC 3', (SEQ ID NO: 6)
5' AACCAGAAGAAAACAAGGAG 3', (SEQ ID NO: 7)
5' GGTGAACAAGAAAAGACCTG 3', (SEQ ID NO: 8)
5' ACCAGAAGAAAACAAGGAGG 3'.
```

In certain embodiments, the present disclosure provides an antisense oligonucleotide targeting a C9ORF72 sense transcript, having a nucleic acid sequence with at least 70%, at least 75%, at least 80%, at least 85%, at least 86%, at least 87% at least 88%, at least 89%, at least 90%, at least 91%, at least 92%, at least 93%, at least 94%, at least 95%, at least 96%, at least 97%, at least 98%, or at least 99% sequence identity to the nucleic acid sequence of 5' GCCCCTAGCGCGCGACTC 3' (SEQ ID NO: 10).

In some embodiments, the present disclosure provides an antisense oligonucleotide having a region of complementarity to a C9ORF72 antisense transcript sequence with a sequence modification pattern of $X_sX_oX_oX_oX_sX_sX_sX_sX_sX_sX_sX_sX_sX_sX_sX_oX_oX_oX_sX$, wherein s represents a phosphorothioate internucleotide linkage; o represents a phosphodiester internucleotide linkage; and X is an adenosine, a guanosine, a cytidine, or a thymine comprising a 2'-O-(2-methoxyethyl) modification.

In some embodiments, the present disclosure provides an antisense oligonucleotide having a region of complementarity to a C9ORF72 sense transcript sequence with a sequence modification pattern of $X_sX_oX_oX_oX_sX_sX_sX_sX_sX_sX_sX_sX_sX_sX_sX_oX_oX_oX_sX$, wherein s represents a phosphorothioate internucleotide linkage; o represents a phosphodiester internucleotide linkage; and $\underline{X}$ is an adenosine, a guanosine, a cytidine, or a thymine comprising a 2'-O-(2-methoxyethyl) modification.

In certain embodiments, the present disclosure provides an antisense oligonucleotide targeting a C9ORF72 antisense transcript, comprising the sequence $\underline{C}_s\underline{T}_s\underline{C}_o\underline{G}_o\underline{A}_s\underline{C}_s\underline{G}_s\underline{C}_s\underline{A}_s\underline{T}_s\underline{T}_s\underline{T}_s\underline{T}_s\underline{T}_s\underline{A}_s\underline{C}_o\underline{T}_o\underline{T}_o\underline{T}_s\underline{C}$ (SEQ ID NO: 12), wherein s represents a phosphorothioate internucleotide linkage; o represents a phosphodiester internucleotide linkage; $\underline{A}$ is an adenosine comprising a 2'-O-(2-methoxyethyl) modification; $\underline{G}$ is a guanosine comprising a 2'-O-(2-methoxyethyl) modification; $\underline{C}$ is a cytidine comprising a 2'-O-(2-methoxyethyl) modification; $\underline{T}$ is a thymine comprising a 2'-O-(2-methoxyethyl) modification; and each cytosine is a 5-methylcytosine.

In certain embodiments, the present disclosure provides an antisense oligonucleotide targeting a C9ORF72 antisense transcript, comprising the sequence $\underline{A}_s\underline{A}_s\underline{C}_o\underline{C}_o\underline{A}_s\underline{G}_s\underline{A}_s\underline{A}_s\underline{G}_s\underline{A}_s\underline{A}_s\underline{A}_s\underline{A}_s\underline{C}_s\underline{A}_s\underline{A}_o\underline{G}_o\underline{G}_o\underline{A}_s\underline{G}$ (SEQ ID NO: 13), wherein s represents a phosphorothioate internucleotide linkage; o represents a phosphodiester internucleotide linkage; $\underline{A}$ is an adenosine comprising a 2'-O-(2-methoxyethyl) modification; $\underline{G}$ is a guanosine comprising a 2'-O-(2-methoxyethyl) modification; $\underline{C}$ is a cytidine comprising a 2'-O-(2-methoxyethyl) modification; $\underline{T}$ is a thymine comprising a 2'-O-(2-methoxyethyl) modification; and each cytosine is a 5-methylcytosine.

In certain embodiments, the present disclosure provides an antisense oligonucleotide targeting a C9ORF72 antisense transcript, comprising the sequence $\underline{G}_s\underline{G}_o\underline{T}_o\underline{G}_o\underline{A}_s\underline{A}_s\underline{C}_s\underline{A}_s\underline{A}_s\underline{G}_s\underline{A}_s\underline{A}_s\underline{A}_s\underline{A}_s\underline{G}_s\underline{A}_o\underline{C}_o\underline{C}_o\underline{T}_s\underline{G}$ (SEQ ID NO: 14), wherein s represents a phosphorothioate internucleotide linkage; o represents a phosphodiester internucleotide linkage; $\underline{A}$ is an adenosine comprising a 2'-O-(2-methoxyethyl) modification; $\underline{G}$ is a guanosine comprising a 2'-O-(2-methoxyethyl) modification; $\underline{C}$ is a cytidine comprising a 2'-O-(2-methoxyethyl) modification; $\underline{T}$ is a thymine comprising a 2'-O-(2-methoxyethyl) modification; and each cytosine is a 5-methylcytosine.

In certain embodiments, the present disclosure provides an antisense oligonucleotide targeting a C9ORF72 antisense transcript, comprising the sequence $\underline{A}_s\underline{C}_s\underline{C}_o\underline{A}_o\underline{G}_s\underline{A}_s\underline{A}_s\underline{G}_s\underline{A}_s\underline{A}_s\underline{A}_s\underline{A}_s\underline{C}_s\underline{A}_s\underline{A}_s\underline{G}_o\underline{G}_o\underline{A}_o\underline{G}_s\underline{G}$ (SEQ ID NO: 15), wherein s represents a phosphorothioate internucleotide linkage; o represents a phosphodiester internucleotide linkage; $\underline{A}$ is an adenosine comprising a 2'-O-(2-methoxyethyl) modification; $\underline{G}$ is a guanosine comprising a 2'-O-(2-methoxyethyl) modification; $\underline{C}$ is a cytidine comprising a 2'-O-(2-methoxyethyl) modification; $\underline{T}$ is a thymine comprising a 2'-O-(2-methoxyethyl) modification; and each cytosine is a 5-methylcytosine.

In certain embodiments, the present disclosure provides an antisense oligonucleotide targeting a C9ORF72 sense transcript, comprising the sequence $\underline{G}_s\underline{C}_o\underline{C}_o\underline{C}_o\underline{C}_s\underline{T}_s\underline{A}_s\underline{G}_s\underline{C}_s\underline{G}_s\underline{C}_s\underline{G}_s\underline{C}_s\underline{G}_o\underline{A}_o\underline{C}_o\underline{T}_s\underline{C}$ (SEQ ID NO: 16), wherein s represents a phosphorothioate internucleotide linkage; o represents a phosphodiester internucleotide linkage; $\underline{A}$ is an adenosine comprising a 2'-O-(2-methoxyethyl) modification; $\underline{G}$ is a guanosine comprising a 2'-O-(2-methoxyethyl) modification; $\underline{C}$ is a cytidine comprising a 2'-O-(2-methoxyethyl) modification; $\underline{T}$ is a thymine comprising a 2'-O-(2-methoxyethyl) modification; and each cytosine is a 5-methylcytosine.

Dipeptide Repeat Region (DPR) Proteins

As used herein, a "dipeptide repeat region protein" or "dipeptide repeat protein" or "DPR protein" or "expanded repeat protein" or "polydipeptide" or "Repeated-Associated Non-ATG (RAN) dipeptide" refers to proteins that are expressed from the nucleotide repeat regions of transcripts associated with repeat expansion diseases or disorders. Exemplary DPR proteins include, but are not limited to, the DPR proteins expressed from the hexanucleotide $G_4C_2$ repeat located in intron 1 of C9ORF72. These DPR proteins are translated from all six open reading frames in either the sense or antisense direction of the $G_4C_2$ nucleotide repeat. The DPR proteins include poly glycine-alanine or poly(GA), poly glycine-arginine or poly(GR), poly proline-alanine or poly(PA), poly proline-arginine or poly(PR), and poly glycine-proline or poly(GP). Poly(GP) is generated from both the C9ORF72 sense transcript and C9ORF72 antisense transcript. Poly(GR) and poly(GA) are generated from the C9ORF72 sense transcript. Poly(PA) and poly(PR) are generated from the C9ORF72 antisense transcript. The C9ORF72 DPR proteins are further described in Freibaum et al. 2017. Front. Mol. Neurosci. 10: 35.

Conjugated Antisense Oligonucleotides

Antisense oligonucleotides may be covalently linked to one or more moieties, ligands, or conjugates, which enhance the activity, cellular distribution or cellular uptake of the resulting antisense oligonucleotides. Antisense oligonucleotides may be covalently linked to one or more moieties, ligands, or conjugates which enhance and/or optimize pharmacokinetic parameters. Various pharmacokinetic parameters are known to a person of ordinary skill in the art, for example, absorbance, concentration of a compound in the body, the degree to which a compound permeates the body, the rate of elimination/clearance of a compound, the volume of plasma cleared of a compound per unit time, and others.

Typical conjugate groups include hydrophobic moieties such as cholesterol and lipid moieties. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N.Y. Acad. Sci., 1992,660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), an unsaturated fatty acid such as docosahexaenoic acid (Nikan et al, Mol Ther Nucleic Acids. 2016, 5, e344), or an octadecylamine or hexylamino-carbonyl-t oxycholesterol moiety (Crooke et al., J. Pharmacol. Exp. Ther., 1996, 277, 923-937). Diverse lipid conjugates can preferentially drive oligonucleotide uptake into different tissues (Biscans et al, Nucleic Acids Res. 2019, 47, 1082-1096). For example, a lipid moiety based on 1-O-hexa-decyloxy-1,3-propanediol can be conjugated to an antisense oligonucleotide of the present disclosure. Such a lipid moiety has previously been shown to increase small molecule uptake and improve the oral bioavailability of nucleoside drugs (see, e.g., Aldern et al., Mol. Pharmacol. 2003, 63:678-681; and Hostetler, Antiviral Res. 2009, 82:A84-A98). Additional conjugate groups include carbohydrates, phospholipids, biotin, phenazine, folate, phenanthridine, anthraquinone, acridine, fluoresceins, rhodamines, coumarins, and dyes. In some embodiments, conjugation of a ligand to an antisense oligonucleotide allows recognition by cell-surface receptors (see, e.g., Wolfrum et al., Nat. Biotechnol. 2007, 25:1149-1157; Hostetler et al., Antiviral Chem. Chemother. 2001, 12:61-70; and Prakash et al., Nucleic Acids Res. 2014, 42:8796-807). Methods of attaching one or more moieties or conjugates are well known in the art.

Antisense oligonucleotides can also be modified to have one or more stabilizing groups that are generally attached to one or both termini of antisense oligonucleotides to enhance properties such as, for example, nuclease stability. Included in stabilizing groups are cap structures. These terminal modifications protect the antisense oligonucleotide having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense oligonucleotide to impart nuclease stability include those disclosed in WO 03/004602 published on Jan. 16, 2003.

In some embodiments, an antisense oligonucleotide of the present disclosure comprises a conjugate. In one embodiment, an antisense oligonucleotide of the present disclosure comprises an antisense oligonucleotide sequence and a conjugate, wherein the conjugate is linked to the antisense oligonucleotide sequence. In some embodiments, the conjugate is selected from any of the conjugates described herein, for example, a hydrophobic conjugate, a tissue-targeting conjugate, or a conjugate designed to optimize pharmacokinetic parameters. A hydrophobic conjugate useful for conjugating to antisense oligonucleotides of the present disclosure, includes a hexadecyloxypropyl conjugate, a cholesterol conjugate, a polyunsaturated fatty acid conjugate, and others known in the art that may improve cellular uptake of a conjugate antisense oligonucleotide. In some embodiments, the conjugate may be a tissue-targeting conjugate, for example, a carbohydrate conjugate, or a peptide conjugate, or any conjugate known in the art that can target an antisense oligonucleotide of the present disclosure to a specific tissue. In some embodiments, an antisense oligonucleotide of the present disclosure is conjugated with a polyethylene glycol conjugate. In one embodiment, a polyethylene glycol conjugate antisense oligonucleotide optimizes pharmacokinetic properties of the antisense oligonucleotide.

In some embodiments, the present disclosure provides biocleavable analogues of antisense oligonucleotides described herein. In such cases, biocleavable analogues comprise a hydrophobic conjugate that leads to stronger association with cell membranes and a linker. In one embodiment, the linker is a cleavable linker that when cleaved, releases the antisense oligonucleotide, e.g., releases the antisense oligonucleotide into endosomes. In some embodiments, an antisense compound comprises a cleavable linker, wherein the cleavable linker degrades when cleaved. In some embodiments, the linker is a nuclease-cleavable linker comprising a phosphodiester linkage. In some embodiments, the nuclease-cleavable linker comprising a phosphodiester linkage is about 2 to about 8 nucleotides. For example, a nuclease-cleavable phosphodiester linker can be 3, 4, 5, 6, 7, 8 nucleotides in length, or longer, e.g., 9, 10, 11, 12, 13, 14, 15, 16, 17, 18 nucleotides in length, or longer. In one embodiment, the nuclease-cleavable linker comprises about 6 nucleotides. In some embodiments, the cleavable linker is cleaved after cellular internalization. In some embodiments, the cleavable linker is cleaved within an endosome. In some embodiments, the cleavable linker is cleaved under reducing conditions. In some embodiments, the cleavable linker is cleaved under changing pH conditions, for example the cleavable linker is cleaved when the pH decreases, or when the pH increases. In some embodiments, the cleavable linker is cleaved by an intracellular nuclease or protease. In some embodiments, the cleavable linker is cleaved by an endosomal nuclease or protease.

Pharmaceutical Compositions and Formulations

Provided herein are pharmaceutical compositions and formulations, which include the antisense compounds described herein. For example, the antisense oligonucleotides described herein can be admixed, encapsulated, conjugated or otherwise associated with other molecules, molecule structures or mixtures of compounds. A pharmaceutical composition described herein is formulated to be compatible with its intended route of administration. Examples of routes of administration include intrathecal administration, intraventricular administration or intrastriatal administration. In some embodiments, the administration may employ an implanted device such as an Ommaya reservoir or implanted intrathecal catheter. Solutions or suspensions used for administration can include the following components: a sterile diluent such as water for injection, saline solution, lactated Ringers solution, Elliotts B solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, carbonates or phosphates and agents for the adjustment of tonicity such as sodium chloride or dextrose. The pH can be adjusted with acids or bases, such as hydrochloric acid or sodium hydroxide. The pharmaceutical compositions can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and should be fluid to the extent that easy syringability exists. Pharmaceutical compositions must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols such as manitol, sorbitol, sodium chloride can be included in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, some methods of preparation are vacuum drying and freeze-drying which yields a powder of the active ingredient plus any additional desired ingredient from a previously sterile-filtered solution thereof.

The pharmaceutical compositions and formulations provided herein can, in some embodiments, be conveniently presented in unit dosage form and can be prepared according to conventional techniques well known in the pharmaceutical industry. Such techniques can include bringing into association the active ingredients with the pharmaceutical carrier(s) or excipient(s). In general, the formulations can be prepared by uniformly and intimately bringing into association the active ingredients with liquid carriers, finely divided solid carriers, or both, and then, if necessary, shaping the product (e.g., into a specific particle size for delivery). In one embodiment, the pharmaceutical formulations are prepared for intrathecal, intraventricular or intrastriatal administration in an appropriate solvent, e.g., water or normal saline.

An agent of the present disclosure, e.g., an antisense compound targeting a C9ORF72 transcript can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

An agent of the present disclosure, e.g., an antisense compound targeting a C9ORF72 transcript can also be administered by any method suitable for administration of nucleic acid agents, such as a DNA vaccine. These methods include gene guns, bio injectors, and skin patches, as well as needle-free methods, such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, which can be expressed as the ratio LD50/ED50. Compounds that exhibit large therapeutic indices are useful. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography. In certain embodiments, the compound (e.g., antisense oligonucleotide) is administered at a dose of between about 0.5 mg/mL to about 5.0 mg/mL. In certain embodiments, the compound (e.g., antisense oligonucleotide) is administered at a dose of about 0.5 mg/mL, 1.0 mg/mL, 1.5 mg/mL, 2.0 mg/mL, 2.5 mg/mL, 3.0 mg/mL, 3.5 mg/mL, 4.0 mg/mL, 4.5 mg/mL, or 5.0 mg/mL.

The pharmaceutical compositions can be included in a container, pack, or dispenser together with instructions for administration.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

In certain embodiments, the pharmaceutically acceptable diluent is designed to mimic the composition of cerebrospinal fluid. As such, it may contain divalent salts such as $Mg^{2+}$ and $Ca^{2+}$. Elliotts B solution is a diluent suitable for use in compositions to be delivered into the cerebrospinal fluid. A person of skill in the art will be able to see that other buffer solutions, with variations in the concentrations of different monovalent and divalent ions, may also be suitable as pharmaceutically acceptable diluents.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of an antisense compound which are cleaved by endogenous nucleases within the body, to form the active antisense compound.

Methods of Treatment

The present disclosure provides a method of treating a subject having a C9ORF72-related disorder. Methods of treatment include administering to the subject in need thereof an effective amount of an antisense compound described herein. In some embodiments, the antisense compound comprises a target-recognition sequence that is sufficiently complementary to a C9ORF72 nucleic acid (e.g., a C9ORF72 transcript) to direct cleavage of the C9ORF72 nucleic acid by RNase H.

Methods of treating a subject having a C9ORF72-related disorder are useful in treating any C9ORF72-related disorder known to those of ordinary skill in the art. For example, a C9ORF72-related disorder includes, without limitation, e.g., familial frontotemporal dementia (FTD), amyotrophic lateral sclerosis (ALS), or the combination thereof.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXAMPLES

The present disclosure is further illustrated by the following examples which should not be construed as further limiting.

Example 1: Materials and Methods

Study Design

The experimental approach combined C9 patient derived samples to evaluate selective efficacy in vitro and C9BAC transgenic mice to assess safety, efficacy and duration of effect in vivo. Per experiment, all mice were aged-matched and randomly assigned to control or experimental group. Samples and data were blindly collected, processed and quantified. Molecular and physiological readouts included expression level of V1V3 repeat containing transcripts, all transcripts and peptides, weight of body and organs and motor functions. All outliers were included in data analysis. Exploratory experiments were performed on at least five mice per genotype. Sample size was calculated using the G-power analysis method based on previously defined effect size and standard deviation measuring variability within the sample.

All data were graphed as mean SEM and analyzed using GraphPad Prism Software (Version7). Tests between two groups used the two-tailed student-t test. Tests between multiple groups used one-way analysis of variance (ANOVA) corrected with Bonferroni multiple comparison post-hoc test.

Antisense Oligonucleotides

LNA phosphoramidites were home-made by using standard methods (Koshkin et al., 1998, Am. Chem. Soc., 120, 13252-13253) from the 3'-hydroxyl precursors (Rasayan). All other phosphoramidites were purchased from ChemGenes. 0.1M DDTT (ChemGenes) was used as the sulfurising reagent and 0.25M BTT (AIC) as the activator. ASOs were synthesized on Dr. Oligo 48, ABI394, AKTA Oligopilot10 or AKTA Oligopilot 100 synthesizers, according to the required scale. LNA and MOE phosphoramidites were coupled for 8 minutes. Oligonucleotides were deprotected in concentrated aqueous ammonia at 55° C. for 18 h and purified using ion-exchange chromatography (eluting with 30% acetonitrile in water containing increasing gradients of $NaClO_4$). Final purification, desalting, concentration and pH adjustment were effected by diafiltration in an Amicon centrifugal filter. All oligonucleotides were characterized by LCMS.

Dual Luciferase Reporter Assay System

C9-intron1 containing two $G_2C_2$ motifs (334 nucleotides 5' of the $G_4C_2$ repeat motif and 769 nucleotides in the 3' end) was amplified from blood genomic DNA using the following forward and reverse primers 5'acgtatgcggccgcacgtaacc-tacggtgtc 3' (SEQ ID NO: 17), 5'atacgtgcggccgctaccatcagt-caagtgatg 3' (SEQ ID NO: 18) and cloned in the psi-CHECKTM-2 vector (Promega). C9-intron1 expression was measured with the Dual Luciferase Reporter Assay System (Promega) according to the manufacturer instructions.

Cell Culture

HEK293T cells. HEK293T cells were transfected with 6.5 µg of psiCHECKTM-2 vector (Promega) containing C9 intron1 using Lipofectamine 3000 with P3000 reagent according to the manufacturer instructions (ThermoScientific) in T25 flasks. One day after transfection, cells were plated into a 96-well plate in DMEM supplemented with 10% FBS and treated with the indicated dose of antisense oligonucleotide the next day using Lipofectamine RNAiMax Reagent (ThermoScientific). Cells were lysed 48 hours after antisense oligonucleotide treatment and luciferase signals were quantified.

C9 Patient Derived Fibroblasts. Skin biopsies obtained from two unrelated C9 carriers were cut into small pieces and placed on a culture dish with DMEM supplemented with 15% fetal bovine serum to allow fibroblasts to expand. Antisense oligonucleotide treatment was performed on cells plated in 10 cm dish using Lipofectamine RNAiMax Reagent (ThermoScientific). Total RNA was isolated 72 hours after treatment.

C9BAC Derived Primary cortical neurons. Embryos were removed at E15.5 from pregnant wild-type C57BL/6 females crossed with homozygous C9BAC males. Cortical tissue of each embryo was dissected on ice-cold Hank's Balanced Salt Solution (ThermoScientific). Pooled tissue was minced and digested with 0.05% Trypsin-EDTA (Life Technology) at 37° C. for 12 min. Digestion was halted by addition of 10% FBS/DMEM. Cells were triturated, resuspended in neurobasal media supplemented with Glutamax (ThermoScientific), 2% penicillin/streptomyocin and B27 supplement (ThermoScientific) and seeded at 0.5×10E6 cells/well in 6-well plates pre-coated with poly-ornithine (Sigma). Neurons were treated with antisense oligonucleotide at the indicated dose five days after culture and collected 15 days after treatment.

C9ORF72 Bac Transgenic Mice

C9BAC mice were generated as previously described (Peters et al., Neuron, 2015, 88, 902-909) and backcrossed to C57BL/6. All experimental protocols and procedures were approved by the University of Massachusetts Medical School Institutional Animal Care and Use Committee.

Stereotaxic Pump Implantation and Bolus Injection of ASO in the Mouse Brain

For intracerebroventricular (ICV) infusion of antisense oligonucleotide or PBS vehicle through a micro-osmotic pump (Alzet pump model 1007D attached to Alzet brain infusion kit 3), wild-type C57BL/6 or C9BAC transgenic mice were anesthetized and maintained on 2.5% isoflurane via a nose cone under a stereotaxic frame. Implantation procedure was performed as previously described (Devos et al, 2013, J Vis Exp, e50326-e50326), with a 3 mm cannula implantation 0.2 mm posterior and 1.0 mm lateral to the right of Bregma.

For ICV bolus injection mice were anesthetized with isoflurane and placed into a stereotaxic frame. 10 µL of sterile PBS or antisense oligonucleotide was injected into the right lateral ventricle using the following coordinates: 0.2 mm posterior and 1.0 mm lateral to the right from the Bregma and lowered to a depth of 3 mm.

Mouse Behavior Monitoring

Over the course of treatment and immediately prior to sacrifice, each animal was blindly weighed and evaluated weekly by a trained observer for adverse events, defined as any behavior not typical in a naïve matched control animal, including, but not limited to: limb clasping, tremors, abnormal respiration, paralysis, spasticity, impaired reflex, hyperactivity and lethargy.

Rotarod

Coordinated motor functions were assessed in control and treated mice using the rotarod test as previously described (Peters et al, supra). Briefly, mice were tested weekly beginning two weeks prior to antisense oligonucleotide/vehicle administration and ending at the week of sacrifice. Each animal was given three trials on a 4-40 rpm accelerating rotarod for 5 minutes with a one minute inter trial interval. Latencies to fall for each animal was automatically recorded by a computer and plotted as a mean+/−SEM.

Blood Biochemistry

Whole blood samples were collected after cardiac puncture (terminal procedure). Blood biochemistry was performed using the VetScan Comprehensive diagnostic profile (Abaxis, Union City, Calif.).

Southern Blot

Southern blot was performed on 10 μg genomic DNA isolated using Gentra Puregene Tissue kit (Qiagen). DNA was digested overnight with AluI and DdeI at 37° C. and separated by electrophoresis on a 0.6% agarose gel, transferred to a positively charged nylon membrane (Roche Applied Science), cross-linked by UV, and hybridized overnight at 55° C. with a digoxigenin-labeled G2C4 DNA probe in hybridization mix buffer (EasyHyb, Roche). The digoxigenin-labeled probe was detected with anti-digoxigenin antibody and CDP-Star reagent as recommended by the manufacturer (Roche).

RNA Extraction and Quantitative RealTime-PCR

Total RNA was isolated from snap frozen cortex or spinal cord tissue using Trizol (ThermoScientific) and subsequently treated with DNase I (Qiagen). One μg of total RNA was reverse transcribed into cDNA using random hexamers and MultiScribe reverse transcriptase (ThermoScientific) following the manufacturer's instructions. Quantitative PCR was performed on a StepOnePlus Real-Time PCR system using SYBR Green Master Mix (Applied Biosystems) and 0.2 μM of forward and reverse primers as described in (Jiang et al., Neuron, 2016, 90, 535-550; Tran et al, 2015, Neuron, 87, 1207-1214). Ct values for each sample and gene were normalized to GAPDH. The $2^{(-\Delta\Delta Ct)}$ method was used to determine the relative expression of each target gene.

Fluorescence in situ Hybridization (FISH)

FISH was performed as previously described (Jiang et al., supra; Tran et al, supra) using a 5' end Cy3-conjugated $(G_2C_4)_4$ oligonucleotide DNA probe at 55° C. in hybridization buffer containing formamide 40%/2×SSC/0.1% Tween-20/DNA salmon sperm. Samples were then washed twice in pre-warmed wash buffer (formamide 40%/2×SSC/0.1% Tween-20) and in stringency wash buffer (0.2×SSC/0.1% Tween20) at 55° C. Samples were then mounted in Prolong Gold Antifade reagent with DAPI (ThermoScientific). Confocal images were taken with a Leica TCS SP5 II laser scanning confocal microscope and processed with Leica LAS AF software.

Detection of Poly(GP) and Poly(PR)

Rabbit polyclonal anti-poly GP and PR antibodies were generated to the repeat motif ($GP_8$, $PR_8$) by New England Peptide. Poly(GP) or poly(PR) levels in lysates were measured using a sandwich immunoassay that utilizes Meso Scale Discovery (MSD) electrochemiluminescence detection technology. Tissue samples were lysed in RIPA buffer supplemented with 1× Roche complete protease inhibitor and 1× Halt Phosphatase Inhibitor Cocktail (ThermoScientific) using TissueLyserII (Qiagen) followed by sonication on ice. Samples were gently homogenized on a rocker at 4° C. for 30 min. Debris were removed by centrifugation (15 min, 14 000 g, 4° C.) and the supernatant collected. Total protein concentration was determined using the BCA Protein Assay Kit (Thermo Scientific). 50 μg of total protein diluted in PBS-Tween supplemented with 10% fetal bovine serum was loaded per well in duplicate wells. Serial dilutions of recombinant $(GP)_8$ or $(PR)_8$ spiked in wild-type C57Bl/6 brain protein extracts were used to prepare the standard curve. Response values corresponding to the intensity of emitted light upon electrochemical stimulation of the assay plate using the MSD QUICKPLEX SQ120 were acquired and background corrected using the average response from lysates obtained from wild-type C57Bl/6 brain extract.

Immunohistochemistry

Brains were rapidly removed from euthanized animals. The contralateral hemibrain was post-fixed in 10% formalin. Paraffin-embedded or cryoprotected blocks were cut in 10 μm thick sagittal sections. Slides were permeabilized with Triton 0.1% for 10 min. Non-specific antibody binding was blocked by incubation with 10% goat serum in PBS/Tween 0.01% for one hour. Primary antibodies were diluted in blocking solution and sections were incubated overnight at 4° C. After three washes in PBS/Tween 0.01%, sections were incubated with Alexa fluor-488 or -546 conjugated secondary antibodies diluted in PBS for one hour at room temperature. Autofluorescence was quenched by slide immersion in 0.5% Sudan BlackB in 70% ethanol and cell nuclei were stained with DAPI. Primary antibodies used: mouse anti-NeuN (1:500, Millipore), rabbit anti-P/S antisense oligonucleotide (1:500, home-made). Briefly, a rabbit polyclonal antibody was raised in house by inoculating two female New Zealand White rabbits with a fully-PS-modified, KLH-conjugated antisense oligonucleotide. Boosts and bleeds were carried out at regular intervals over one year, and antisera were used for histology.

Haematoxylin and Eosin (HE) Staining 8 to 10 μm thick sections of mouse liver and kidney were cut from formalin-fixed, paraffin embedded blocks. Standard HE staining was performed.

Statistical Analysis

All data were graphed as mean±SEM and analyzed using GraphPad Prism Software (Version7). Tests between two groups used the two-tailed student-t test. Tests between multiple groups used one-way analysis of variance (ANOVA) corrected with Bonferroni multiple comparison post-hoc test. *$p<0.05$, $p<0.01$, *$p<0.001$, ****$p<0.0001$, ns not significant Example 2: $G_4C_2$-Targeting Antisense Oligonucleotides Reduced the Repeat-Containing C9ORF72 Transcripts in Patient-Derived Fibroblasts and C9BAC Mouse Derived Neurons Optimizing $G_4C_2$-Targeting Antisense Oligonucleotides Because haploinsufficiency of C9ORF72 is thought to be adverse, the antisense oligonucleotides were developed such that they only target the 5'end of V1 and V3 transcripts that bore the $G_4C_2$ repeat expansion, sparing V2 transcript. As it was not fully clear whether the repeat containing intron was retained or spliced out, the antisense oligonucleotide sequences, which differed in their nucleotide sequences and chemical modification at the 2'position of the sugar moiety, being either a locked nucleic acid (LNA) or a 2'-O-methoxyethyl (MOE) substitution, were engineered to target the intron-repeat junction (FIG. 1A). As shown in FIG. 1A, the repeat expansion (triangles) located in the first intron is expressed in variants 1 and 3 (V1-V3). Variant 2 (V2), the most abundant, starts from a different transcription start site (black arrow) and does not include the repeat expansion. V2 and V3 encode the main C9ORF72 protein isoform. Dark grey boxes represent untranslated regions (UTR); light grey boxes represent exons; black lines represent introns. Antisense oligonucleotides used in this study (grey bars designated "ASO") target the intronic region flanking the repeat expansion. Others have previously tested this particular design in patient derived samples with success (Jiang et al., supra; Donnelly et al., 2013, Neuron, 80, 415-428; Lagier-Tourenne et al., 2013, Proc. Natl. Acad. Sci. U.S.A, 110, E4530-9).

Figure 1B:
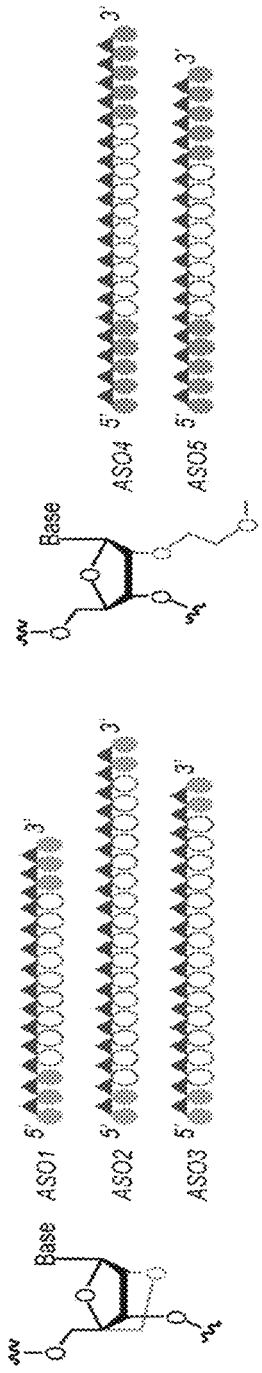
FIG. 1B depicts the schematic of ASOs and their chemical modifications used in this example: green circle, locked nucleic acid (LNA); blue circle, 2'-O-2-methoxyethyl RNA (2'-O-MOE); empty circle, DNA; dark green triangle, phosphorothioate nucleotide linkage (PS).

To remain compatible with RNase H-mediated degradation, which required an unmodified central region, the antisense oligonucleotides were designed as "gapmers", in which only 5' and 3' end ribonucleotides carried these substitutions (FIG. 1B). In FIG. 1B, the green circle was locked nucleic acid (LNA); the blue circle was 2'-O-2-methoxyethyl RNA (2'-O-MOE); the empty circle was DNA; the dark green triangle was phosphorothioate nucleotide linkage (PS). LNA substitutions contained a methylene bridge between the 2' and 4' positions, which "locked" the ribose backbone in a conformation that favors complementary base pairing to its RNA target. MOE substitutions increased stability and potency of antisense oligonucleotides and were components of two FDA-approved drugs (Finkel et al., 2017, N. Engl. J. Med., 377, 1723-1732; Raal et al., 2010, Lancet, 375, 998-1006). In addition to these sugar modifications, each phosphodiester (PO) inter-nucleoside linkage was substituted to a phosphorothioate (PS) linkage in which one non-bridging oxygen atom was replaced with a sulfur atom, greatly increasing stability by blocking nucleolytic degradation (Eckstein et al., 2014, Nucleic Acid Ther, 24, 374-387) (FIG. 1B). Furthermore, a methyl group was attached to each cytosine at the 5' position, a modification that had been shown to mitigate potential immune responses to antisense oligonucleotides in vivo (Krieg et al., 2002, Annu. Rev. Immunol. 20, 709-760).

Figure 2A:
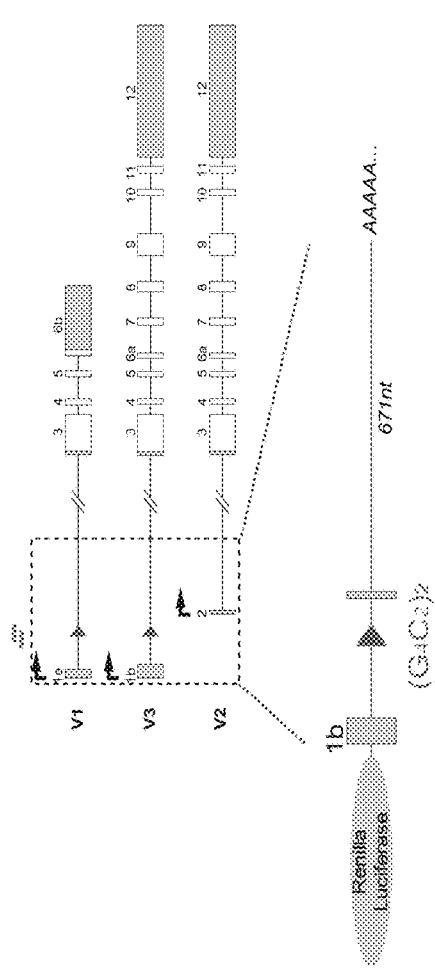
FIG. 2A depicts the schematic of the C9ORF72 non-coding region containing two repeat motifs cloned into the dual luciferase assay system.

To screen for antisense oligonucleotides that suppressed the expression of transcripts V1, V2 and V3, a dual luciferase assay was developed (FIG. 2A). An initial test screen was done to a large number of antisense oligonucleotides candidates before it was narrowed down to five.

Testing $G_4C_2$-Targeting Antisense Oligonucleotides in Cultured Cells

Figure 2B:
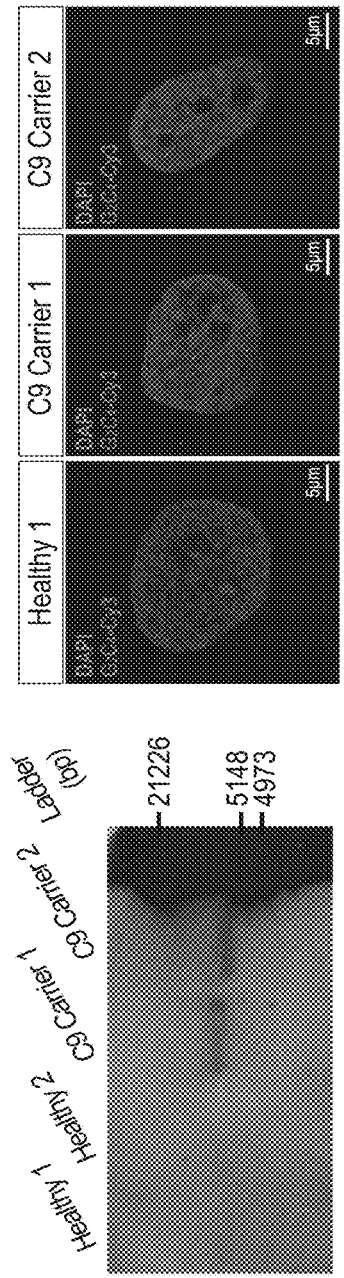
FIG. 2B depicts Southern blot and RNA FISH data verifying the $G_4C_2$ repeat expansion in C9 carrier-derived fibroblasts. Left panel, Southern blot of genomic DNA extracted from fibroblasts from two C9 carriers probed with a 5'DIG-$(G_4C_2)_5$-DIG-3' DNA probe show a band of ~10 kbp, representing an expansion of about 1000 repeats. In contrast, DNA from healthy control fibroblasts (non-C9 carriers) did not show a band. Right panel, RNA FISH using a repeat-specific Cy3-labeled DNA probe in fibroblasts reveals multiple RNA foci in red (white arrowhead).

To test $G_4C_2$-targeting antisense oligonucleotides in cultured cells, we first verified that primary fibroblasts derived from two C9-ALS/FTD patients carried more than 1000 $G_4C_2$ repeats and showed $G_4C_2$ RNA foci (FIG. 2B). As shown in FIG. 2B left panel, Southern Blot of genomic DNA extracted from two non C9 carriers and two C9 carriers derived fibroblasts probed with a 5'DIG-$(G_4C_2)_5$-DIG-3' DNA probe show a band of ~10 kbp, representing an expansion of about 1000 repeats. In the right panel of FIG. 2B, RNA FISH using a repeat specific Cy3 DNA probe in fibroblasts reveals multiple RNA foci in red (white arrowhead). Primary fibroblasts derived from two C9-ALS/FTD patients mentioned supra were then treated with antisense oligonucleotides 1-5 at a dose of 100 nM in the presence of cationic lipid. The sequence of antisense oligonucleotides 1-5 (ASO1-5) are shown below in Table 1.

TABLE 1

Antisense oligonucleotides (ASOs) used in cultured cells

| Name | Sequence (5'-3') |
|---|---|
| ASO 1 | CCCTAGCGCGCGC<u>ACT</u> (SEQ ID NO: 22) |
| ASO 2 | CCCGGCCCCTAGCGCGCGAC (SEQ ID NO: 23) |
| ASO 3 | GCCCCTAGCGCGCGACTC (SEQ ID NO: 24) |
| ASO 4 | CCCGGCCCCTAGCGC<u>GCGAC</u> (SEQ ID NO: 25) |
| ASO 5 | GCCCCTAGCGCGC<u>GACTC</u> (SEQ ID NO: 26) |

Where underlined sequences represent a 2'-O-(2-methoxyethyl) modification and bold sequences represent an LNA modification.

After 72 hours, we assayed the level of V1-V3 repeat containing transcripts by qRT-PCR. While the non-targeting control (NTC) sequence had no significant effect on V1-V3 level as compared to the untreated cultures (UT), all five ASOs significantly reduce V1-V3 expression to almost undetectable levels in patient fibroblasts (FIG. 3A). As shown in FIG. 3A, both LNA and 2'-O-MOE ASOs significantly reduced the level of repeat containing transcripts at a dose of 100 nM 72 h after lipid-mediated delivery in patient derived fibroblasts, as measured by qRT-PCR. A more in-depth characterization of each compound in patient-derived cells and in a HEK293 human cell line expressing a dual reporter assay (FIG. 2A) showed a dose-dependent decreased expression of V1-V3 or C9 intronic target RNA (FIG. 3B). In the left panel of FIG. 3B, dose response of ASOs 2-5 in fibroblasts were shown; in the right panel, dose response of ASOs 1-5 in HEK293 cells transfected with the C9Luc reporter assay were shown. All data were plotted from 5 points non-linear fit dose response curve. To determine if ASO treatment also affects RNA foci, a hallmark of C9-ALS/FTD (DeJesus-Hernandez et al., 2011, Neuron, 72, 245-256; Gendron et al., 2013, Acta Neuropathol. 126, 829-844; Zu et al., 2013, Proc. Natl. Acad. Sci. U.S.A. 110, E4968-77; Donnelly et al., supra; Lagier-Tourenne et al., supra; Almeida et al., 2013, Acta Neuropathol. 126, 385-399; Mizielinska et al., 2013, Acta Neuropathol. 126, 845-857; Sareen et al., 2013, Sci Transl Med 5, 208ra149), we labeled these RNA foci by FISH then quantified number of cells with foci and the number of foci per cell. 72 hours after a 100 nM ASO treatment, the number of cells with foci was markedly reduced from 80% in the untreated condition to 20-40% in the treated conditions; moreover, fewer foci per cell were detected, showing that all five ASOs were potent inhibitors of $G_4C_2$ RNA foci (FIG. 4A). Representative images of RNA foci visualized by FISH in patient derived fibroblasts untreated or treated with ASO for 72 h were shown in the left panel of FIG. 4A. The right panel showed the % of nuclei per 50 cells without foci (light grey), with 1-4 foci (dark grey) or with more than 5 foci (black) when cells were treated with no ASO, a non-targeting control ASO (NTC), LNA modified ASOs (ASOs 1-3) or 2'-O-MOE modified ASOs (ASOs 4-5). To determine whether in vivo CNS delivery of these five ASOs was feasible, we evaluated the capacity of each ASO to "self-deliver" (to be taken up gymnotically without transfection reagents) and remain active in neurons. Primary cortical neurons were derived from E15.5 C9BAC embryos and treated with 1 μM of each ASO at 5 days in vitro (DIV). 15 days after treatment (20 DIV), expression of human V1, V3 (repeat-containing) transcripts was significantly reduced (from 40% reduction with ASO1 to 80% with ASO3) in all treated conditions as compared to the non-targeting control or untreated condition (FIG. 4B). As shown in FIG. 4B, both LNA and 2'-O-MOE ASOs significantly reduce the level of repeat containing transcripts two weeks after 100 nM delivery without lipid assistance (gymnotic delivery) in primary cortical neurons derived from C9BAC mice.

From these in vitro experiments, we concluded that in various cell models (HEK 293 cells expressing a C9 intron1 reporter assay, C9-ALS/FTD patient-derived fibroblasts, C9BAC mouse-derived cortical neurons), ASOs 1-5 (FIG. 1B) all potently inhibited expression of V1 and V3 (repeat-containing) transcripts while sparing V2 and all were efficiently taken up by neurons without assistance.

Figures 5A, 5B:
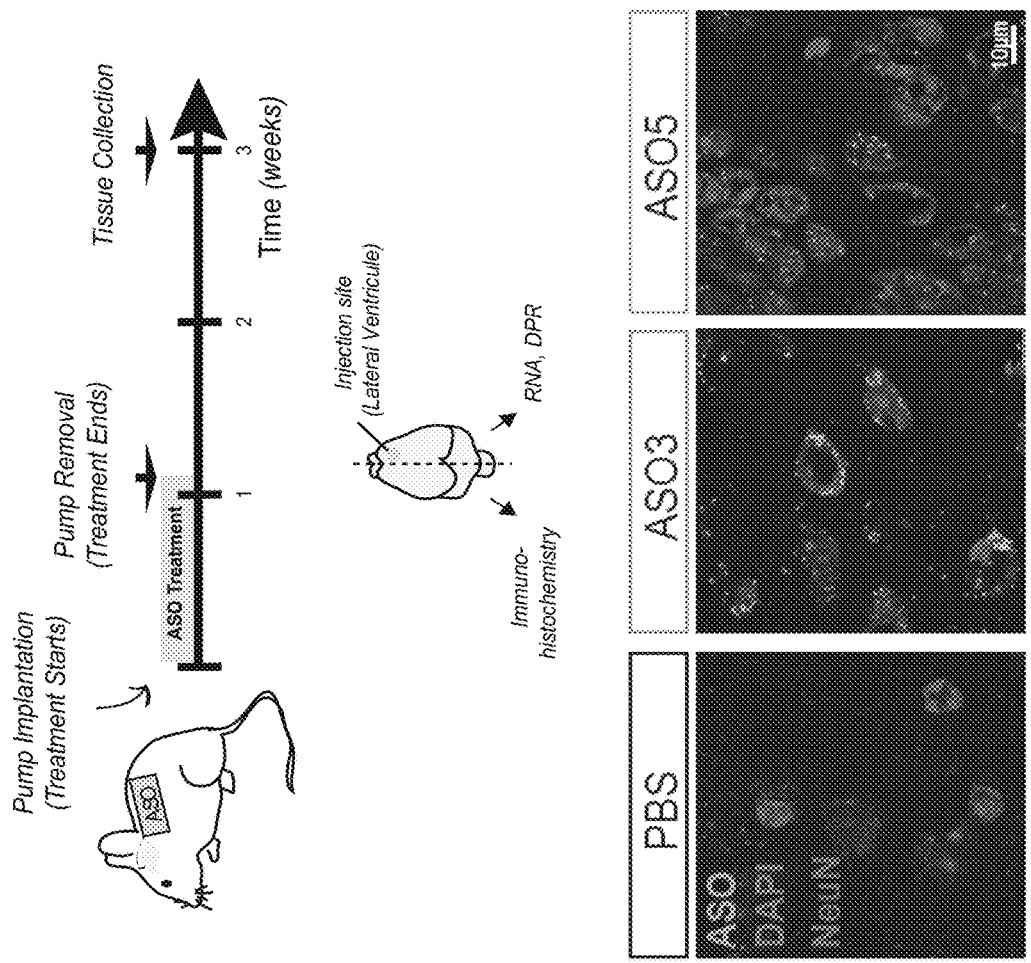
FIG. 5A depicts ASO sequences and their in vivo response in 4-6-month-old wild-type mice after ICV bolus injection: bold green, LNA; bold blue, MOE; italic black, DNA (ASO1, ccctagcgcgcgcgact, SEQ ID NO: 22; ASO2, cccggccctagcgcgcgac, SEQ ID NO: 23; ASO3, gcccctagcgcgcgactc, SEQ ID NO: 24; ASO4, cccggccctagcgcgcgac, SEQ ID NO: 25; and ASO5, gcccctagcgcgcgactc, SEQ ID NO: 26).
FIG. 5B depicts the schematic of experimental design in heterozygous C9BAC mice (top panel) and that ASO3 and ASO5 (green) were taken up in neurons (red)—nuclei counterstaining in blue. In top panel, vehicle control (PBS), a non-targeting control ASO (NTC) and 25 to 200 nmol of ASO3 and ASO5 were infused into the right lateral ventricle of 5-6-month-old C9BAC mice over 7 days. Brain and spinal cord were harvested and dissected two weeks after pump removal for RNA and DPR analysis (spinal cord and ipsilateral brain hemisphere), and ASO staining (contralateral brain hemisphere).

Example 3: G4C2-Targeting ASOs Selectively Reduced the C9ORF72 Repeat-Containing Transcripts and Polydipeptides after CNS Infusion in C9BAC Mice We next evaluated the properties of these ASO's in vivo in wild-type (WT) and C9ORF72 transgenic mice. ASOs did not efficiently cross the blood-brain barrier (Geary et al., 2015, Adv. Drug Deliv. Rev. 87, 46-51). They could, however, be delivered to the brain tissue and spinal cord through the surrounding cerebral spinal fluid (CSF) via an intracerebroventricular (ICV) bolus injection or osmotic pump infusion (Rigo et al., 2014, J. Pharmacol. Exp. Ther. 350, 46-55). Before determining if our ASOs were effective in diminishing expression of the repeat containing transcripts in vivo in C9BAC mice, we first assessed their tolerability in wild-type C57BL/6 mice. Each animal received a single ICV bolus dose of our five ASO. Each treatment group consisted of 2-4 mice. While these WT mice tolerated 30 nmol of MOE modified ASOs 4-5, more than 5 nmol of LNA-modified ASOs 1-3 were lethal. Mice injected with ASOs 1, 2 and 4 had severe seizures upon recovery from anesthesia or did not survive 24 hours post-injection, while mice treated with ASOs 3 and 5 (that share the same nucleotide sequence but differ by their sugar modification) remained alert and responsive to stimuli with no obvious detrimental effects attributable to the treatment up to one week after injection (FIG. 5A). FIG. 5A summarized the ASO sequences and their in vivo response in 4-6-month-old wild-type mice after ICV bolus injection: bold green, LNA; bold blue, MOE; italic black, DNA.

Encouraged by the safety profile of ASOs 3 and 5 in WT mice, we then compared their tolerability and efficacy in C9BAC transgenic mice via ICV administration. C9BAC transgenic mice generated in our laboratory expressed approximately 600 $G_4C_2$ repeat motifs within a truncated human C9ORF72 gene (from exons 1-6). Although these mice did not develop a motor phenotype, they fully recapitulated the distinct disease hallmarks including repeat containing RNA foci and DPR (Peters et al., supra), and thus were a suitable C9-ALS/FTD mouse model for assessing efficacy of ASOs 3 and 5 activities in vivo.

Outside of the CNS, some LNA-modified ASOs was observed to be more potent but might also be more toxic as compared to MOE-modified ASOs (Swayze et al., 2007, Nucleic Acids Research 35, 687-700). Indeed, in our C9BAC mice, we were not able to safely perform intracerebroventricular infusions with more than 10 nmol of any of these three LNA-modified compounds using bolus injections. To overcome this limitation, we next used osmotic pumps, which allowed infusion over time of a higher amount of LNA modified ASO (ASO3) and permitted comparison its potency with the MOE-modified version (ASO5). Increasing doses of each ASO were continuously infused over 7 days into the right lateral ventricle of aged matched heterozygous C9BAC mice through a cannula using an implanted Alzet osmotic pump (FIG. 5B, top). Top panel of FIG. 5B showed the schematic of experimental design in heterozygous C9BAC mice. Vehicle control (PBS), a non-targeting control ASO (NTC) and 25 to 200 nmol of ASO3 and ASO5 were infused into the right lateral ventricle of 5-6-month-old C9BAC mice over 7 days. Brain and spinal cord were harvested and dissected two weeks after pump removal for RNA and DPR analysis (spinal cord and ipsilateral brain hemisphere), and ASO staining (contralateral brain hemisphere). The bottom panel showed that ASO3 and ASO5 (green) were taken up in neurons (red)—nuclei counterstaining in blue. Five to seven animals were used per group condition and animals infused with PBS or a non-targeting ASO were used as controls. Brains of animals sacrificed two weeks after the 7-day infusion demonstrated widespread ASO distribution throughout the brain with associated neuronal uptake (FIG. 5B, bottom).

Figure 7A:
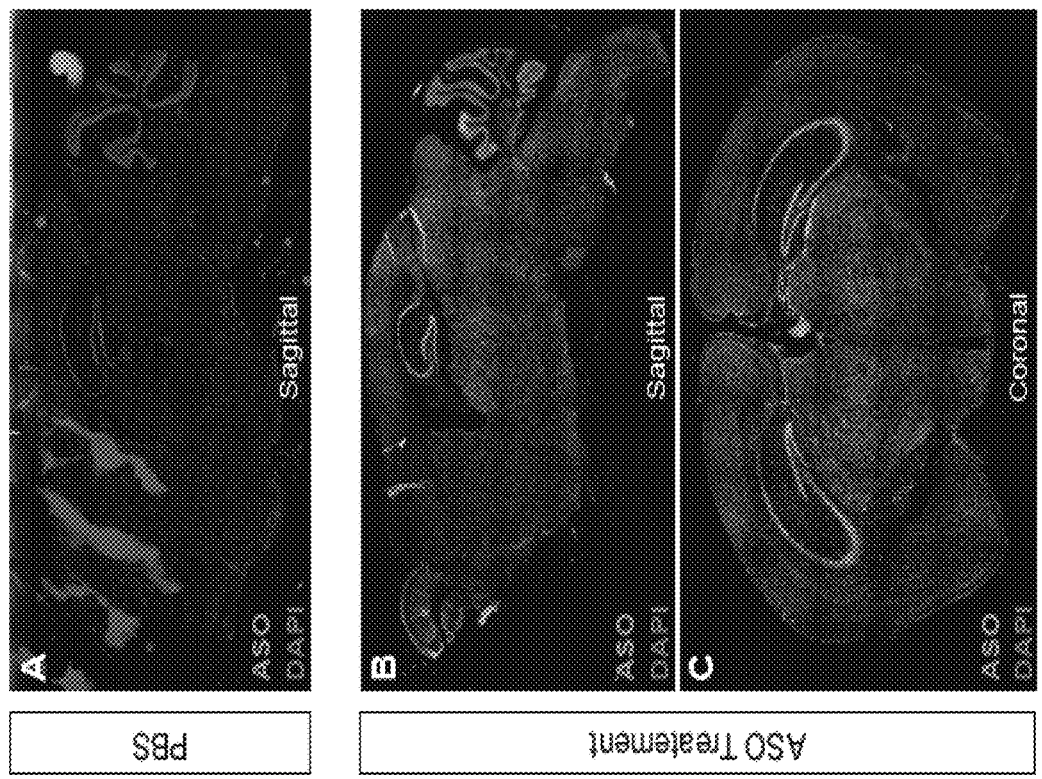
FIG. 7A depicts the relative expression of polyGP in the cortex of mice treated with ASO3 (green) and ASO5 (blue) assayed by sandwich immunoassay. Data are represented as mean SEM (top panel) and % of body weight loss at end point relative to before treatment (bottom panel).

The cortex and spinal regions of animals treated with ASO3 and ASO5 demonstrated potent, dose-dependent reduction in V1 and V3 repeat containing transcripts in both the cortex and spinal cord regions as compared to PBS infused animals; no such reduction was seen in the control animals treated with non-targeting ASOs (FIG. 6A). FIG. 6A showed the expression of V1-V3 repeat containing transcripts in cortex and spinal cord quantified by qRT-PCR in mice infused with PBS (dark grey), NTC ASO (light grey), ASO3 (green) or ASO5 (blue) at the indicated dose. For each dose level, n=5-7, except NTC group (n=3). Importantly, despite their impact on V1 and V3, neither ASO3 nor ASO5 produced any substantial reduction of the level of the V2 transcript (and hence the total C9ORF72 transcript variants) (FIG. 6B). FIG. 6B showed the expression of all transcripts in cortex and spinal cord quantified by qRT-PCR in mice infused with PBS (dark grey), NTC ASO (light grey), ASO3 (green) or ASO5 (blue) at the indicated dose. For each dose level, n=5-7, except NTC group (n=3). Poly-GP DPR was also reduced in the cortex of mice treated with both ASO3 and 5 (FIG. 7A, top). The top panel of FIG. 7A showed the relative expression of polyGP in the cortex of mice treated with ASO3 (green) and ASO5 (blue) assayed by sandwich immunoassay. Data are represented as mean±SEM.

With chronic infusion, the LNA and MOE-modified ASOs were overall well-tolerated at all tested doses. No adverse behavioral side effects were observed throughout the course of ASO administration and all animals remained healthy until they were sacrificed at 21 days. Routine clinical blood chemistry and liver and kidney morphology after HE staining revealed no abnormalities (data not shown). Body weight monitoring from treatment onset to the time of sacrifice revealed an average loss of 10% as compared to initial body weight before treatment; this was likely related to the pump implantation surgery as it also occurred in mice infused with PBS. At the 100 nmol dose, mice receiving the LNA compound ASO3 showed more weight loss (18%) (FIG. 7A, bottom). The bottom panel of FIG. 7A showed the % of body weight loss at end point relative to before treatment.

These results in vivo in C9BAC mice demonstrated that although there was comparable potency after slow chronic pump infusion, the MOE modified ASO5 was better tolerated than the LNA modified ASO3. This difference was dramatic following bolus infusions but also evident after chronic administration infusions.

Figure 7B:
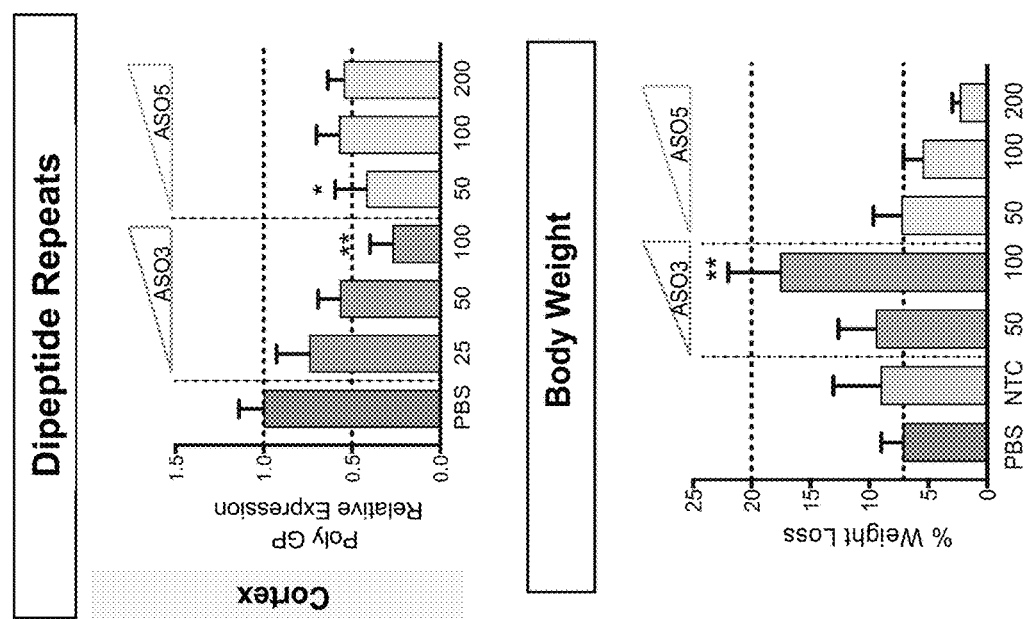
FIG. 7B depicts the distribution of fully PS modified ASO in wild-type C57Bl6 mice three weeks after bolus injection. Panel A-B: sagittal view of an hemibrain of a mouse injected with PBS (A) or ASO (B). Green represented ASO distribution, blue represented nuclei. Panel C: coronal view of a mouse injected with ASO.

Example 4: Reducing the Phosphorothioate Content of ASO5 Improved its Safety Profile without Affecting its Biological Activity after a Single CNS Administration in C9BAC Mice To study the pharmacodynamic properties of ASO5 in the nervous system of C9BAC mice after bolus injection (and to define the best dosing scheme), we first performed in vivo experiments that demonstrated that ASO5 delivered by bolus injection distributes broadly throughout the mouse CNS (FIG. 7B). This finding was consistent with previous reports showing excellent ASO tissue distribution after bolus infusion (and improved pharmacodynamics activity in liver and brain tissues as compared to chronic administration (Rigo et al., supra; Geary et al., supra)). We then identified the maximum tolerated dose of ASO5 in wild-type C57BL/6 mice, which we defined as the highest dose that did not cause seizure or unacceptable side effects (cf. material and method) over a week after injection. No mice survived a bolus injection of 50 nmol of ASO5 while all the 8 mice injected with 30 nmol remained alert and well over the course of treatment (FIG. 8A, left). In the left panel of FIG. 8A: green triangle, phosphorothioate linkage (PS); green lane, phosphodiester linkage (PO); blue, 2'-O-MOE; black, DNA: red star highlights the position of PS/PO difference between ASO5-1 and ASO5-2. The right panel showed the chemical structures of PO and PS linkage. This low MTD notably limits the dosing scheme and narrows the therapeutic window. To achieve a better balance of safety and efficacy, we sought to improve the efficacy and tolerability of ASO5, which had a fully modified backbone with all inter-nucleotide linkages being phosphorothioate (PS) (FIG. 8A).

Despite their advantages (improved resistance to nucleases and improved cellular uptake), the PS modification also shows increased protein binding that can lead to toxicity (Eckstein et al., supra; Agrawal et al., 1999, Biochim. Biophys. Acta 1489, 53-68). Because CSF has relatively low nuclease activity (Whitesell et al., 1993, Proc. Natl. Acad. Sci. U.S.A. 90, 4665-4669; Campbell et al., 1990, J. Biochem. Biophys. Methods 20, 259-267), we reasoned that we could reduce the number of PS linkages to generate a less toxic ASO without compromising activity in the nervous system. Our first attempt consisted of introducing a PS linkage only every other nucleotide. Injection of 50 nmol of this "skipped" ASO was tolerated but still not satisfactory, as mice showed abnormal behavior (slow movement, less reactive to stimuli) in the first 24 hours after treatment (data not shown). ASO5 also carried MOE wing modifications on the ribose of the five end or wing nucleotides, which improved target hybridization and nuclease resistance. We therefore introduced PS linkages only at the termini and in the central "gap" nucleotide region that were not MOE modified. ASO5-1 and ASO5-2 differed only in the presence or absence of a PS linkage between nucleotides 5-6 and 13-14. This modification pattern significantly improved the tolerability of ASO5. ASO5-1 had a maximum tolerated dose (MTD) of 60 nmol. ASO5-2 was safely injected in non-transgenic mice with no adverse events at a dose of 80 nmol, 2.5-fold greater than ASO5 (FIG. 8A, left).

To study further their biological activity, we tested these modified ASOs in C9-ALS/FTD fibroblasts. 72 hours after lipid mediated treatment, ASO5-1 and ASO5-2 significantly reduced the level of V1 and V3 repeat containing transcripts as observed with ASO5 without altering the total level of C9 transcripts (FIG. 8B). The left panel of FIG. 8B showed the effect of 100 nM of a mixed PS/PO on ASO5 efficacy in patient-derived fibroblasts on V1-V3. The right panel showed all the effect of 100 nM of a mixed PS/PO on ASO5 efficacy in patient-derived fibroblasts on all expression level. Furthermore, an in vitro dose response study revealed no significant difference in potency between ASO5, ASO5-1 and ASO5-2 (FIG. 9A). FIG. 9A showed the dose response of ASO5, ASO5-1 and ASO5-2 to C9-ALS/FTD fibroblasts at 72 hours.

Figure 11:
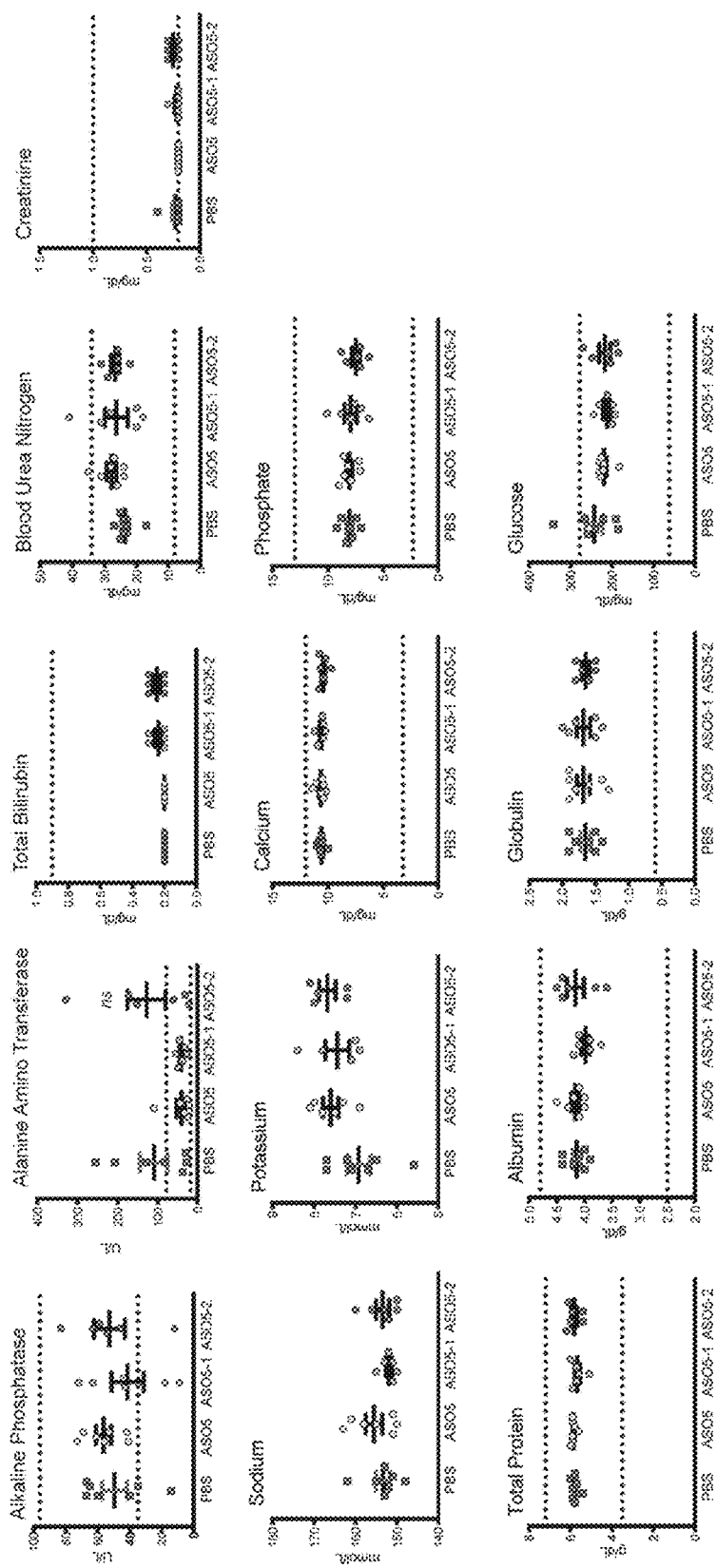
FIG. 11 depicts a panel of blood chemistries at 3 weeks after intracerebroventricular injection of ASO5-2.
Figures 12A, 12B:
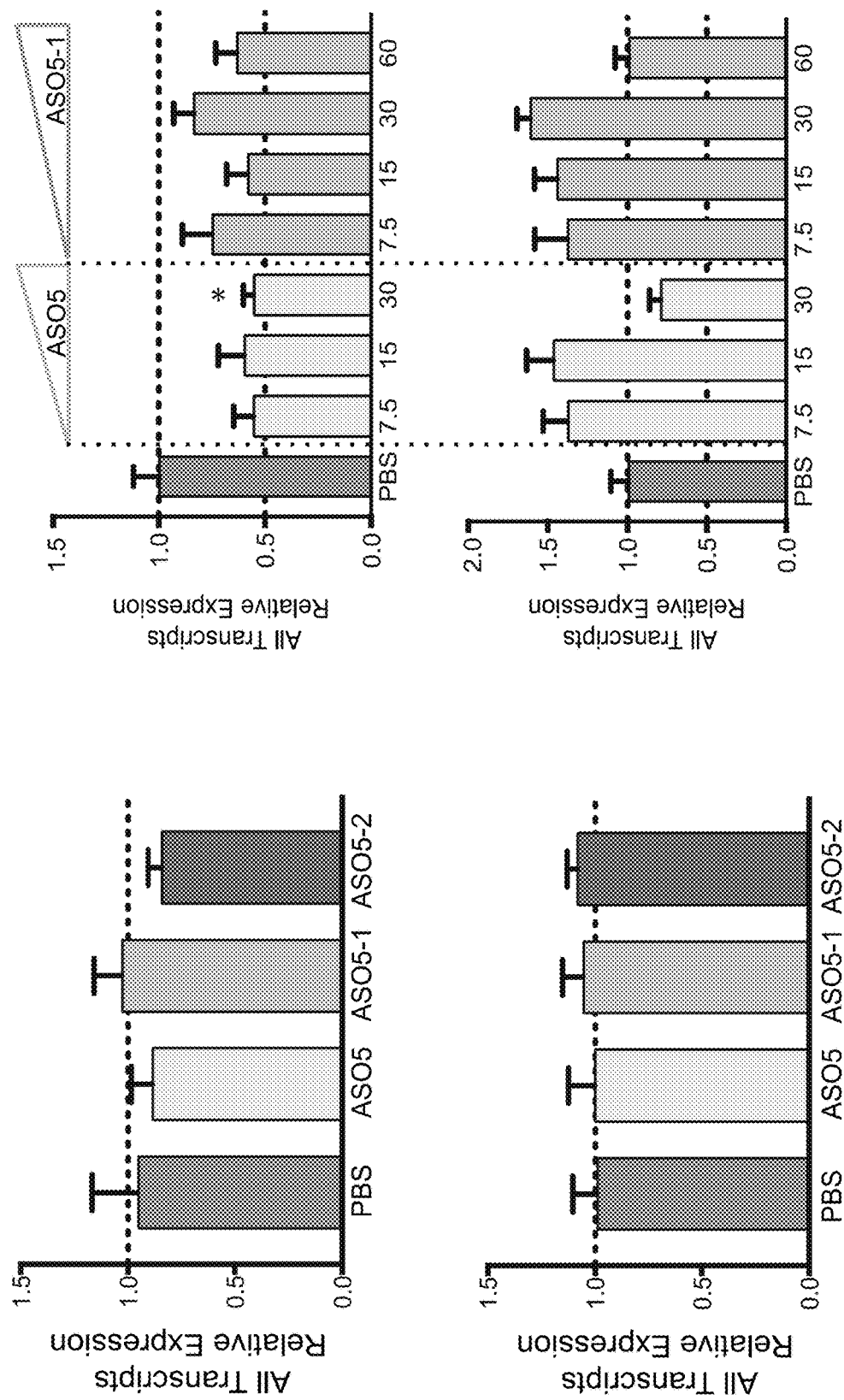
FIG. 12A depicts the expression of all transcripts in cortex and spinal cord quantified by qRT-PCR in mice treated with PBS (dark grey), ASO5 (light blue), ASO5-1 (medium blue) and ASO5-2 (dark blue) eight weeks after administration of 30 nmol of each ASO. For each ASO group, n=5-7.
FIG. 12B depicts the dose response of all transcripts to ASO5 and ASO5-1 in brain and spinal cord.
Figures 13A, 13B:
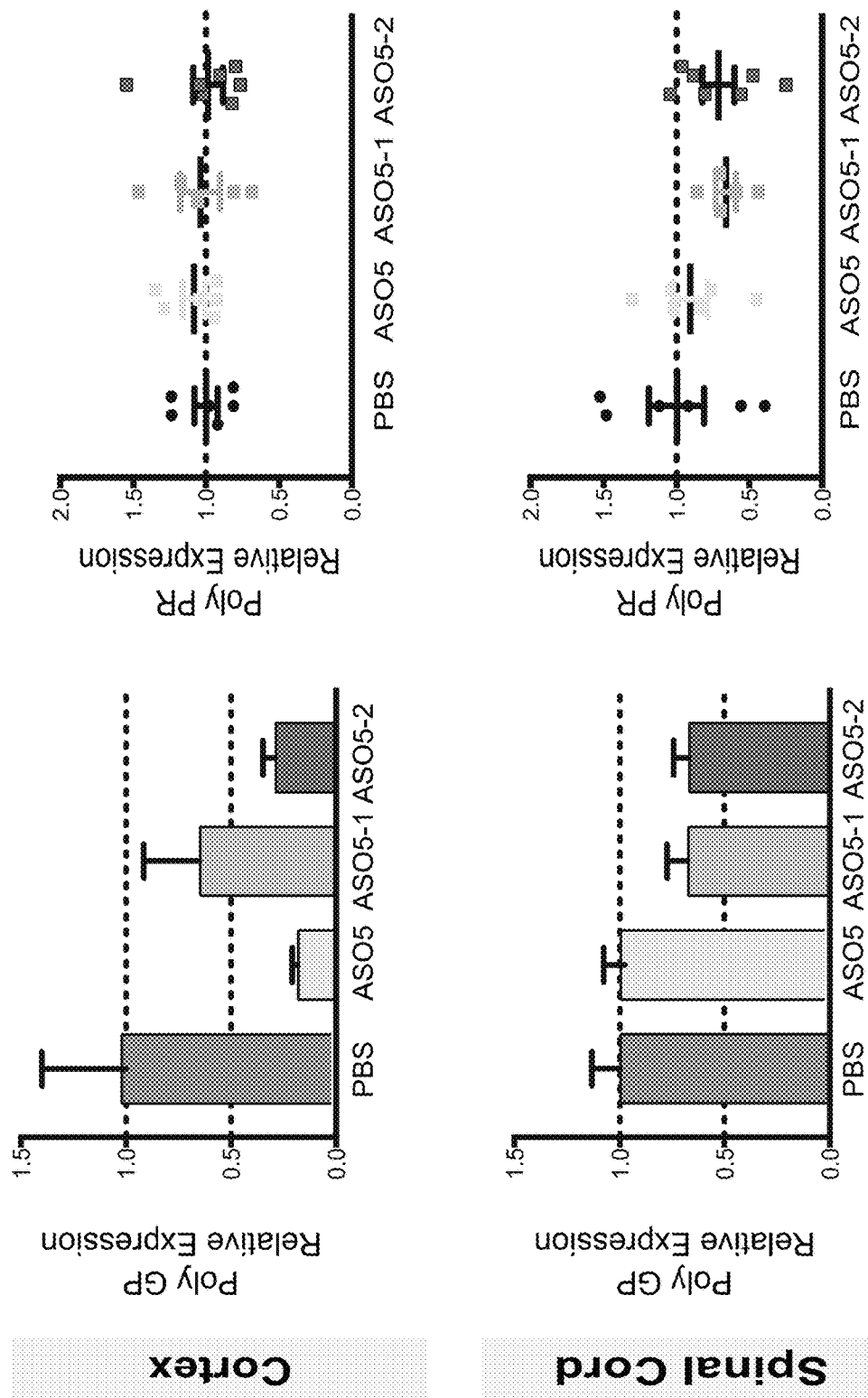
FIG. 13A-FIG. 13B depicts the expression of the polydipeptides polyGP (FIG. 13A) and polyPR (FIG. 13B) in cortex and spinal cord of mice treated with PBS (dark grey), ASO5 (light blue), ASO5-1 (medium blue) or ASO5-2 (dark blue) eight weeks after administration of 30 nmol of each ASO. For each ASO group, n=5-7.

To determine if these results would translate in vivo, we first administered 30 nmol of each ASO via a bolus ICV injection in C9BAC mice and analyzed the efficacy of each ASO eight weeks after injection (FIG. 9B, left). The left panel of FIG. 9B showed the schematic of experimental design in heterozygous C9BAC mice. Vehicle control (PBS), ASO5, ASO5-1 or ASO5-2 were injected into the right lateral ventricle of 5-6 month old C9BAC mice. Brain and spinal cord were harvested and dissected eight weeks after treatment for RNA and DPR analysis. The mid panel showed that no significant change in body weight was observed eight weeks after ASO treatment. The right panel showed that at 3 weeks, ASO5-2 did not cause weight loss. These results indicated that each treatment was well tolerated, with no adverse side effects or significant weight loss observed (FIG. 9B, mid, right). Routine blood chemistry testing revealed no abnormalities (FIG. 11). FIG. 11 showed a panel of blood chemistries at 3 weeks after intracerebroventricular injection of ASO5-2. Mice treated with 30 nmol of ASO5 and ASO5-2 had a significantly reduced level of V1 and V3 (repeat-containing) transcripts in cortex and spinal cord as compared to the PBS treated group (FIG. 10A). The left panel of FIG. 10B showed the expression of V1 and V3 (repeat-containing) transcripts in cortex and spinal cord quantified by qRT-PCR. The right panel showed that 30 nmol of ASO5 and ASO5-2 treatment had minimal effect on total transcripts (FIG. 12). FIG. 12A showed the expression of all transcripts (I, M) in cortex and spinal cord quantified by qRT-PCR. FIG. 12B showed the dose response of all transcripts to ASO5 and ASO5-1 in brain and spinal cord. This result indicated that absence of PS inter-nucleotide linkages between two MOE modified nucleotides did not impair biological activity in vivo (FIG. 13) eight weeks after treatment. In contrast, ASO5-1, which lacked the PS linkage at the junction between a MOE modified and an unmodified DNA nucleotide, achieved only ~25% knock down of V1-V3 at a 30 nmol dose (FIG. 10B). Furthermore, at the highest dose of ASO5-1 tested in this experiment (60 nmol), the maximal efficacy was only ~60% in the cortex and spinal cord (FIG. 10B).

Based on both its efficacy and tolerability profile, this study defines ASO5-2 as the best compound from our series to take forward for a deeper characterization.

Example 5: Sustained and Potent Effect of Mixed-Backbone ASO5-2 in the CNS of Two C9BAC Mouse Models We performed studies in heterozygous C9BAC mice to investigate a full in vivo dose response of ASO5-2 (FIG. 14A). As shown in FIG. 14A, vehicle control (PBS) and a single injection of 1, 5, 15, 30, 60 or 80 nmol of ASO5-2 was administered in of 5-6-month-old heterozygous C9BAC mice. Brain and spinal cord were collected and analyzed 24 hours, 3, 8, 12 or 20 weeks after treatment. The result revealed an IC50 of 4.75 nmol (FIG. 14B) in the cortex of C9BAC mice three weeks after treatment. In the left panel of FIG. 14B, PBS, 1, 5, 15, 30 or 60 nmol of ASO5-2 was injected into the right lateral ventricle of mice, the expression of V1 and V3 (repeat-containing) transcripts and all transcripts was analyzed 3 weeks after injection. The right panel showed a dose response curve after using the Hill equations nonlinear regression model. The relative expression of all transcripts is represented as a dotted black line and as a blue line for V1 and V3 (repeat-containing) transcripts. IC50 estimated at 4.75 nmol. For each dose group, n=6-7. At 4.75 nmol there was also a significant, dose-dependent reduction of polyGP (FIG. 15A, left). In contrast, no change was detected for polyPR, a peptide synthesized from the antisense strand (FIG. 15A, right). In the left panel of FIG. 15A, PBS, 1, 5, 15, 30 or 60 nmol of ASO5-2 was injected into the right lateral ventricle of mice, the expression of poly-GP was analyzed. In the right panel of FIG. 15A, the expression of poly-PR was analyzed from the same set of samples.

Figure 17A:
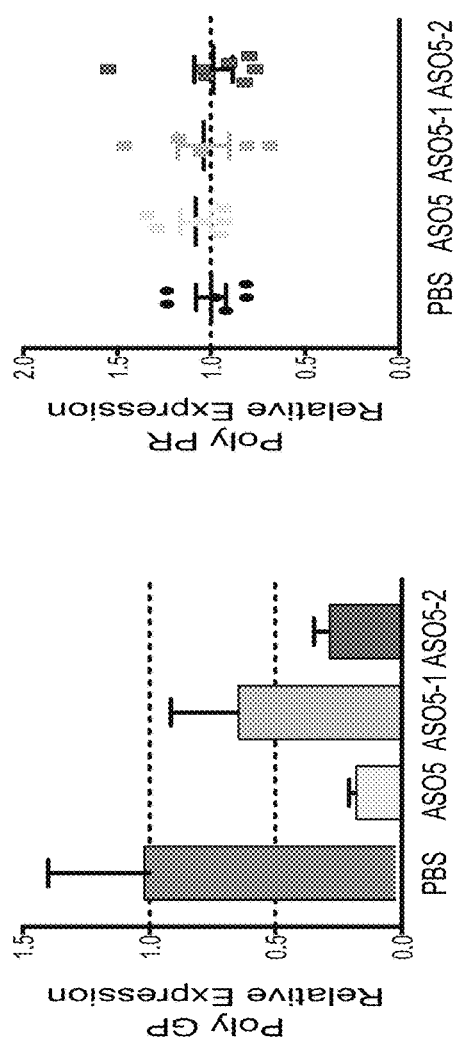
FIG. 17A depicts the expression of poly-GP and poly-PR in cortex. The analysis was performed 8 weeks after a single dose injection of 30 nmol of ASO5, ASO5-1 and ASO5-2. For each group, n=5-7.

The foregoing studied showed that absence of PS linkages in ASO5 between two MOE nucleotides (ASO5-2) did not impair biological activity in vitro and in vivo three weeks after treatment. However, since PS linkages also protect ASOs from nuclease degradation, we wondered if the duration of effect of ASO5-2 would be comparable to its fully PS modified parent ASO5. To address this question, we injected C9BAC transgenic mice with 30 nmol of ASO5-2 and analyzed the level of V1 and V3 transcripts 24 hours, three, eight or 20 weeks after injection (FIG. 14A). No effect was observed on the V1 and V3 target RNA 24 hours after injection (FIG. 15B). In FIG. 15B, a time course experiment was performed in mice treated with 30 nmol of ASO5-2, tissues were collected and analyzed at 24 hours, 3 weeks, 8 weeks, 12 and 20 weeks after treatment. Expression of V1 and V3 (repeat-containing) transcripts was analyzed in cortex 24 hours, 3, 8, 12 or 20 weeks after a single dose injection of ASO5-2. As previously described, a significant and specific reduction of ~80% of V1 and V3 (repeat-containing) transcripts but not total C9 transcripts was observed three weeks after injection (FIG. 14B) that was sustained up to twenty weeks in the cortex (FIG. 15B, FIG. 16A). In FIG. 16A, FIG. 16A showed the expression of V1 and V3 (repeat-containing) transcripts and all transcripts in cortex of mice treated with 30 nmol of ASO5, ASO5-1 and ASO5-2 for 8 weeks, for each group, n=5-7. Analogously, we also observed a reduction in the levels of the polyGP proteins of ~80% (FIG. 16B) but no reduction in polyPR, which is generated from the anti-sense strand of intron 1, at eight weeks after injection (FIG. 17A, FIG. 15A, right). In FIG. 16B, a time course experiment was performed in mice treated with 30 nmol of ASO5-2, tissues were collected and analyzed at 24 hours, 3 weeks, 8 weeks, 12 and 20 weeks after treatment. Expression of poly-GP was analyzed in cortex 24 hours, 3, 8, 12 or 20 weeks after a single dose injection of ASO5-2. FIG. 17A showed the expression of poly-GP and poly-PR in cortex in mice 8 weeks after a single dose injection of 30 nmol of ASO5, ASO5-1 and ASO5-2. For each group, n=5-7. The suppression of V1 and V3 (repeat-containing) transcripts at 20 weeks after a single dose (FIG. 15B) was comparable to that observed with 30 nmol of ASO5 eight weeks after injection (FIG. 10A).

Figure 17B:
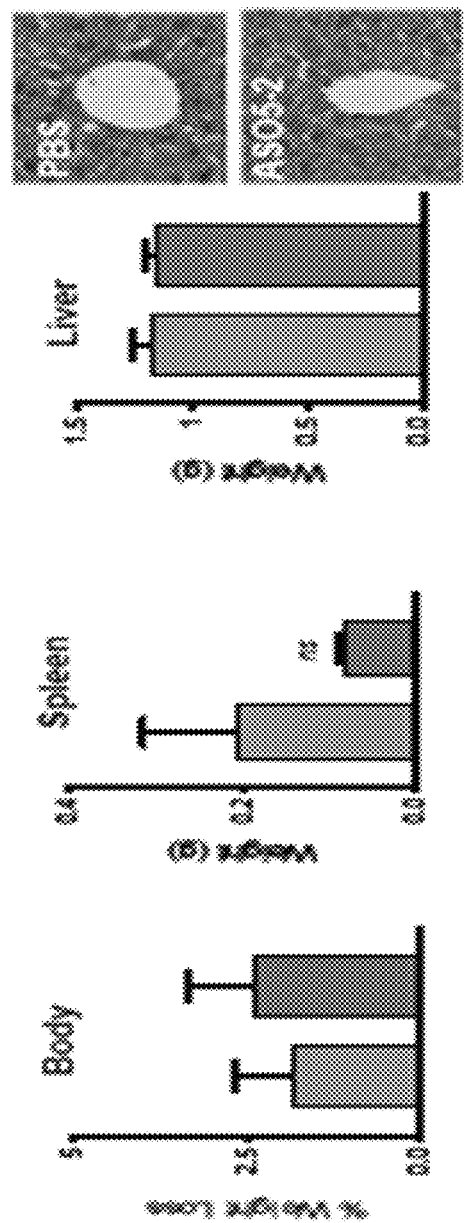
FIG. 17B depicts that no significant weight change in whole body (left), spleen (middle), liver (right) or morphology was observed after treatment.

Immediately prior to sacrifice, no significant body weight loss or behavioral adverse events (as defined in example 1) were detected in animals treated with ASO5-2 or the PBS control (FIG. 17B). Likewise, no change in liver, kidney and spleen weight or morphology was observed (FIG. 17B) As shown in FIG. 17B, no significant change in body weight, spleen or liver was observed after treatment. No apparent change in morphology was observed either. Finally, to further assay the tolerability of ASO5-2 treatment, we analyzed the coordinated motor functions of mice treated with ASO5-2 or injected with vehicle PBS or NTC. Seven mice per group were tested in a blinded manner on their rotarod performance weekly after treatment for 19 weeks. No motor deficit was observed in the treated group, strengthening the tolerability of ASO treatment (FIG. 18A). FIG. 18A showed that ASO treatment did not alter motor performance on a 5-minute accelerating rotarod task during the treatment course.

Example 6: Combined Suppression of Expression of Sense and Anti-Sense Transcripts of C9ORF72

Data suggested that the PR polydipeptide generated from the anti-sense transcript of the C9ORF72 gene was cytotoxic. Accordingly, if the polydidpetides were implicated in neuropathology mediated by this gene, the optimal suppression therapy for C9ORF72 would entail silencing both the sense and the anti-sense transcripts. Therefore, we generated additional ASOs that reduced levels of the C9ORF72 anti-sense transcript (i.e. the antisense transcript expressed from the same region but the opposite strand as C9ORF72 intron 1). Twenty-six candidate ASOs were screened by hybridization in patient fibroblasts (FIG. 18B). FIG. 18B showed the % of nuclei per 100 fibroblasts without foci (light grey), with 1-9 foci (dark grey) or with more than 10 foci (black) after a 72-hour treatment with vehicle control and ASOs targeting the C9 antisense transcript. Two of these, AS-ASO2 and AS-ASO6 (indicated by red stars) were tested in vivo for three weeks using two lines of C9ORF72 mice (Peters et al., supra; O'Rourke et al., 2015, Neuron, 88, 892-901) alone and in combination with ASO5-2 (FIG. 19A). The left panel of FIG. 19A showed the schematic of experimental design in heterozygous C9 mice derived from the Baloh lab. The right panel shows the expression of V1 and V3 (repeat-containing) transcripts and all transcripts as assayed by qRT-PCR. AS-ASO6 did not suppress V1-V3 or total transcript levels, while as expected, ASO5-2 again selectively targeted V1-V3 (FIG. 19A, right panel). We also assayed sense and anti-sense transcripts using branched DNA. FIG. 19B showed the expression of sense repeat containing transcripts (left panel) and antisense repeat containing transcripts (right panel) 3 weeks after injection of vehicle control (PBS), 60 nmol of non-targeting control (NTC), 30 nmol of ASO5-2 or AS ASO6 and a combination of 30 nmol ASO5-2 and 30 nmol of ASO6. The sense transcript was suppressed by ASO5-2 and the combination of ASO5-2 and AS-ASO6 but not by AS-ASO6 alone (FIG. 19B, left panel). The anti-sense transcript was suppressed not only by AS-ASO6 and the combination of AS-ASO6 and ASO5-2 but to a surprising degree also by ASO5-2 alone (FIG. 19B, right panel). ASO5-2 alone or in combination with AS-ASO6 suppressed polyGP levels, while AS-ASO6 alone did not (FIG. 20, left). AS-ASO6 and the combination of ASO6 and ASO5-2 showed partial suppression of polyPR, while as expected ASO5-2 did not (FIG. 20, right). As shown in FIG. 20, the expression of poly-GP (left panel) and poly-PR (right panel) was analyzed 3 weeks after injection of vehicle control (PBS), 60 nmol of non-targeting control (NTC), 30 nmol of ASO5-2 or AS ASO6 and a combination of 30 nmol ASO5-2 and 30 nmol of ASO6.

Example 7: Administration of ASO5-2 to a Patient with ALS

Figure 21:
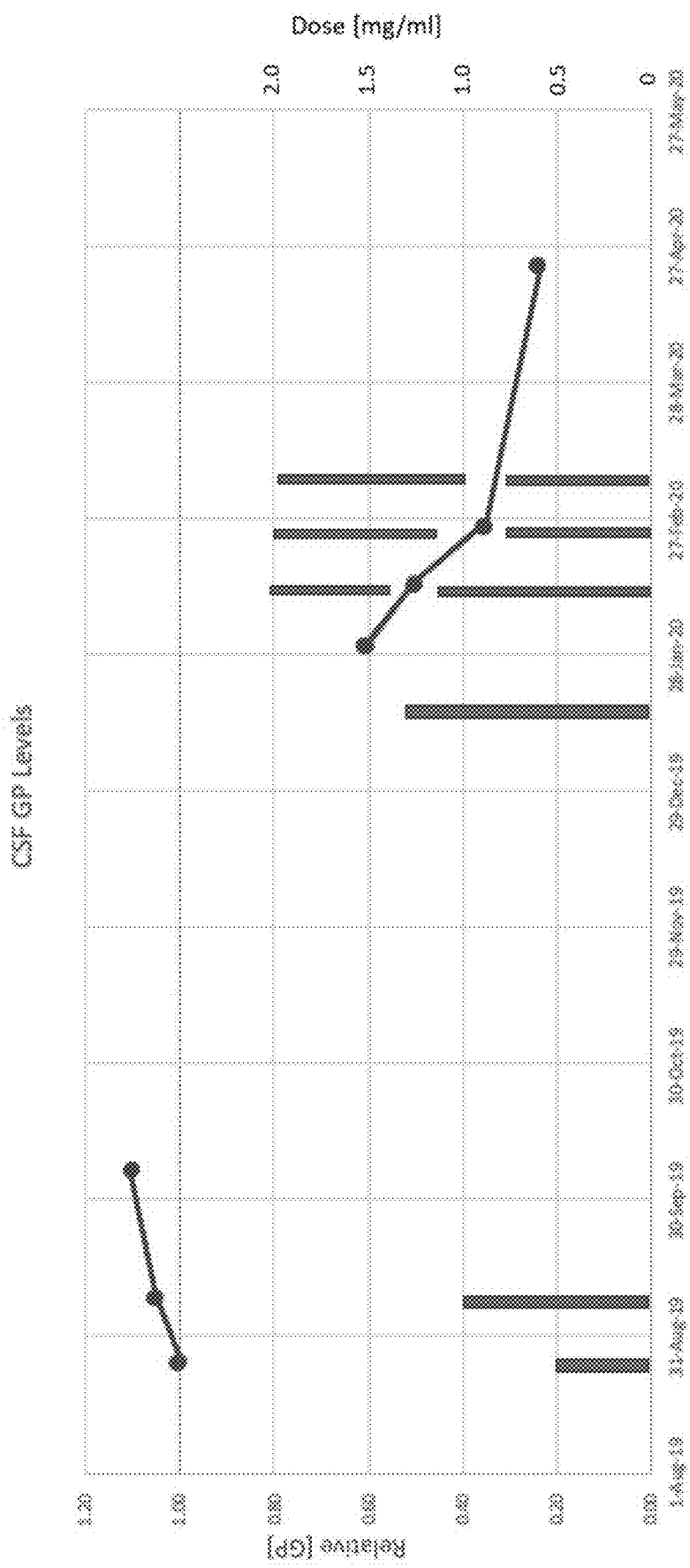
FIG. 21 depicts a dose-escalation study of ASO5-2 treatment in a patient with C9orf72 ALS. Increasing dose of ASO5-2 (bars, right y axis) and increasing number of doses over time (x axis) correlates with decreasing levels of polyGP (dots and line, left y axis).
Figure 22:
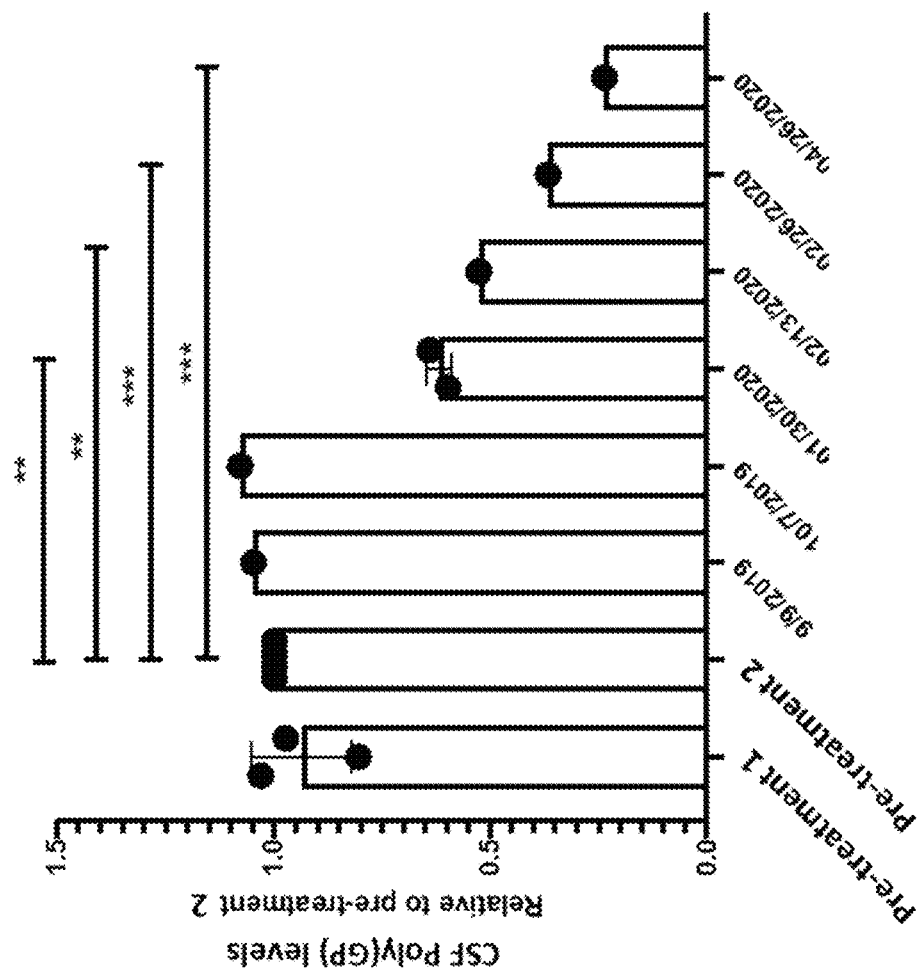
FIG. 22 depicts a consistent drop in CSF levels of poly(GP) over time after beginning treatment with ASO5-2.

To further demonstrate the efficacy of the antisense oligonucleotides of the disclosure, ASO5-2 was administered to a human patient diagnoses with ALS. All patient studies were carried out with FDA and IRB approval. ASO5-2 was dissolved in USP grade Lactated Ringers Solution to a concentration of 11 mg/mL. The solution was sterile-filtered under aseptic conditions into a sterile syringe, and immediately administered to the patient by intrathecal injection at the escalating doses indicated in FIG. 21. The doses ranged from 0.5 mg/mL to 2.0 mg/mL. The patient was monitored for 24 hours after injection. At subsequent timepoints as indicated, patient cerebrospinal fluid (CSF) was sampled by lumbar puncture, and CSF levels of poly(GP) were evaluated using ELISA (FIG. 22). The data demonstrates that ASO5-2 treatment in a patient leads to a dose-dependent reduction in CSF levels of poly(GP), indicating that it has suppressed expression of the isoforms of C9orf72 RNA that harbor the ALS-causing mutant expansion. While poly(GP) levels were measured in the instant case, it will be understood that other dipeptide repeat proteins, such as poly(GR), poly(GA), poly(PA), and poly(PR), can be reduced in the CSF as well.

Poly(GP) Elisa Protocol

Protein samples were prepared by: 1) harvesting the desired tissue or cells, 2) adding 1×RIPA buffer and Protease Inhibitor, 3) adding a metal bead to the samples and lysing in a Qiagen tissuelyser for 30 seconds and a frequency of 30, 4) centrifuging the sample at 4° C. for 15 minutes at 12,000RPM, 5) collecting the supernatant and adding to a new tube, 6) performing a BCA assay to determine protein concentration, 7) diluting samples with RIPA buffer in a stock plate with each sample being at a final concentration of 1.6 μg/μl in a total volume of 150-200 μl. The coating antibody was prepared by diluting the capture antibody to 2 μg/ml in PBS and adding 5 μl to each well over the little circle in the center of each plate. The plate was then incubated overnight at 4° C. Washing and blocking was then performed by washing the plate 3× with 150 μl of PBS+ 0.1% Tween (PBS-T). Blocking was performed with 150 μl of PBS-T+10% FBS for at least 1 hour at room temperature. The blocking buffer was then removed and the sample added. Detection was then performed.

What is claimed is:

1. An antisense oligonucleotide comprising a region of complementarity to a C9ORF72 sense transcript sequence of 5' GAGUCGCGCGCUAGGGGC 3' (SEQ ID NO: 9), wherein the antisense oligonucleotide comprises internucleotide linkages from 5' to 3' of sooossssssssssooos, wherein each s is a phosphorothioate linkage and each o is a phosphodiester linkage.

2. The antisense oligonucleotide of claim 1, wherein the antisense oligonucleotide is 18 to 80 nucleotides in length.

3. The antisense oligonucleotide of claim 1, comprising the formula:

A-B-C, wherein:
A comprises from about 0 to about 8 modified nucleotides;
B comprises from about 4 to about 18 deoxyribonucleic acid (DNA) nucleotides and/or DNA-like nucleotides; and
C comprises from about 0 to about 8 modified nucleotides;

and the overall length of the antisense oligonucleotide is about 18 to about 30 nucleotides.

4. The antisense oligonucleotide of claim 1, comprising a nucleic acid sequence with at least 90% sequence identity to the nucleic acid sequence set forth in SEQ ID NO: 10 (GCCCCTAGCGCGCGACTC).

5. The antisense oligonucleotide of claim 1, comprising a sequence modification pattern of $X_sX_oX_oX_oX_sX_sX_sX_sX_sX_sX_sX_sX_sX_oX_oX_oX_sX$, wherein
s represents a phosphorothioate internucleotide linkage;
o represents a phosphodiester internucleotide linkage; and
X is an adenosine, a guanosine, a cytidine, or a thymine comprising a 2'-O-(2-methoxyethyl) modification.

6. An antisense oligonucleotide comprising the sequence $G_sC_oC_oC_oC_sT_sA_sG_sC_sG_sC_sG_sC_sG_sC_sG_oA_oC_oT_sC$, wherein
s represents a phosphorothioate internucleotide linkage;
o represents a phosphodiester internucleotide linkage;
A is an adenosine comprising a 2'-O-(2-methoxyethyl) modification;
G is a guanosine comprising a 2'-O-(2-methoxyethyl) modification;

C is a cytidine comprising a 2'-O-(2-methoxyethyl) modification;

T is a thymine comprising a 2'-O-(2-methoxyethyl) modification; and each cytosine is a 5-methylcytosine.

7. A method for inhibiting expression of C9ORF72 gene in a cell, the method comprising:
(a) introducing into the cell an antisense oligonucleotide of claim 1; and
(b) maintaining the cell produced in step (a) for a time sufficient to obtain degradation of the transcript of the C9ORF72 gene, thereby inhibiting expression of the C9ORF72 gene in the cell.

8. A method of treating or managing Amyotrophic Lateral Sclerosis (ALS) comprising administering to a patient in need of such treatment or management a therapeutically effective amount of the antisense oligonucleotide of claim 1.

9. A method of reducing the level of a dipeptide repeat protein in a patient, comprising administering to a patient in need of such reduction a therapeutically effective amount of the antisense oligonucleotide of claim 1.

10. The antisense oligonucleotide of claim 1, wherein the antisense oligonucleotide is 18 to 30 nucleotides in length.

11. The antisense oligonucleotide of claim 1, comprising at least one modified nucleotide with a modification of a ribose group.

12. The antisense oligonucleotide of claim 11, wherein the modified nucleotide is a 2'-O-methyl, 2'-fluoro, 2'-H, 2'-O-(2-methoxyethyl) (MOE), 2'-O-alkyl, 2'-O-alkoxy, 2'-O-alkylamino, 2'-NH$_2$, or a constrained nucleotide.

13. The antisense oligonucleotide of claim 12, wherein the constrained nucleotide is a locked nucleic acid (LNA), an ethyl-constrained nucleotide, a 2'-(S)-constrained ethyl (S-cEt) nucleotide, a constrained MOE, a 2'-O,4'-C-aminomethylene bridged nucleic acid (2',4'-BNA$^{NC}$), an alpha-L-locked nucleic acid, or a tricyclo-DNA.

14. The antisense oligonucleotide of claim 1, comprising at least one modified nucleotide with a modification of a nucleobase group.

15. The antisense of oligonucleotide of claim 14, wherein each modification of the nucleobase group is 2-thiouridine, 4-thiouridine, N$^6$-methyladenosine, pseudouridine, 2,6-diaminopurine, inosine, thymidine, 5-methylcytosine, 5-substituted pyrimidine, isoguanine, isocytosine, or halogenated aromatic groups.

16. The antisense of oligonucleotide of claim 1, wherein the antisense oligonucleotide is conjugated to a ligand.

17. The antisense oligonucleotide of claim 3, wherein A comprises from about 2 to about 6 modified nucleotides, B comprises from about 6 to about 12 DNA nucleotides and/or DNA-like nucleotides, and C comprises from about 2 to about 6 modified nucleotides.

18. The antisense oligonucleotide of claim 3, wherein B comprises about 8 DNA nucleotides and/or DNA-like nucleotides, and C comprises about 5 modified nucleotides.

19. The antisense oligonucleotide of claim 3, wherein A comprises about 5 modified nucleotides, B comprises about 10 DNA nucleotides and/or DNA-like nucleotides, and C comprises about 5 modified nucleotides.

20. The antisense oligonucleotide of claim 3, wherein A comprises from about 2 to about 6 2'-O-(2-methoxyethyl) (MOE) modified nucleotides, B comprises from about 6 to about 12 DNA-like nucleotides, and C comprises from about 2 to about 6 locked 2'-O-(2-methoxyethyl) (MOE) modified nucleotides.

21. The antisense oligonucleotide of claim 3, wherein A comprises about 5 2'-O-(2-methoxyethyl) (MOE) modified nucleotides, B comprises about 8 DNA-like nucleotides, and C comprises about 5 locked 2'-O-(2-methoxyethyl) (MOE) modified nucleotides.

22. The antisense oligonucleotide of claim 3, wherein A comprises about 5 2'-O-(2-methoxyethyl) (MOE) modified nucleotides, B comprises about 10 DNA-like nucleotides, and C comprises about 5 locked 2'-O-(2-methoxyethyl) (MOE) modified nucleotides.

23. The antisense oligonucleotide of claim 5, wherein each cytidine is a 5-methylcytosine.

24. The method of claim 8, wherein the antisense oligonucleotide is administered to the brain of the patient.

25. The method of claim 8, wherein the antisense oligonucleotide is administered by intrathecal, intraventricular or intrastriatal injection or infusion.

26. The method of claim 25, wherein the injection or infusion comprises administration using an Ommaya reservoir or intrathecal catheter.

27. The method of claim 8, the antisense oligonucleotide is administered at a dose of between about 0.5 mg/mL to about 5.0 mg/mL.

28. The method of claim 8, the antisense oligonucleotide is administered at a dose of about 11 mg/mL.

29. The method of claim 8, the antisense oligonucleotide is formulated in Lactated Ringers Solution.

30. The method of claim 9, wherein the antisense oligonucleotide is administered to the brain of the patient.

31. The method of claim 9, wherein the antisense oligonucleotide is administered by intrathecal, intraventricular or intrastriatal injection, or infusion.

32. The method of claim 31, wherein the injection or infusion comprises administration using an Ommaya reservoir or intrathecal catheter.

33. The method of claim 9, wherein the dipeptide repeat protein comprises one or more of poly(GP), poly(GR), poly(GA), poly(PA), and poly(PR).

* * * * *

```
                        SEQUENCE LISTING

<160> NUMBER OF SEQ ID NOS: 27

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaaguaaaa augcgucgag                                                   20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cuccuuguuu ucuucugguu                                                   20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
caggucuuuu cuuguucacc                                                   20

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ccuccuuguu uucuucuggu                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctcgacgcat ttttactttc                                                   20
```

```
<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaccagaaga aaacaaggag                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggtgaacaag aaaagacctg                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
accagaagaa aacaaggagg                                                  20

<210> SEQ ID NO 9
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gagucgcgcg cuaggggc                                                    18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcccctagcg cgcgactc                                                    18

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ggggccgggg ccggggccgg ggccggggcc                                       30
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctcgacgcat ttttactttc                                            20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaccagaaga aaacaaggag                                            20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtgaacaag aaaagacctg                                            20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
accagaagaa aacaaggagg                                            20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcccctagcg cgcgactc                                              18

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acgtatgcgg ccgcacgtaa cctacggtgt c                               31

```
<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atacgtgcgg ccgctaccat cagtcaagtg atg                                    33

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
ggccccggcc ccggccccgg cccc                                              24

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Pro Gly Pro Gly Pro Gly Pro Gly Pro Gly Pro Gly Pro Gly Pro
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Arg Pro Arg Pro Arg Pro Arg Pro Arg Pro Arg Pro Arg Pro Arg
1               5                   10                  15

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ccctagcgcg cgcgact                                                      17

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cccggcccct agcgcgcgac                                                   20
```

```
<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcccctagcg cgcgactc                                                 18

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cccggcccct agcgcgcgac                                               20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcccctagcg cgcgactc                                                 18

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggggccgggg cc                                                       12
```